US008153424B2

(12) United States Patent
Zhang et al.

(10) Patent No.: US 8,153,424 B2
(45) Date of Patent: Apr. 10, 2012

(54) METHOD OF IN VITRO DIFFERENTIATION OF NEURAL STEM CELLS, MOTOR NEURONS AND DOPAMINE NEURONS FROM PRIMATE EMBRYONIC STEM CELLS

(75) Inventors: Su-Chun Zhang, Middleton, WI (US); Xue-Jun Li, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 690 days.

(21) Appl. No.: 11/932,582

(22) Filed: Oct. 31, 2007

(65) Prior Publication Data

US 2008/0227137 A1 Sep. 18, 2008

Related U.S. Application Data

(60) Continuation-in-part of application No. 11/594,455, filed on Nov. 8, 2006, now Pat. No. 7,972,850, which is a division of application No. 10/928,805, filed on Aug. 27, 2004, now Pat. No. 7,588,937, which is a continuation-in-part of application No. 09/970,382, filed on Oct. 3, 2001, now Pat. No. 6,887,706.

(60) Provisional application No. 60/498,831, filed on Aug. 29, 2003, provisional application No. 60/499,570, filed on Sep. 2, 2003.

(51) Int. Cl.
*C12N 5/08* (2006.01)
*C12N 5/00* (2006.01)
*A01N 63/00* (2006.01)

(52) U.S. Cl. ............ 435/366; 435/376; 435/377

(58) Field of Classification Search .......... None
See application file for complete search history.

(56) References Cited

U.S. PATENT DOCUMENTS

| | | | |
|---|---|---|---|
| 5,843,780 | A | 12/1998 | Thomson |
| 6,200,806 | B1 | 3/2001 | Thomson |
| 6,251,669 | B1 | 6/2001 | Luskin |
| 6,468,794 | B1 | 10/2002 | Uchida et al. |
| 6,497,872 | B1 | 12/2002 | Weiss et al. |
| 6,498,018 | B1 | 12/2002 | Carpenter |
| 6,833,269 | B2 | 12/2004 | Carpenter |
| 6,887,706 | B2 | 5/2005 | Zhang et al. |
| 7,390,659 | B2 * | 6/2008 | Jessell et al. ........... 435/377 |
| 7,588,937 | B2 | 9/2009 | Zhang et al. |
| 2002/0009743 | A1 | 1/2002 | Carpenter |
| 2002/0028510 | A1 | 3/2002 | Sanberg et al. |
| 2002/0114788 | A1 | 8/2002 | Isacson et al. |
| 2002/0168763 | A1 | 11/2002 | Yan et al. |
| 2003/0068819 | A1 | 4/2003 | Zhang et al. |
| 2003/0211605 | A1 | 11/2003 | Lee et al. |
| 2003/0224411 | A1 | 12/2003 | Stanton et al. |
| 2004/0009592 | A1 | 1/2004 | Sabate et al. |
| 2008/0206865 | A1 | 8/2008 | Zhang et al. |

FOREIGN PATENT DOCUMENTS

| | | |
|---|---|---|
| CA | 2315538 A1 | 7/1999 |
| CA | 2443151 A1 | 10/2002 |
| GB | 2421029 B | 4/2008 |
| SG | 119929 | 5/2007 |
| WO | WO 94/16718 A1 | 8/1994 |
| WO | WO 97/47734 A1 | 12/1997 |
| WO | WO 99/20740 A2 | 4/1999 |
| WO | WO 99/20741 A1 | 4/1999 |
| WO | WO 01/51616 A2 | 7/2001 |
| WO | WO 01/81549 A2 | 11/2001 |
| WO | WO 01/83715 A2 | 11/2001 |
| WO | WO 01/88104 A2 | 11/2001 |
| WO | WO 03/104444 A1 | 12/2003 |
| WO | WO 2004/015077 A2 | 2/2004 |
| WO | WO 2004/042018 A2 | 5/2004 |
| WO | WO 2004/081172 A2 | 9/2004 |
| WO | 2005/021720 A2 | 3/2005 |
| WO | WO 2009/057111 * | 5/2009 |

OTHER PUBLICATIONS

Li et al. Directed differentiation of ventral spinal progenitors and motor neurons from human embryonic stem cells by small molecules. Stem Cells 26:886-893, 2008.*
Sinha et al. Purmorphamine activates the Hedgehog pathway by targeting Smoothened. Nature chemical biology 2:29-30, 2006.*
Wichterle et al. Directed differentiation of embryonic stem cells into motor neurons. Cell 110:385-397, 2002.*
Bain G, et al., "Embryonic stem cells express neuronal properties in vitro," Developmental Biology, 168:342-357 (1995).
Brustle O, et al., "In vitro-generated neural precursors participate in mammalian brain development," Proc. Natl. Acad. Sci. USA 94:14809-14014 (1997).
Carpenter M, et al., "Enrichment of neurons and neural precursors from human embryonic stem cells," Exp. Neurol. 172:383-397 (2001).
Ding S & Schultz P, "A role for chemistry in stem cell biology," Nat. Biotechnol. 22:833-840 (2004).
Kawata M, et al., "Neural rosette formation within in vitro spheroids of a clonal human teratocarcinoma cell line, PA-1/NR: role of extracellular matrix components in the morphogenesis," Cancer Res. 51:2655-2669 (1991). Li X, et al., "Differentiation of human embryonic stem cells into motoneurons," The Society for Neuroscience 33rd Annual Meeting, New Orleans, LA (2003).
Li X, et al., "Specification of motoneurons from human embryonic stem cells," Nat. Biotech. 2:215-221 (2005).
Mujtaba T, et al., "Lineage-restricted neural precursors can be isolated from both the mouse neural tube and cultured ES cells," Develop. Biol, 214:113-127 (1999).
Pankratz M, et al., "Directed neural differentiation of human embryonic stem cells via an obligated primitive anterior stage," Stem Cells 25:1511-1520 (2007).
Wu X, et al., "Purmorphamine induces osteogenesis by activation of the hedgehog signaling pathway," Chem. Biol. 11:1229-1238 (2004).
Yan Y, et al., "Induction of midbrain dopamine neurons from human embryonic stem cells," The Society for Neuroscience 33rd Annual Meeting, New Orleans, LA (2003).

(Continued)

Primary Examiner — Quang Nguyen
(74) Attorney, Agent, or Firm — Quarles & Brady, LLP

(57) ABSTRACT

A method of differentiating embryonic stem cells into ventral spinal progenitor cells is disclosed. In one embodiment, the invention comprises culturing a population of cells comprising a majority of cells that are characterized by an early rosette morphology and are Sox1⁻/Pax6⁺ in the presence of retinoic acid, wherein the cells express Hoxb4, but not Otx2 or Bf1.

10 Claims, 17 Drawing Sheets

OTHER PUBLICATIONS

Figure 1:
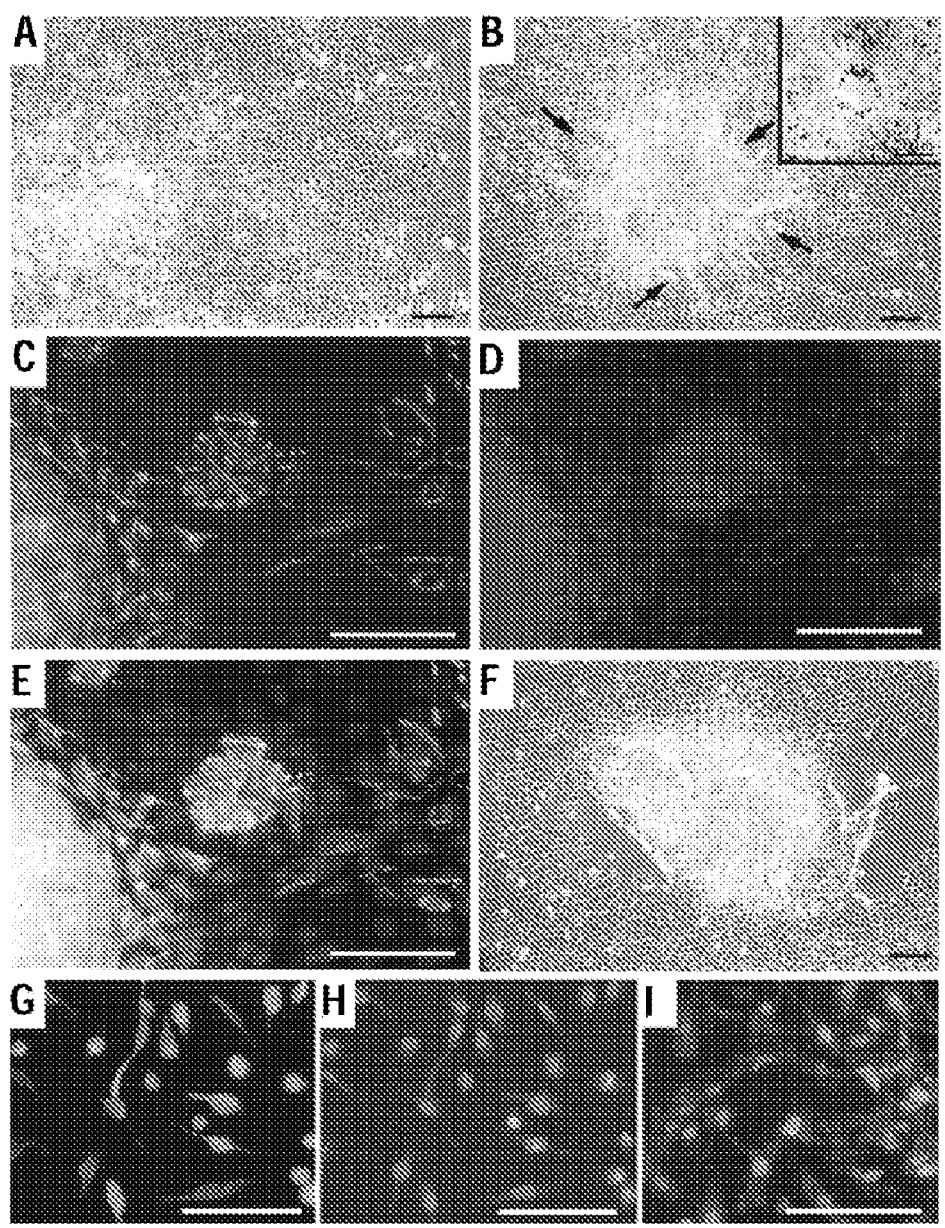

Yan Y, et al., "Directed differentiation of dopaminergic neuronal subtypes from human embryonic stem cells," Stem Cells 23:781-790 (2005).

Zhang S, et al., "In vitro differentiation of transplantable neural precursors from human embryonic stem cells," Nat. Biotechnol. 19:1129-1133 (2001).

Zhang S, et al., "Keystone symposium on pluripotent stem cells," Feb. 6, 2001 (Poster).

S.-H. Lee, et al., "Efficient Generation of Midbrain and Hindbrain Neurons from Mouse Embryonic Stem Cells," Nat. Biotechnol. 18:675-679 (2000).

A. L. Primer et al., "Derivation of Midbrain Dopamine Neurons from Human Embryonic Stem Cells," Proc. Natl. Acad. Sci. UDA 101:12543-12548 (2004).

L. H. Penvy et al., "A Role of Sox1 in Neural Determination," Development 125:1967-1978 (1998).

Du and Zhang, "Neural Differentiation from Embryonic Stem Cells: Which Way?", Stem Cell and Development, 13:372-381 (2004).

* cited by examiner

SEQUENCE LISTING

```
<160> NUMBER OF SEQ ID NOS: 40

<210> SEQ ID NO 1
<211> LENGTH: 20
<212> TYPE: DNA
<213> ORGANISM: Artificial
<220> FEATURE:
<223> OTHER INFORMATION: Synthetic polynucleotide

<400> SEQUENCE: 1
accacagtcc atgccatcac                                              20
```

```
<210> SEQ ID NO 2
<211> LENGTH: 20
<212> TYPE: DNA
<213> ORGANISM: Artificial
<220> FEATURE:
<223> OTHER INFORMATION: Synthetic polynucleotide

<400> SEQUENCE: 2
tccaccaccc tgttgctgta                                              20

<210> SEQ ID NO 3
<211> LENGTH: 23
<212> TYPE: DNA
<213> ORGANISM: Artificial
<220> FEATURE:
<223> OTHER INFORMATION: Synthetic polynucleotide

<400> SEQUENCE: 3
cgatgccttg tgttcaggcg cag                                          23

<210> SEQ ID NO 4
<211> LENGTH: 23
<212> TYPE: DNA
<213> ORGANISM: Artificial
<220> FEATURE:
<223> OTHER INFORMATION: Synthetic polynucleotide

<400> SEQUENCE: 4
agcctttgca gccctcacag gtg                                          23

<210> SEQ ID NO 5
<211> LENGTH: 20
<212> TYPE: DNA
<213> ORGANISM: Artificial
<220> FEATURE:
<223> OTHER INFORMATION: Synthetic polynucleotide

<400> SEQUENCE: 5
gtgggtggag aggagaacaa                                              20

<210> SEQ ID NO 6
<211> LENGTH: 21
<212> TYPE: DNA
<213> ORGANISM: Artificial
<220> FEATURE:
<223> OTHER INFORMATION: Synthetic polynucleotide

<400> SEQUENCE: 6
ttcctccctc aggaaacaat g                                            21

<210> SEQ ID NO 7
<211> LENGTH: 21
<212> TYPE: DNA
<213> ORGANISM: Artificial
<220> FEATURE:
<223> OTHER INFORMATION: Synthetic polynucleotide

<400> SEQUENCE: 7
gggatcggaa actgttactg c                                            21

<210> SEQ ID NO 8
<211> LENGTH: 20
<212> TYPE: DNA
<213> ORGANISM: Artificial
<220> FEATURE:
<223> OTHER INFORMATION: Synthetic polynucleotide

<400> SEQUENCE: 8
```
gtagtcaccc ttgcacagca                                                    20

<210> SEQ ID NO 9
<211> LENGTH: 20
<212> TYPE: DNA
<213> ORGANISM: Artificial
<220> FEATURE:
<223> OTHER INFORMATION: Synthetic polynucleotide

<400> SEQUENCE: 9
ccctggtttc tctgggactt                                                    20

<210> SEQ ID NO 10
<211> LENGTH: 20
<212> TYPE: DNA
<213> ORGANISM: Artificial
<220> FEATURE:
<223> OTHER INFORMATION: Synthetic polynucleotide

<400> SEQUENCE: 10
gcagtctgtg gggtcgtatt                                                    20

<210> SEQ ID NO 11
<211> LENGTH: 21
<212> TYPE: DNA
<213> ORGANISM: Artificial
<220> FEATURE:
<223> OTHER INFORMATION: Synthetic polynucleotide

<400> SEQUENCE: 11
tttatggggc tcagcaagag g                                                  21

<210> SEQ ID NO 12
<211> LENGTH: 22
<212> TYPE: DNA
<213> ORGANISM: Artificial
<220> FEATURE:
<223> OTHER INFORMATION: Synthetic polynucleotide

<400> SEQUENCE: 12
tccacttcat ccttcggttc tg                                                 22

<210> SEQ ID NO 13
<211> LENGTH: 20
<212> TYPE: DNA
<213> ORGANISM: Artificial
<220> FEATURE:
<223> OTHER INFORMATION: Synthetic polynucleotide

<400> SEQUENCE: 13
tcggggtgct tccttgtagc                                                    20

<210> SEQ ID NO 14
<211> LENGTH: 20
<212> TYPE: DNA
<213> ORGANISM: Artificial
<220> FEATURE:
<223> OTHER INFORMATION: Synthetic polynucleotide

<400> SEQUENCE: 14
ttcgtggcag ggactatggg                                                    20

<210> SEQ ID NO 15
<211> LENGTH: 20
<212> TYPE: DNA
<213> ORGANISM: Artificial

```
<220> FEATURE:
<223> OTHER INFORMATION: Synthetic polynucleotide

<400> SEQUENCE: 15
aactccacct tccccgtcac                                                    20

<210> SEQ ID NO 16
<211> LENGTH: 20
<212> TYPE: DNA
<213> ORGANISM: Artificial
<220> FEATURE:
<223> OTHER INFORMATION: Synthetic polynucleotide

<400> SEQUENCE: 16
cttctgtctc gccgaacacg                                                    20

<210> SEQ ID NO 17
<211> LENGTH: 20
<212> TYPE: DNA
<213> ORGANISM: Artificial
<220> FEATURE:
<223> OTHER INFORMATION: Synthetic polynucleotide

<400> SEQUENCE: 17
caacagcaga atggaggtca                                                    20

<210> SEQ ID NO 18
<211> LENGTH: 20
<212> TYPE: DNA
<213> ORGANISM: Artificial
<220> FEATURE:
<223> OTHER INFORMATION: Synthetic polynucleotide

<400> SEQUENCE: 18
ctgggtggaa agagaagctg                                                    20

<210> SEQ ID NO 19
<211> LENGTH: 20
<212> TYPE: DNA
<213> ORGANISM: Artificial
<220> FEATURE:
<223> OTHER INFORMATION: Synthetic polynucleotide

<400> SEQUENCE: 19
tcagaaggag acggaggcta                                                    20

<210> SEQ ID NO 20
<211> LENGTH: 20
<212> TYPE: DNA
<213> ORGANISM: Artificial
<220> FEATURE:
<223> OTHER INFORMATION: Synthetic polynucleotide

<400> SEQUENCE: 20 gtggggtgt taggttctga                                                     20

<210> SEQ ID NO 21
<211> LENGTH: 22
<212> TYPE: DNA
<213> ORGANISM: Artificial
<220> FEATURE:
<223> OTHER INFORMATION: Synthetic polynucleotide

<400> SEQUENCE: 21
aaggaggcag tggcttcaag tc                                                 22
```

```
<210> SEQ ID NO 22
<211> LENGTH: 20
<212> TYPE: DNA
<213> ORGANISM: Artificial
<220> FEATURE:
<223> OTHER INFORMATION: Synthetic polynucleotide

<400> SEQUENCE: 22
cgctcaccag tcgcttcatc                                              20

<210> SEQ ID NO 23
<211> LENGTH: 22
<212> TYPE: DNA
<213> ORGANISM: Artificial
<220> FEATURE:
<223> OTHER INFORMATION: Synthetic polynucleotide

<400> SEQUENCE: 23
tgcctctcct tctgaacctt gg                                           22

<210> SEQ ID NO 24
<211> LENGTH: 20
<212> TYPE: DNA
<213> ORGANISM: Artificial
<220> FEATURE:
<223> OTHER INFORMATION: Synthetic polynucleotide

<400> SEQUENCE: 24
gcgaaatctg ccaccagttg                                              20

<210> SEQ ID NO 25
<211> LENGTH: 20
<212> TYPE: DNA
<213> ORGANISM: Artificial
<220> FEATURE:
<223> OTHER INFORMATION: Synthetic polynucleotide

<400> SEQUENCE: 25
aagaacgcca ccagggagag                                              20

<210> SEQ ID NO 26
<211> LENGTH: 20
<212> TYPE: DNA
<213> ORGANISM: Artificial
<220> FEATURE:
<223> OTHER INFORMATION: Synthetic polynucleotide

<400> SEQUENCE: 26
ttggagtccg aaatgggtcc                                              20

<210> SEQ ID NO 27
<211> LENGTH: 20
<212> TYPE: DNA
<213> ORGANISM: Artificial
<220> FEATURE:
<223> OTHER INFORMATION: Synthetic polynucleotide

<400> SEQUENCE: 27
ggcaacctac gcaagatggc                                              20

<210> SEQ ID NO 28
<211> LENGTH: 20
<212> TYPE: DNA
<213> ORGANISM: Artificial
<220> FEATURE:
<223> OTHER INFORMATION: Synthetic polynucleotide

<400> SEQUENCE: 28
```
tgagggctgt gtctgttcgg					20

<210> SEQ ID NO 29
<211> LENGTH: 20
<212> TYPE: DNA
<213> ORGANISM: Artificial
<220> FEATURE:
<223> OTHER INFORMATION: Synthetic polynucleotide

<400> SEQUENCE: 29
ccaattacaa ccccgacatc					20

<210> SEQ ID NO 30
<211> LENGTH: 20
<212> TYPE: DNA
<213> ORGANISM: Artificial
<220> FEATURE:
<223> OTHER INFORMATION: Synthetic polynucleotide

<400> SEQUENCE: 30
ccgagttctc tgctttcacc					20

<210> SEQ ID NO 31
<211> LENGTH: 21
<212> TYPE: DNA
<213> ORGANISM: Artificial
<220> FEATURE:
<223> OTHER INFORMATION: Synthetic polynucleotide

<400> SEQUENCE: 31
acacgagacc cactttttcc g					21

<210> SEQ ID NO 32
<211> LENGTH: 23
<212> TYPE: DNA
<213> ORGANISM: Artificial
<220> FEATURE:
<223> OTHER INFORMATION: Synthetic polynucleotide

<400> SEQUENCE: 32
tgctggactt gtgcttcttc aac				23

<210> SEQ ID NO 33
<211> LENGTH: 20
<212> TYPE: DNA
<213> ORGANISM: Artificial
<220> FEATURE:
<223> OTHER INFORMATION: Synthetic polynucleotide

<400> SEQUENCE: 33
gatgcccgac ttcaactccc					20

<210> SEQ ID NO 34
<211> LENGTH: 22
<212> TYPE: DNA
<213> ORGANISM: Artificial
<220> FEATURE:
<223> OTHER INFORMATION: Synthetic polynucleotide

<400> SEQUENCE: 34
ccttctgttt ctccgcttcc tg				22

<210> SEQ ID NO 35
<211> LENGTH: 22
<212> TYPE: DNA
<213> ORGANISM: Artificial

```
<220> FEATURE:
<223> OTHER INFORMATION: Synthetic polynucleotide

<400> SEQUENCE: 35
tgattcctcg gttgtttctt gc                                              22

<210> SEQ ID NO 36
<211> LENGTH: 20
<212> TYPE: DNA
<213> ORGANISM: Artificial
<220> FEATURE:
<223> OTHER INFORMATION: Synthetic polynucleotide

<400> SEQUENCE: 36
aaagcagatg ccagccattg                                                 20

<210> SEQ ID NO 37
<211> LENGTH: 21
<212> TYPE: DNA
<213> ORGANISM: Artificial
<220> FEATURE:
<223> OTHER INFORMATION: Synthetic polynucleotide

<400> SEQUENCE: 37
cactgtgacc gaagcactgg t                                               21

<210> SEQ ID NO 38
<211> LENGTH: 20
<212> TYPE: DNA
<213> ORGANISM: Artificial
<220> FEATURE:
<223> OTHER INFORMATION: Synthetic polynucleotide

<400> SEQUENCE: 38
cctctgtcag cttggtcctc                                                 20

<210> SEQ ID NO 39
<211> LENGTH: 20
<212> TYPE: DNA
<213> ORGANISM: Artificial
<220> FEATURE:
<223> OTHER INFORMATION: Synthetic polynucleotide

<400> SEQUENCE: 39
ttcctaccag agtcccaagt                                                 20

<210> SEQ ID NO 40
<211> LENGTH: 20
<212> TYPE: DNA
<213> ORGANISM: Artificial
<220> FEATURE:
<223> OTHER INFORMATION: Synthetic polynucleotide

<400> SEQUENCE: 40
ccctatgtga agccctattt                                                 20
```

METHOD OF IN VITRO DIFFERENTIATION OF NEURAL STEM CELLS, MOTOR NEURONS AND DOPAMINE NEURONS FROM PRIMATE EMBRYONIC STEM CELLS

CROSS-REFERENCE TO RELATED APPLICATION

This application is a continuation-in-part of U.S. patent application Ser. No. 11/594,455 (now U.S. Pat. No. 7,972,850), filed Nov. 8, 2006 now U.S. Pat. No. 7,972,850 (incorporated herein by reference as if set forth in its entirety), which is a divisional of U.S. patent application Ser. No. 10/928,805 (now U.S. Pat. No. 7,588,937) filed Aug. 27, 2004 now U.S. Pat. No. 7,588,937 (incorporated herein by reference as if set forth in its entirety), which is a continuation-in-part of U.S. patent application Ser. No. 09/970,382 (now U.S. Pat. No. 6,887,706), filed Oct. 3, 2001 (incorporated herein by reference as if set forth in its entirety); U.S. patent application Ser. No. 10/928,805 also claims the benefit of U.S. Provisional Patent Application No. 60/498,831, filed Aug. 29, 2003 (incorporated herein by reference as if set forth in its entirety) and U.S. Provisional Patent Application No. 60/499,570, filed Sep. 2, 2003 (incorporated herein by reference as if set forth in its entirety).

STATEMENT REGARDING FEDERALLY SPONSORED RESEARCH OR DEVELOPMENT

This invention was made with government support under NS045926 awarded by the National Institutes of Health. The government has certain rights in the invention.

BACKGROUND OF THE INVENTION

Human embryonic stem cells (hESCs) are pluripotent cells derived from the inner cell mass of pre-implantation embryos (Thomson J, et al., Science 282:1145-1147 (1998)). Similar to mouse embryonic stem cells (mESCs), they can be expanded to large numbers while maintaining their potential to differentiate into various somatic cell types of all three germ layers (Thomson et al., supra; Reubinoff B, et al., Nat. Biotech. 18:399 (2000); Thomson J & Odorico J, Trends Biotech. 18:53-57 (2000); and Amit M, et al., Dev. Biol. 227:271-278 (2000)). The in vitro differentiation of embryonic stem cells (ESCs) provides new perspectives for studying the cellular and molecular mechanisms of early development and the generation of donor cells for transplantation therapies. Indeed, mESCs have been found to differentiate in vitro to many clinically relevant cell types, including hematopoietic cells (Wiles M & Keller G, Development 111:259-267 (1991)), cardiomyocytes (Klug M, et al., J. Clin. Invest. 98:216-224 (1996)), insulin-secreting cells (Soria B, et al., Diabetes 49:157-162 (2000)), and neurons and glia (Bain G, et al., Dev. Biol. 168:342-357 (1995); Okabe S, et al., Mech. Dev. 59:89-102 (1996); Mujtaba T, et al., Dev. Biol. 214:113-127 (1999); and Brustle O, et al., Science 285:754-756 (1999)). Following transplantation into the rodent central nervous system (CNS), ESC-derived neural precursors have been shown to integrate into the host tissue and, in some cases, yield functional improvement (McDonald J, et al., Nat. Med. 5:1410-1412 (1999)). A clinical application of hESCs would require the generation of highly purified donor cells for specific tissues and organs.

Needed in the art is a simple, yet efficient, strategy for the isolation of transplantable neural and motor neuron precursors from differentiating human ES cell cultures.

SUMMARY OF THE INVENTION

Specification of distinct cell types from hESCs is key to the potential application of these naïve pluripotent cells in regenerative medicine. Here we show a near complete restriction of hESCs to ventral spinal progenitors (Olig2+, NKX2.2+, Irx3+/Pax7−) and efficient differentiation of motor neurons (HB9+) by a simple sequential application of retinoid acid (RA), and sonic hedgehog (SHH) in a chemically defined condition. This highly improved ventral spinal progenitor and motor neuron induction over our previous method is due to continued presence of SHH in a suspension culture that promotes proliferation of the Olig2-expressing progenitors. We further discovered that purmorphamine, a small molecule that activates the SHH pathway, could substitute SHH for the generation of ventral spinal progenitors and motor neurons. The new differentiation strategy, even without further purification, facilitates the basic and translational studies employing human motor neurons at a minimal cost.

In a first aspect, the present invention is summarized as a method of creating a population of ventral spinal progenitor cells from ESCs. In one embodiment of the first aspect, the method comprises the steps of: (a) obtaining a population of cells characterized by an early rosette morphology (Pax6+/Sox1−); (b) culturing the cells from step (a) with RA until the cells express Hoxb4, but not Otx2 or Bf1; and (c) culturing the cells of step (b) in a suspension culture with RA and SHH or an activator of the SHH pathway until the cells express Olig2, Nkx2.2, Irx3, but not Pax7.

In some embodiments of the first aspect, the total time period between the propagation of ESCs to development of early rosettes is preferably between 8-10 days; the culturing of the cells in step (b) is preferably between 6-8 days; and the culturing of the cells in step (c) is preferably between 9-14 days. In other embodiments of the first aspect, the total population of Pax6+/Sox1− cells is at least 70% of the total cell population. In still other embodiments of the first aspect, the total population of ventral spinal progenitor cells is at least 80% of the total cell population. In still other embodiments of the first aspect, the activator of the SHH pathway is purmorphamine.

In a second aspect, the present invention is summarized as a method of creating a population of spinal motor neurons from ESCs. In one embodiment of the second aspect, the method comprises the step of culturing the cells described above in a suspension culture with RA and SHH or an activator of the SHH pathway until the cells express HB9, HoxB1, HoxB6, HoxC5, HoxC8, ChAT and VAChT.

In some embodiments of the second aspect, the total time period to development of the spinal motor neurons is between three to four weeks. In other embodiments of the second aspect, the total population of spinal motor neurons and their progenitors is at least 80% of the total cell population. In still other embodiments of the second aspect, the activator of the SHH pathway is purmorphamine.

The present invention is also populations of cells created by these methods.

The present invention is also methods of testing the cell populations described above to screen agents for an ability to affect normal human neural development. In the methods, one would compare differentiation of cells exposed to the agent to cells not exposed to the agent. One would then examine whether the agents affected cell morphology (i.e., cause the exposed cells to transition to a more differentiated morphology), whether the agent affected cell surface marker expression (i.e., cause the exposed cells to express cell surface markers characteristic of differentiating cells) and even whether the agent affected cell viability, each of which can be readily ascertained by one of ordinary skill in the art.

Other objects, advantages and features of the present invention will become apparent after review of the specification, claims and drawings.

DETAILED DESCRIPTION OF THE SEVERAL VIEWS OF THE DRAWINGS

FIG. 1A-I. Differentiation and isolation of neural precursors from ES cells. (FIG. 1A) An attached EB grown in the presence of FGF2 for five days shows flattened cells at the periphery and small elongated cells congregated in the center. (FIG. 1B) By seven days, many rosette formations (arrows) appeared in the differentiating EB center. The upper-right inset is the 1-μm section of the rosette stained with toluidine blue, showing columnar cells arranged in a tubular structure. Bar=20 μm. (FIG. 1C-E) Cells in a cluster of rosettes (lower left) and a small forming rosette (center) are positive for nestin (FIG. 1C) and Musashi-1 (FIG. 1D) whereas the surrounding flat cells are negative. (FIG. 1E) A combined image of FIG. 1C and FIG. 1D with all cell nuclei labeled with DAPI. (FIG. 1F) After treatment with dispase for 20 minutes, the rosette formations retracted whereas the surrounding flat cells remained attached. (FIG. 1G-I) Isolated cells are positively stained for nestin in a filamentous pattern (FIG. 1G), Musashi-1 in cytoplasm (FIG. 1H), and PSA-NCAM mainly on membrane (FIG. 1I). All nuclei are stained with DAPI. Bar=100 μm.

Figure 2:
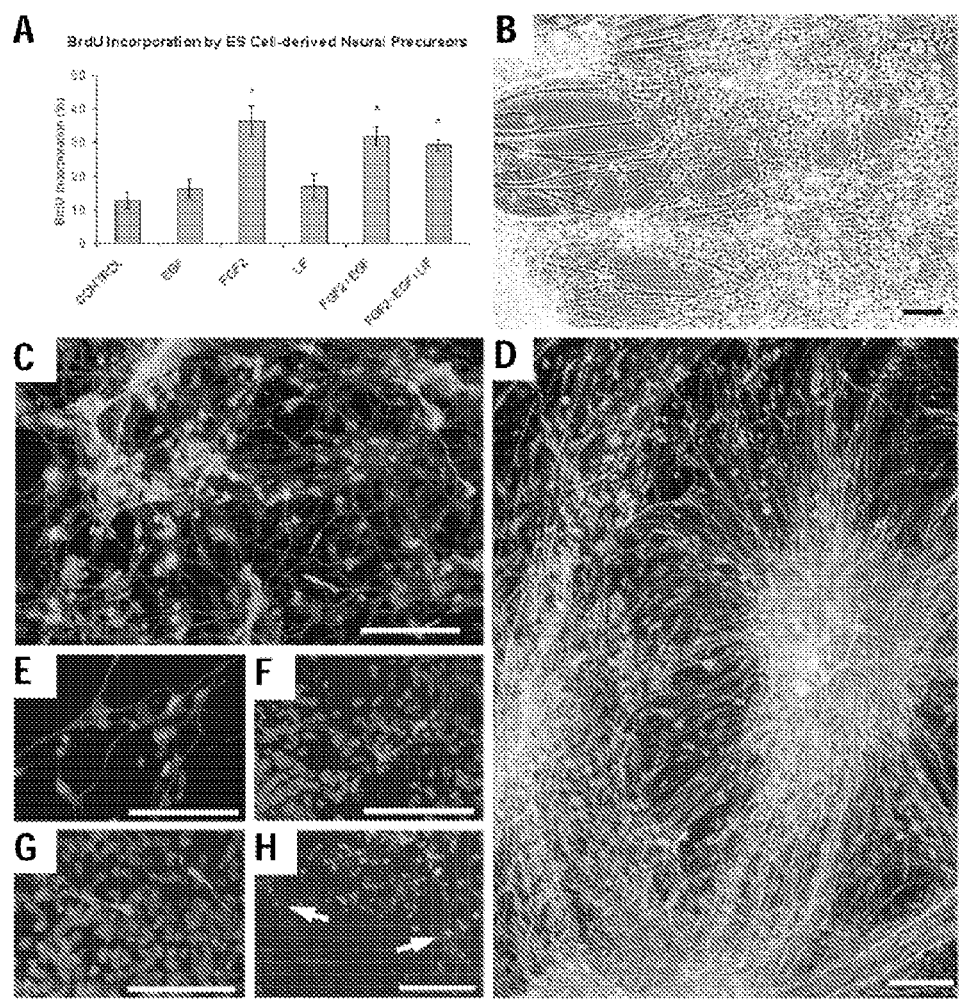

FIG. 2A-H. Characterization of ES cell-derived neural precursors in vitro. (FIG. 2A) BrdU incorporation by dissociated ES cell-derived neural precursors is elevated in the presence of FGF2 (20 ng/ml) but not with epidermal growth factor (EGF) (20 ng/ml) or leukemia inhibitory factor (LIF) (5 ng/ml). This is representative data from one of three replicate experiments. * indicates difference between the experimental group and the control group (p<0.01, n=4, student t-test). (FIG. 2B) Differentiation of a cluster of ES cell-derived neural precursors for three weeks shows neurite bundles with cells migrating along them. (FIG. 2C) Immunostaining after three weeks of differentiation indicates that the majority of cells are $\beta_{III}$-tubulin$^+$ neurons (red) and that only a few cells are GFAP$^+$ astrocytes (green). (FIG. 2D) After forty-five days of differentiation, many more GFAP$^+$ astrocytes (green) appear along with NF200$^+$ neurites (red, yellowish due to overlapping with green GFAP). (FIG. 2E-G) ES cell-derived neurons with various morphologies express distinct neurotransmitters such as glutamate (FIG. 2E), GABA (FIG. 2F) and the enzyme tyrosine hydroxylase (FIG. 2G). O4$^+$ oligodendrocytes (arrows) are observed after two weeks of differentiation in a glial differentiation medium (FIG. 2H). Bar=100 μm.

FIG. 3A-K. Incorporation and differentiation of ES cell-derived neural precursors in vivo. Grafted cells are detected by in situ hybridization with a probe to the human alu-repeat element (FIG. 3A-E, G) or an antibody to a human-specific nuclear antigen (FIG. 3F). (FIG. 3A) Individual donor cells in the host cortex of an eight-week-old recipient (arrows). (FIG. 3B) Extensive incorporation of ES cell-derived neural precursors in the hippocampal formation. Cells hybridized with the human alu probe are labeled with red dots (pseudo-colored). (FIG. 3C) Incorporated human cells in the vicinity of the hippocampal pyramidal layer at P14. (FIG. 3D) ES cell-derived cells in the septum of a four-week-old recipient mouse. (FIG. 3E) High power view of an individual donor cell in the hypothalamus. Note the seamless integration between adjacent unlabeled host cells. (FIG. 3F) Donor cells in the striatum of a four-week-old host, detected with an antibody to a human-specific nuclear antigen. (FIG. 3G) Extensive migration of transplanted cells from the aqueduct into the dorsal midbrain. (FIG. 3H) Human ES cell-derived neuron in the cortex of a two-week-old host, exhibiting a polar morphology and long processes. The cell is double labeled with antibodies to a human-specific nuclear marker (green) and $\beta_{III}$-tubulin (red). (FIG. 3I) Network of donor-derived axons in the fimbria of the hippocampus, identified with an antibody to human neurofilament. (FIG. 3J) Donor-derived multipolar neuron, double labeled with an antibody recognizing the a and b isoforms of MAP2. (FIG. 3K) ES cell-derived astrocyte in the cortex of a four-week-old animal, double labeled with the human-specific nuclear marker (green) and an antibody to GFAP (red). Note that all the double labelings are confocal images and are confirmed by single optical cuts. Bars: FIG. 3A, FIG. 3B, FIG. 3G 200 μm; FIG. 3C, FIG. 3D 100 μm; FIG. 3E, FIG. 3F, FIG. 3H-K 10 μm.

Figure 4:
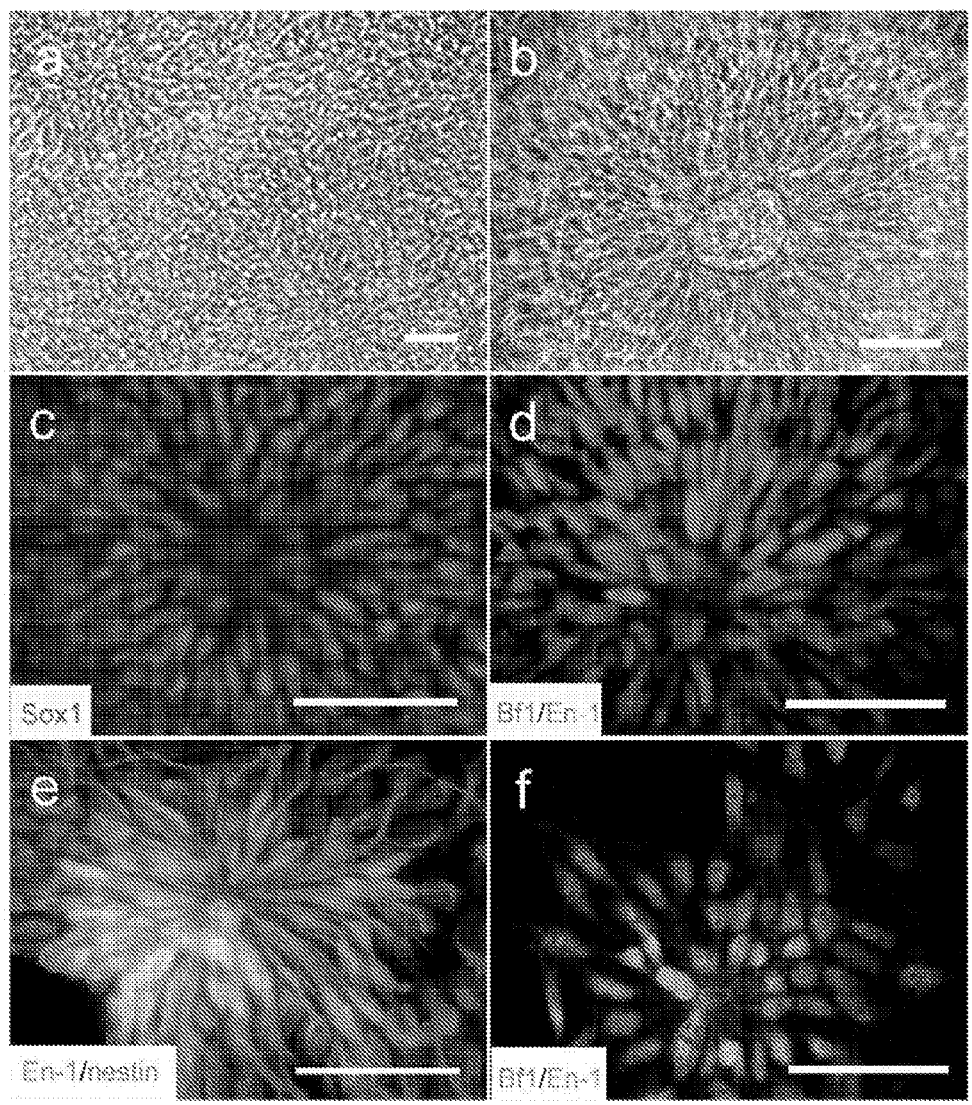

FIG. 4. Generation and regional specification of neuroectodermal cells. FIG. 4A. Columnar cells appeared in the differentiating ES cell colony at day nine in the presence of 20 ng/ml of FGF2. FIG. 4B. The columnar cells formed neural tube-like rosettes at day fourteen. FIG. 4C. The cells in the rosettes with columnar morphology were positive for Sox1 (red). FIG. 4D. The neural rosette cells in FGF2 treated cultures expressed Bf1 (red), but not En-1 (green). FIG. 4E. En-1 (green) expression was observed in the nestin$^+$ (red) neuroectodermal cells that were treated by six days with fibroblast growth factor 8 (FGF8) (100 ng/ml) at day nine, expanded in FGF8 for four days and then treated with sonic hedgehog (SHH) (200 ng/ml) for another six days on laminin substrate). FIG. 4F. These En-1$^+$ cells (green) were negative for Bf1 (red) in the culture treated as in FIG. 4E. The cell nuclei were stained with Hoechst (c, d; Blue). Bar=50 μm.

Figure 5:
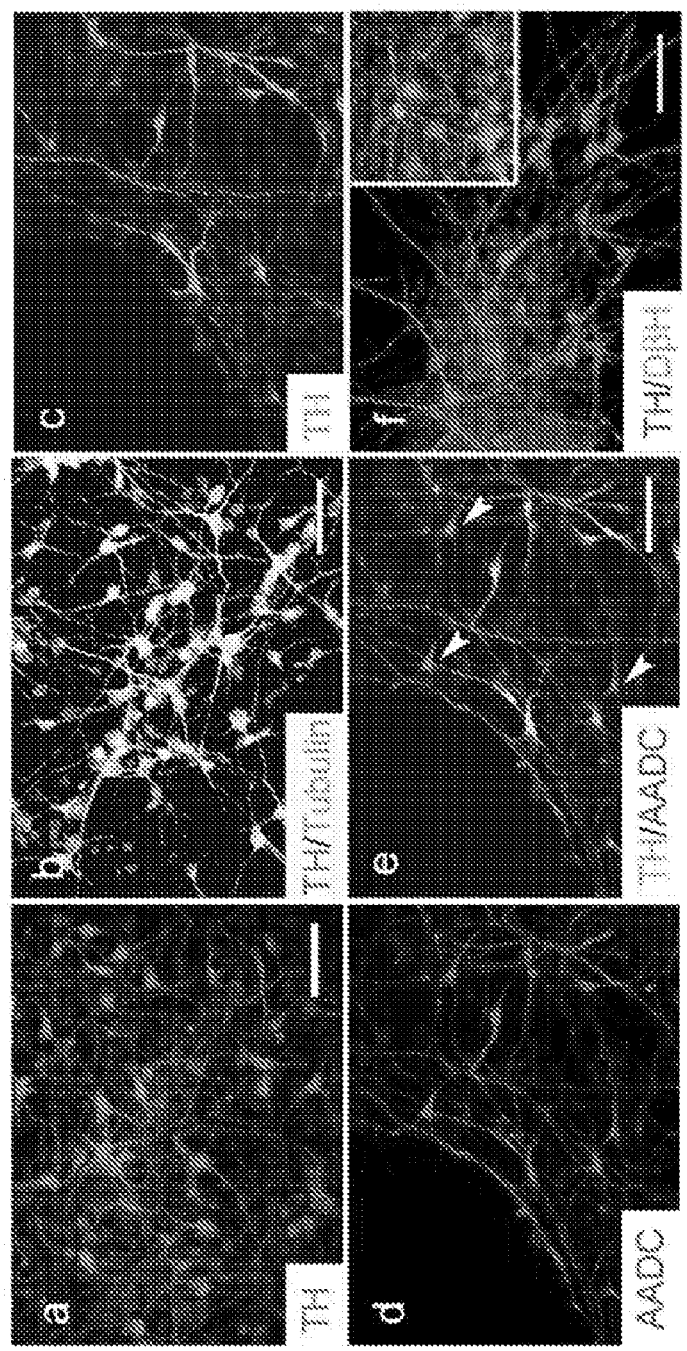

FIG. 5. Differentiation of DA neurons. FIG. 5A. About one third of the differentiated cells were tyrosine hydroxylase (TH) positive in the cultures that were treated with FGF8, SHH and ascorbic acid (M) at three weeks of differentiation. FIG. 5B. All TH$^+$ cells (red) in the culture were positively stained with a neuronal maker $\beta_{III}$-tubulin (green). FIG. 5C-E. All TH$^+$ cells (d, green) in the culture were positively stained with aromatic acid decarboxylase (AADC) (d and e, red), but some AADC$^+$ cells were TH$^-$ (e, arrowheads). FIG. 5F. The TH$^+$ cells were negative for noradrenergic neuron marker dopamine β-hydroxylase (DβH) (green). The inset indicated that DβH positively stained cells in the section of adult rat brain stem. The cell nuclei were stained with Hoechst (a, b, f; Blue). Bar=50 μm.

Figure 6:
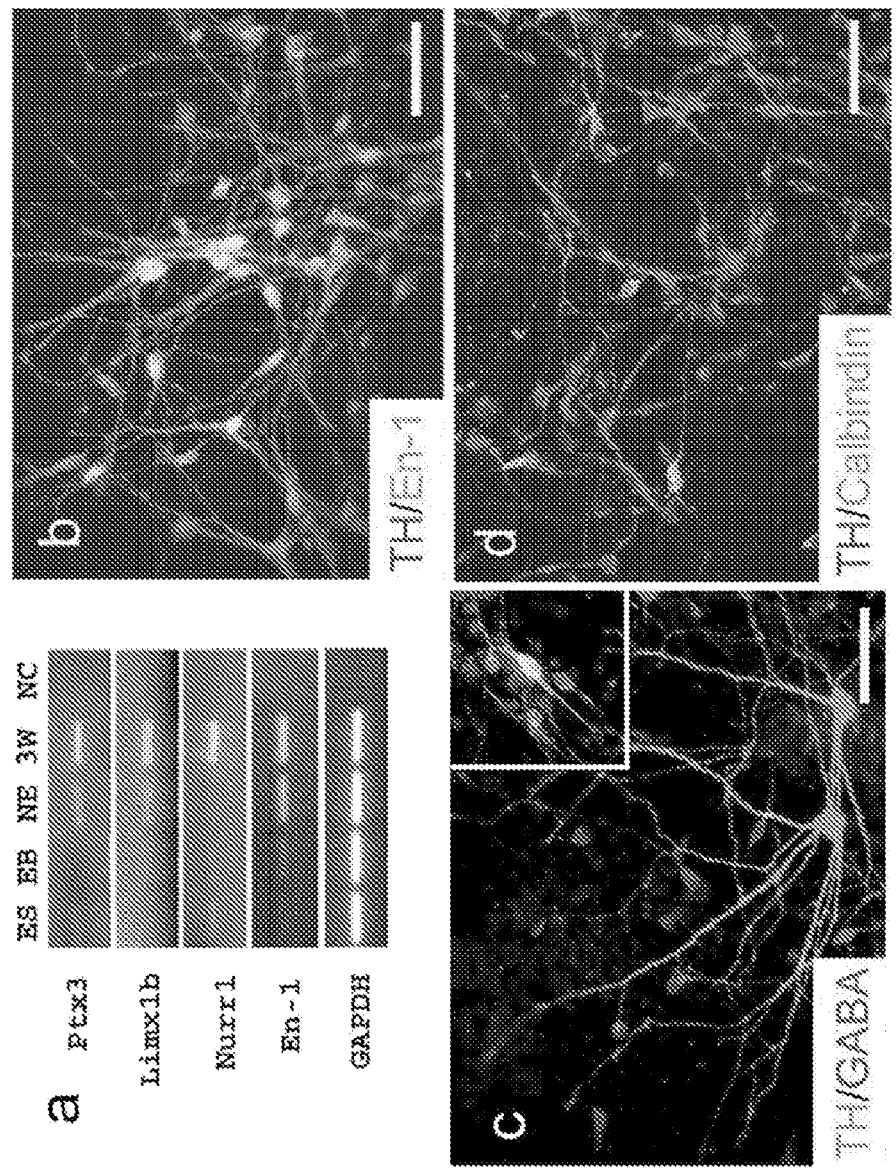

FIG. 6. Characterization of human ES cell-derived DA neurons. FIG. 6A. The differentiated DA neurons expressed genes characteristic of midbrain fate revealed by RT-PCR. EB: embryoid body; NE: neuroectodermal cells; 3w: the DA culture differentiated for three weeks; NC: negative control. FIG. 6B. The majority of TH$^+$ cells (red) in the cultures expressed midbrain marker En-1 (green). FIG. 6C. GABA expressing cells (red) were present in the culture but very few TH$^+$ cells (green) co-expressed GABA (red, inset). FIG. 6D. The TH$^+$ cells (red) were negative for calbindin (green). Bar=50 μm.

Figure 7:
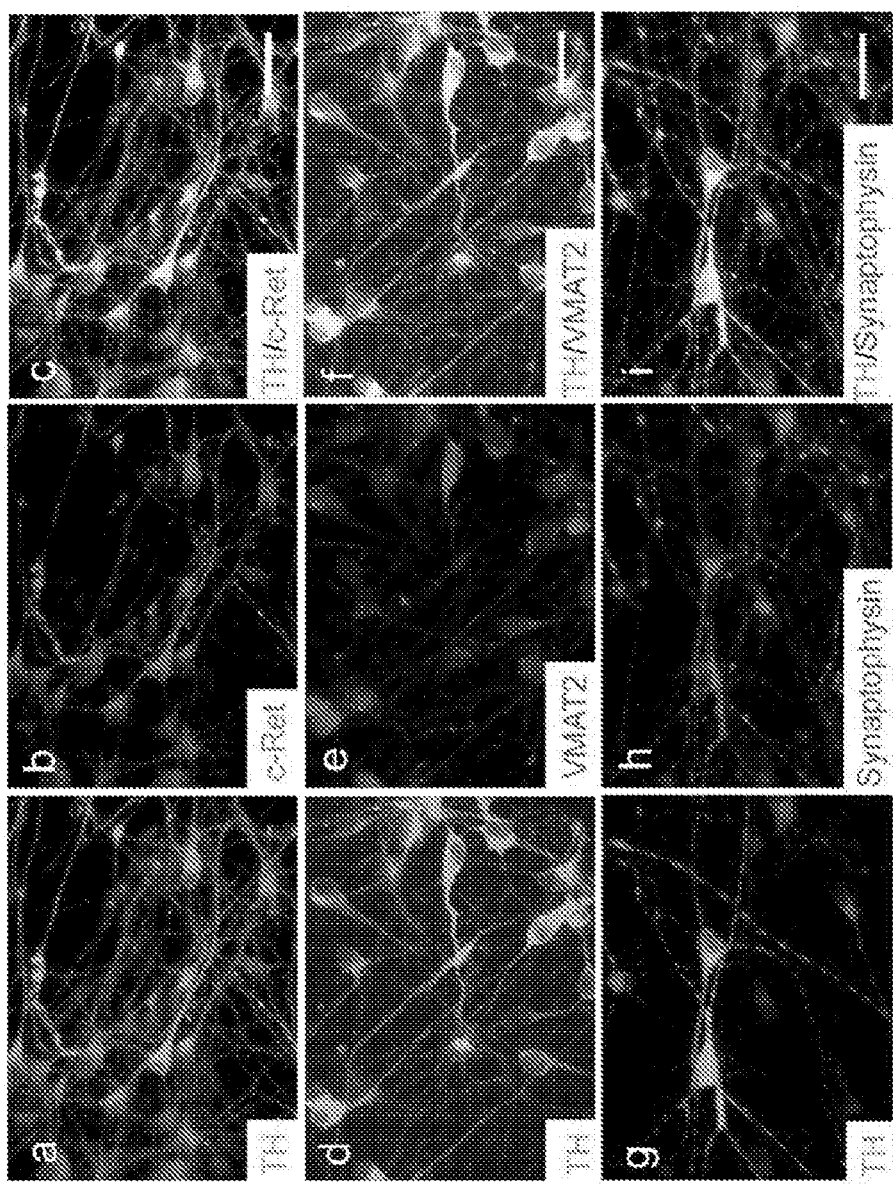

FIG. 7. Expression of receptors and transporters in the human ES cell-derived DA neurons. FIG. 7A-C. All TH$^+$ cells (a, green) expressed c-Ret (red). FIG. 7D-F. TH$^+$ cells (d, green) co-expressed VMAT2: (e and f; red). FIG. 7G-1. The TH$^+$ neurons (j, green) co-expressed synaptophysin (k and l, red). Bar=25 μm.

Figure 8:
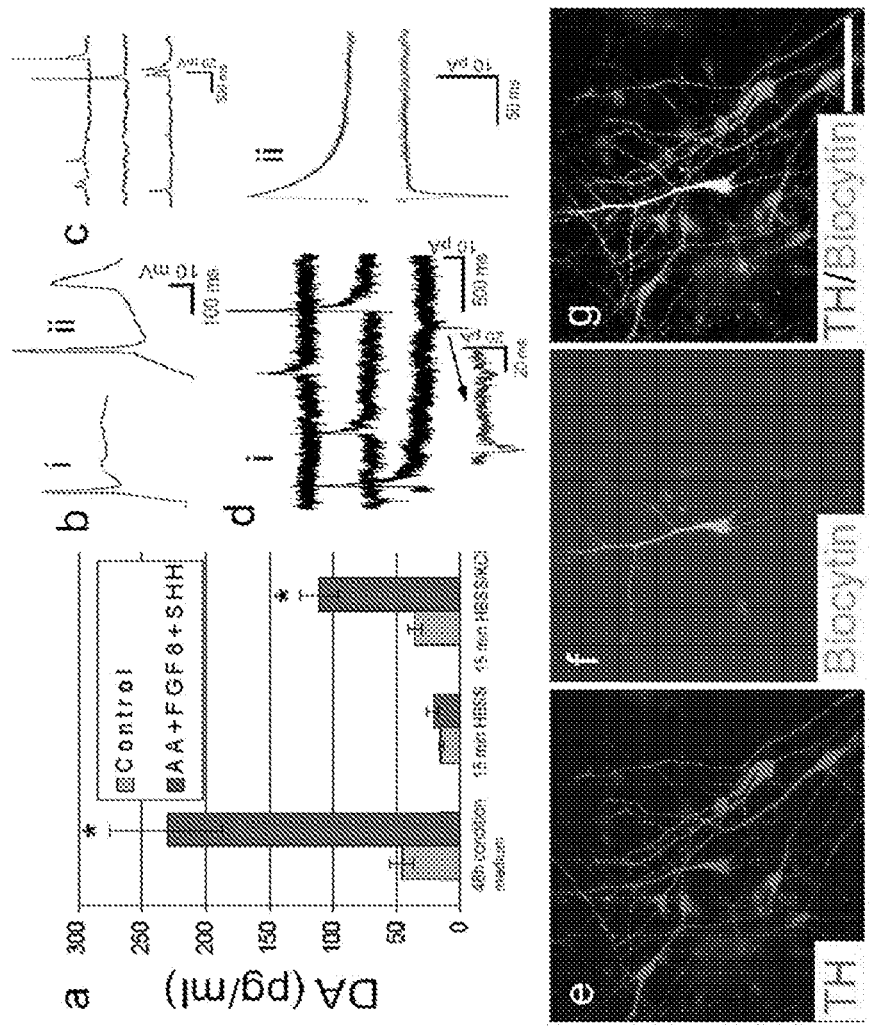

FIG. 8. Functional characteristics of the in vitro generated DA neurons. FIG. 8A. Spontaneous and depolarization (56 mM KCl in HBSS)-induced DA release in the control and the treated cultures at three weeks of differentiation. Data were presented as means ±SD from three experiments. *$p<0.05$ vs. control by the un-paired student t test. FIG. 8B. Action potentials evoked by depolarizing current steps (0.2 nA) in two neurons differentiated for thirty days. Passive membrane properties: (i) $V_{rest}$-49 mV, $C_m$ 15.5 pF, $R_m$ 5.0 GΩ; (ii) $V_{rest}$- 72 mV, $C_m$ 45 pF, $R_m$ 885 GΩ. FIG. 8C. Spontaneous postsynaptic potentials in a neuron differentiated for thirty-six days. FIG. 8D. Spontaneous postsynaptic currents in a neuron maintained for thirty days in culture. The neuron was voltage clamped at −40 mV using a K-gluconate-based pipette solution. The outward currents reflect inhibitory events and inward currents reflect excitatory events in this low chloride recording solution. (ii) Averaged events from the cell illustrated in panel (i). The weighted decay time constants are 61.4 ms and 9.9 ms for inhibitory (n=17 events) and excitatory (n=14 events) currents. FIG. 8E-G. Immunostaining showed that the recorded neuron (f, green) was TH$^+$ (e and g, red). Bar=50 µm.

Figure 9:
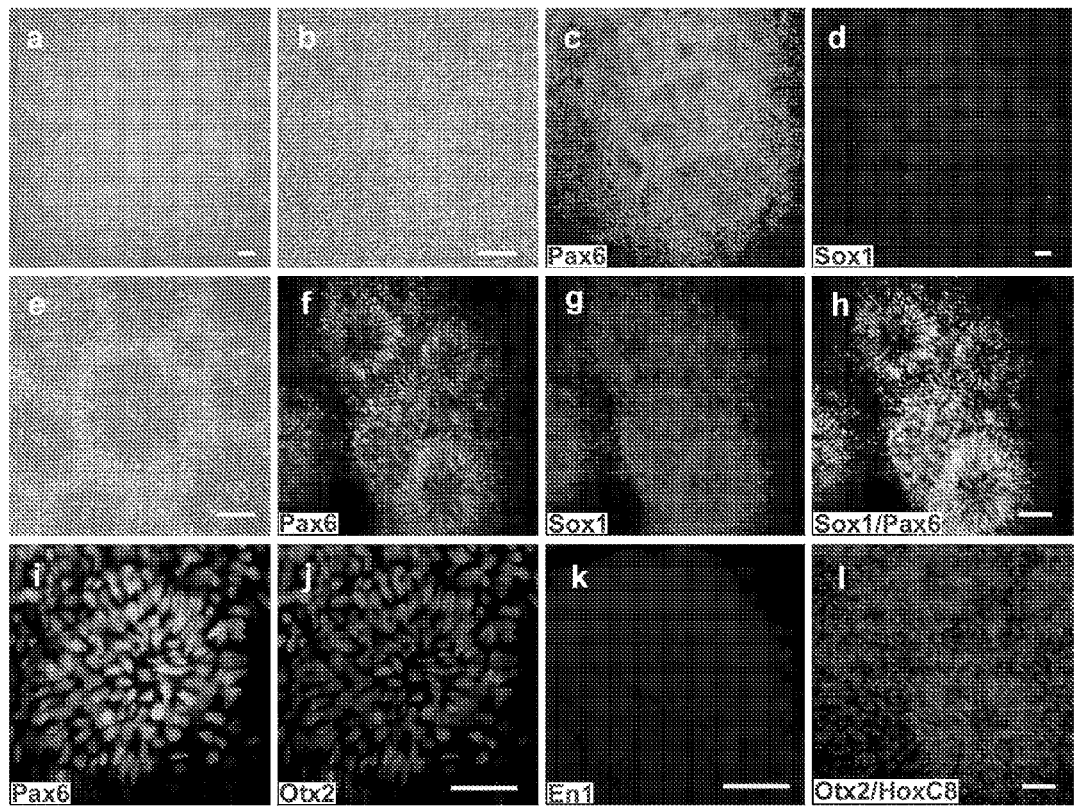

FIG. 9. Neuroectodermal cells induced by FGF2 display rostral phenotypes. ES cells, differentiated in FGF2 for ten days, displayed small, columnar morphology in the colony center, and organized into rosette formations (A, B). The columnar cells in the rosettes, but not the surrounding flat cells were positive for Pax6 and negative for Sox1 (C, D). By fourteen days, the columnar cells formed neural tube-like rosettes (E) and were positive for both Pax6 (F) and Sox1 (G, H). The Pax6$^+$ cells (I) in the rosettes were also Otx2$^+$ (J) but were En-1$^-$ (K). Cells in the neural tube-like rosettes were positive for Otx2 and negative for HoxC8 (L). Blue indicates Hoechst stained nuclei. Bar=50 µm.

Figure 10:
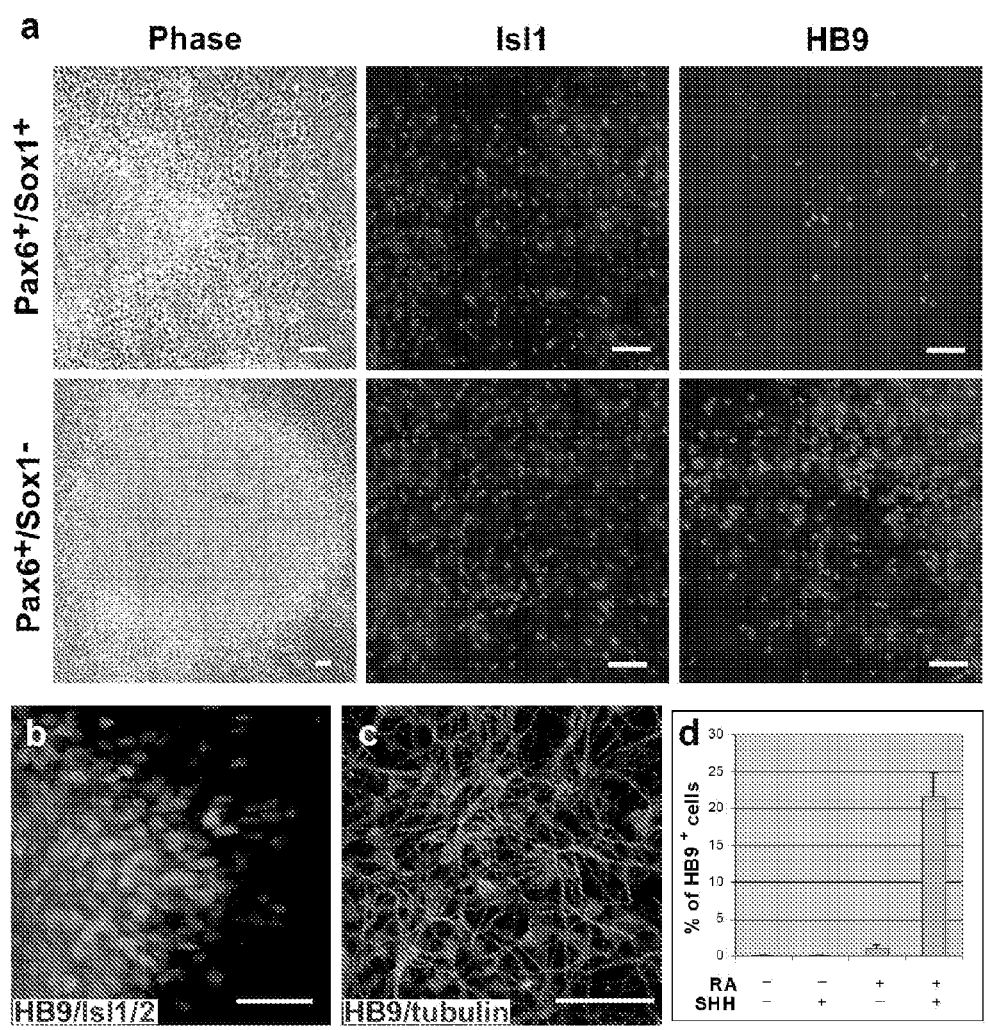

FIG. 10. Generation of motor neurons from neuroectodermal cells. (A) Differentiation of Sox1$^+$ neuroectodermal cells for two weeks (upper row) revealed extensive neuronal generation in the outgrowth area, expression of Isl1, but few HB9$^+$ cells. Treatment of Pax6$^+$/Sox1$^-$ neuroectodermal cells (2$^{nd}$ row) resulted in extensive neurite outgrowth with few migrating cells, expression of Isl 1, and a large proportion of HB9$^+$ cells. About 50% Isl½$^+$ differentiated from early neuroectodermal cells were also HB9$^+$ (B). HB9$^+$ cells were also positive for β$_{III}$-tubulin (C). About 21% of the cells in the cluster were HB9$^+$ when the cultures were differentiated in the presence of both retinoic acid (RA) and SHH, whereas few HB9$^+$ cells were observed when cultured in either RA alone, or SHH alone, or neither (D). Blue indicates Hoechst stained nuclei. Bar=50 µm.

Figure 11:
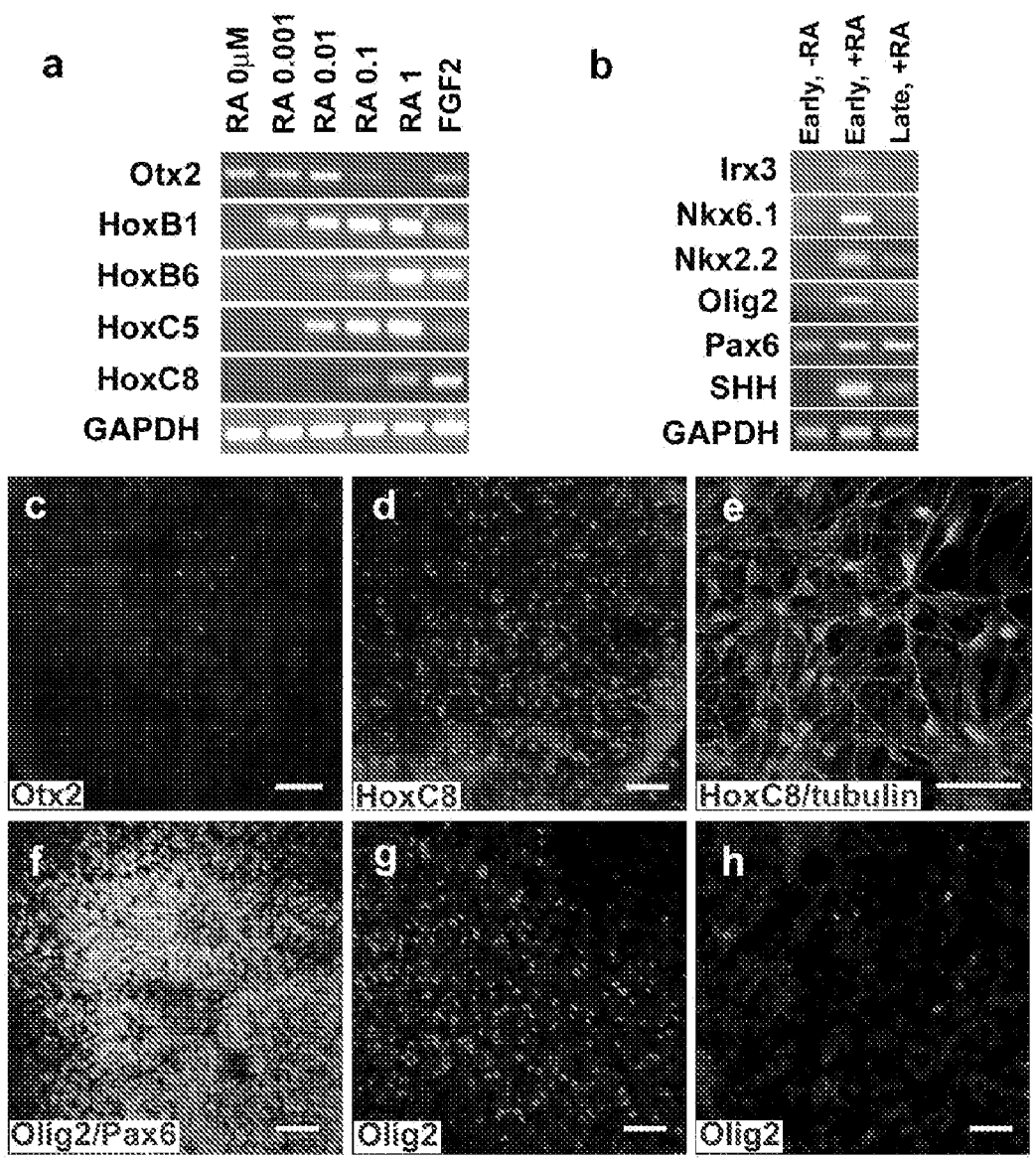

FIG. 11. Effect of RA, FGF2 and SHH on neuroectodermal cells. (A) RT-PCR analyses indicated changes of rostrocaudal genes from early rosettes cells that were cultured with RA or 20 ng/ml of FGF2 for one week in the neural induction medium. (B) Comparison of homeobox gene expression in early and late neuroectodermal cells treated with RA 0.1 µM for one week. The early neuroectodermal cells, treated with RA and then differentiated for twelve days, became mostly negative for Otx2 (C) but positive for HoxC8 (D). All the HoxC8$^+$ cells were β$_{III}$-tubulin$^+$ (E). The Pax6-expressing neuroectodermal cells were negative for Olig2 (F). After treatment with RA for one week and differentiation for two weeks in the presence of SHH (100 ng/ml), many cells expressed Olig2 (G). Few Olig2$^+$ cells were observed when late neuroectodermal cells were treated with RA and then differentiated under the same culture condition (H). Blue indicates Hoechst stained nuclei. Bar=50 µm.

Figure 12:
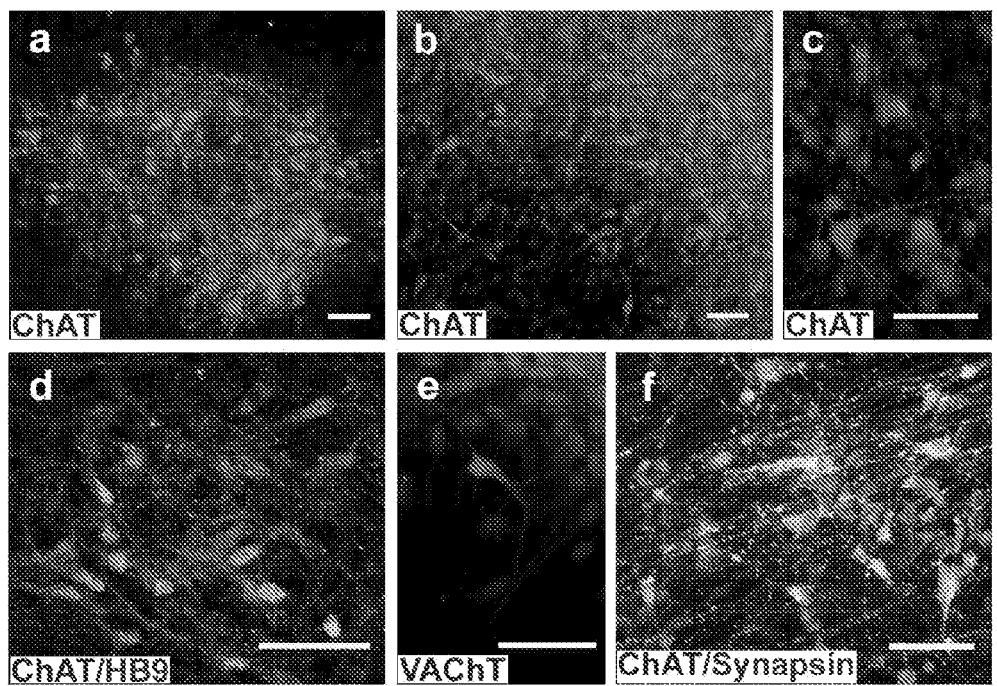

FIG. 12. Maturation of motor neurons in culture. ChAT-expressing cells were localized mainly in the cluster (A), and were large multipolar cells (B). Confocal image showed co-localization of ChAT in the soma and processes and HB9 in the nuclei in a three-week culture (C). Most cells in the cluster expressed VChAT (D). Many ChAT$^+$ cells were also positive for synapsin in somas and processes after five weeks in culture (E). (F) AP's evoked by depolarizing current steps (0.15 nA) in neurons maintained for 42 DIV. Resting membrane potential (Vm) −59 mV (fi) and −70 mV (fii).

Figure 13:
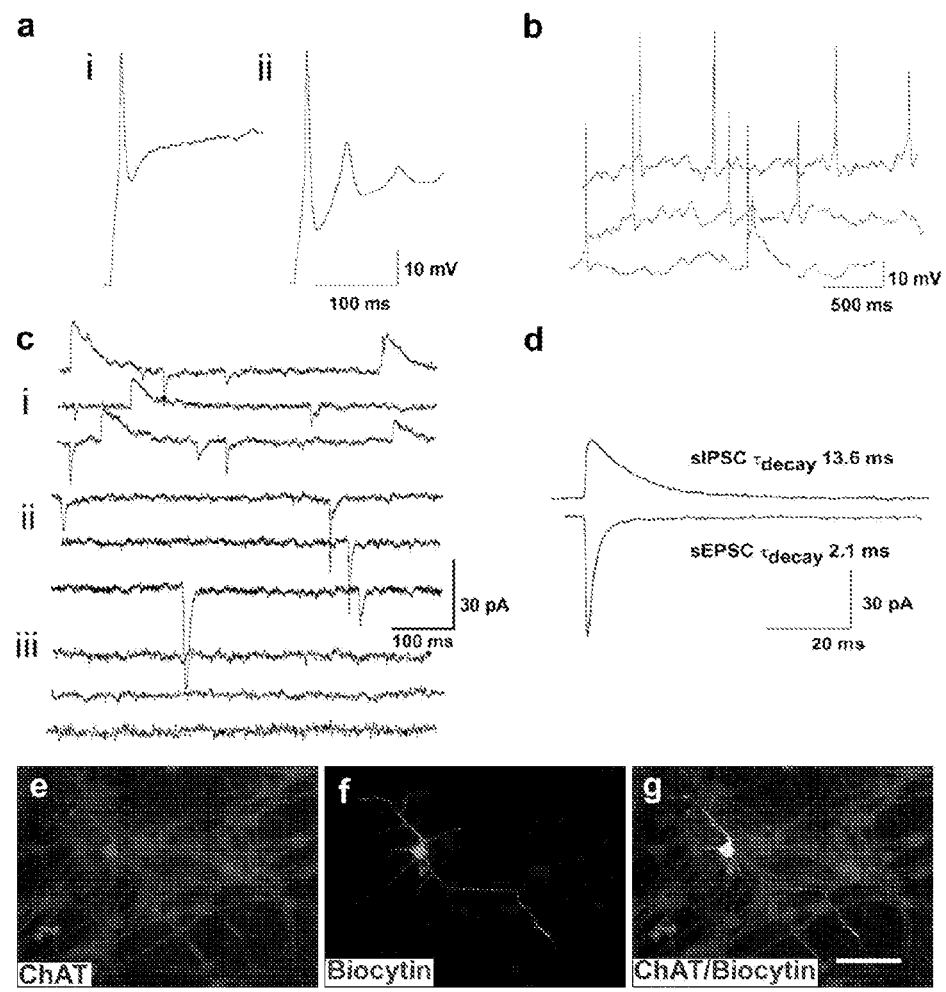

FIG. 13. Electrophysiological characterization of in vitro generated motoneurons. (A) AP's evoked by depolarizing current steps (0.15 nA) in neurons maintained for 42 DIV. Resting membrane potential (Vm) −59 mV (ai) and −70 mV (aii). (B) Spontaneous AP's in a neuron maintained for 42 DIV, Vm −50 mV. (C) Spontaneous inward and outward synaptic currents at −40 mV using K-gluconate-based pipette solution under control conditions (ci). Bath application of bicuculline (20 µM) and strychnine (5 µM) blocked outward currents (IPSCs, cii). Subsequent application of AP-5 (40 µM) and CNQX (20 µM) blocked the remaining inward currents (EPSCs, ciii). (D) Averaged sIPSCs and sEPSCs from the cell illustrated in panel c. (E-G) After recording, the coverslip cultures were immunostained with ChAT, showing that a biocytin-filled neuron was positive for ChAT. Bar=50 µm.

Figure 14:
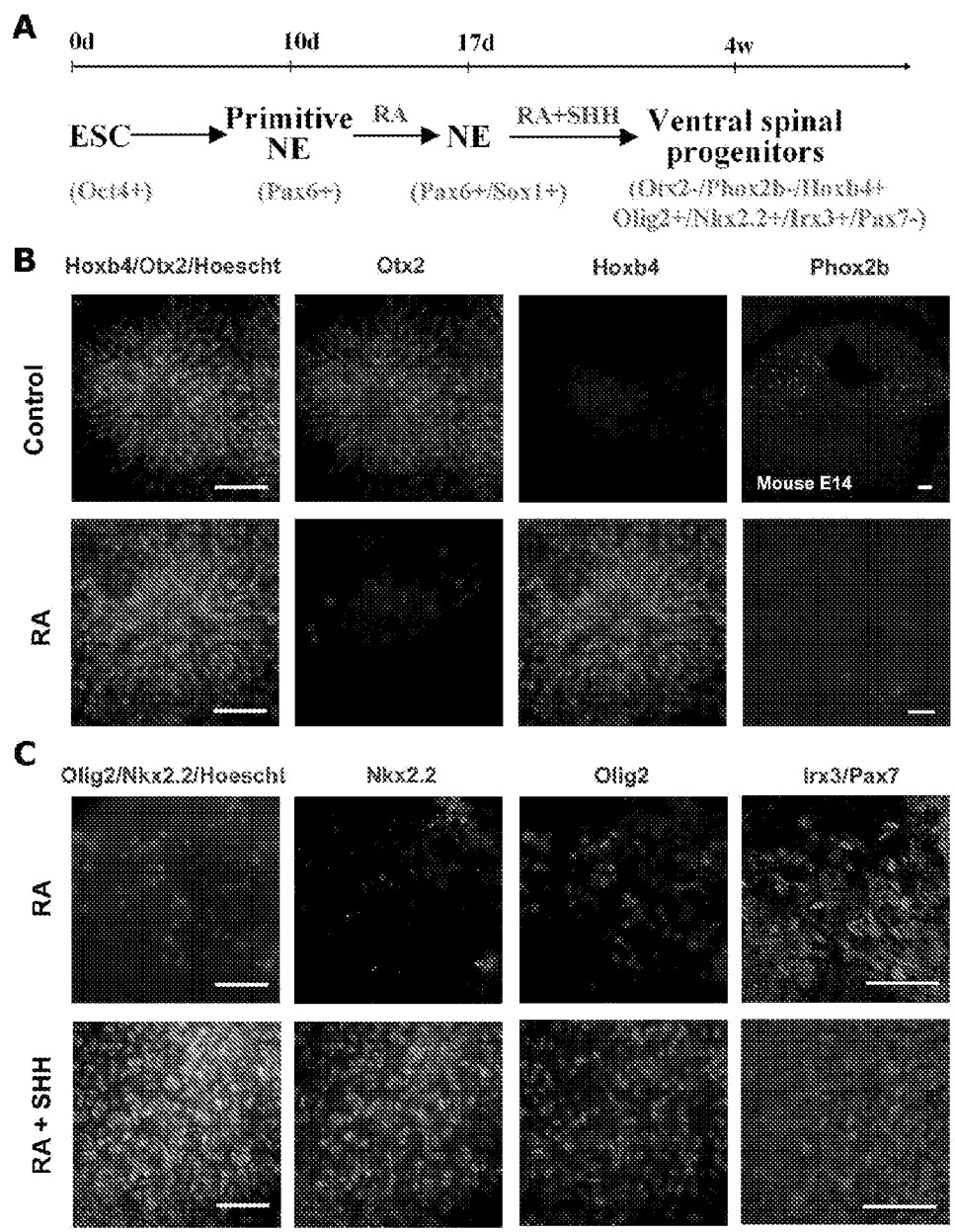

FIG. 14. Near complete specification of ventral spinal progenitors from hESCs in suspension culture. (A) Schematic procedure for ventral spinal progenitor differentiation. (B) Primitive NE (day 10), after treatment with RA for 1 week, were isolated and cultured in suspension without (control, first row) or with RA (second row) for another week (total 24 days). RA induced the expression of Hoxb4 but inhibited Otx2 expression. Very few cells expressed Phox2b in the RA-treated cultures. (C) Posteriorized neural progenitors (day 17) were cultured in the absence (upper row) or presence (lower row) of SHH and expression of transcriptional factors along the D-V axis was examined at day 28. In the absence of SHH, a small population of cells expressed Nkx2.2 and Olig2 whereas more cells were positive for Irx3, among which some also expressed Pax7. When SHH (100 ng/ml) was added (second row), a large portion of cells expressed Olig2 or Nkx2.2 whereas few cells were positive for Irx3+ and no cells were positively stained for Pax7 (second row). Blue indicates Hoechst stained nuclei. Bar=50 µm.

Figure 15:
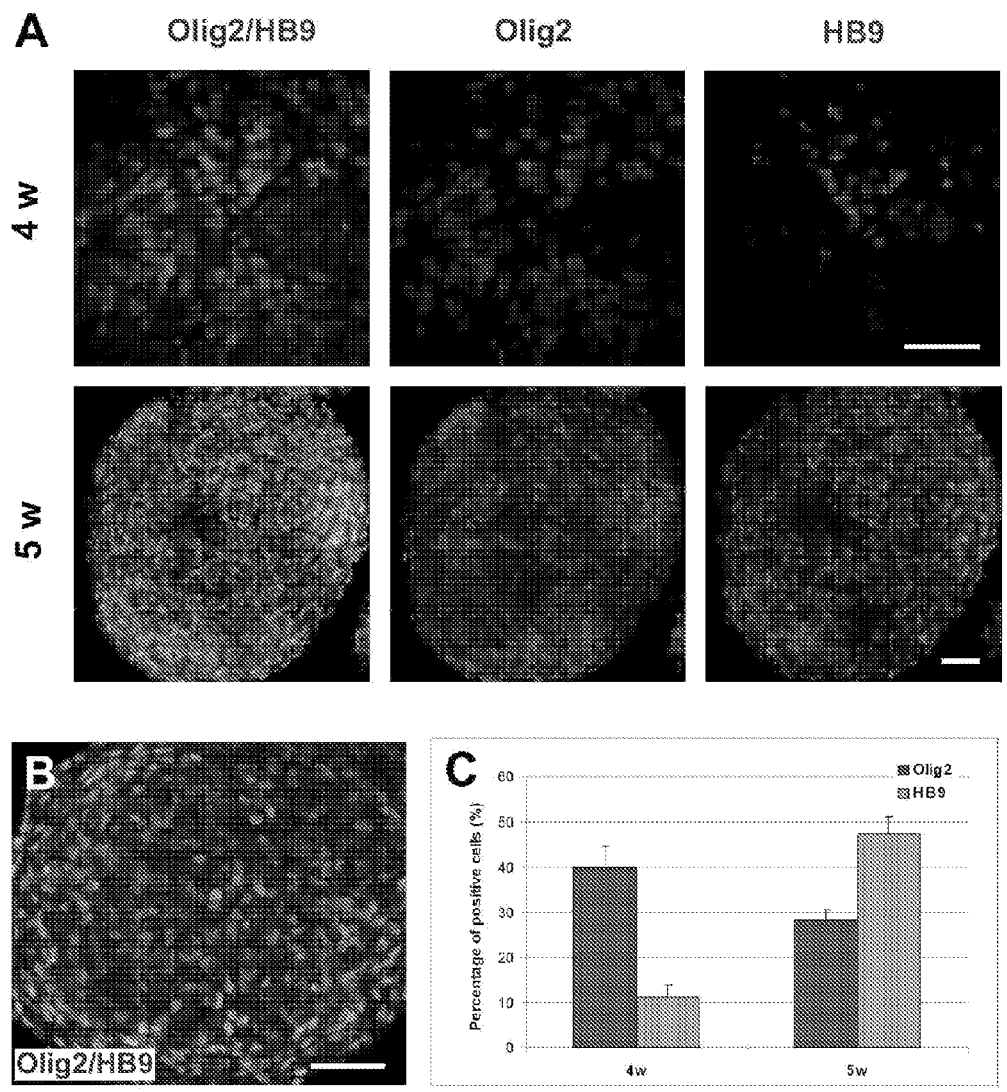

FIG. 15. Highly efficient generation of motoneurons in the continual presence of SHH. (A) Olig2+ motoneuron progenitors peaked at about 4 weeks after differentiation, when HB9+ postmitotic motoneurons increased and peaked at 5 weeks. (B) A confocal image showing the separation of most Olig2 and HB9 positive cells at 5 weeks after differentiation. (C) Diagram showing the change of population of Olig2+ and HB9+ cells at 4-5 weeks after differentiation. Data were presented as Mean +SEM. Blue indicates Hoechst stained nuclei. Bar=50 µm.

Figure 16:
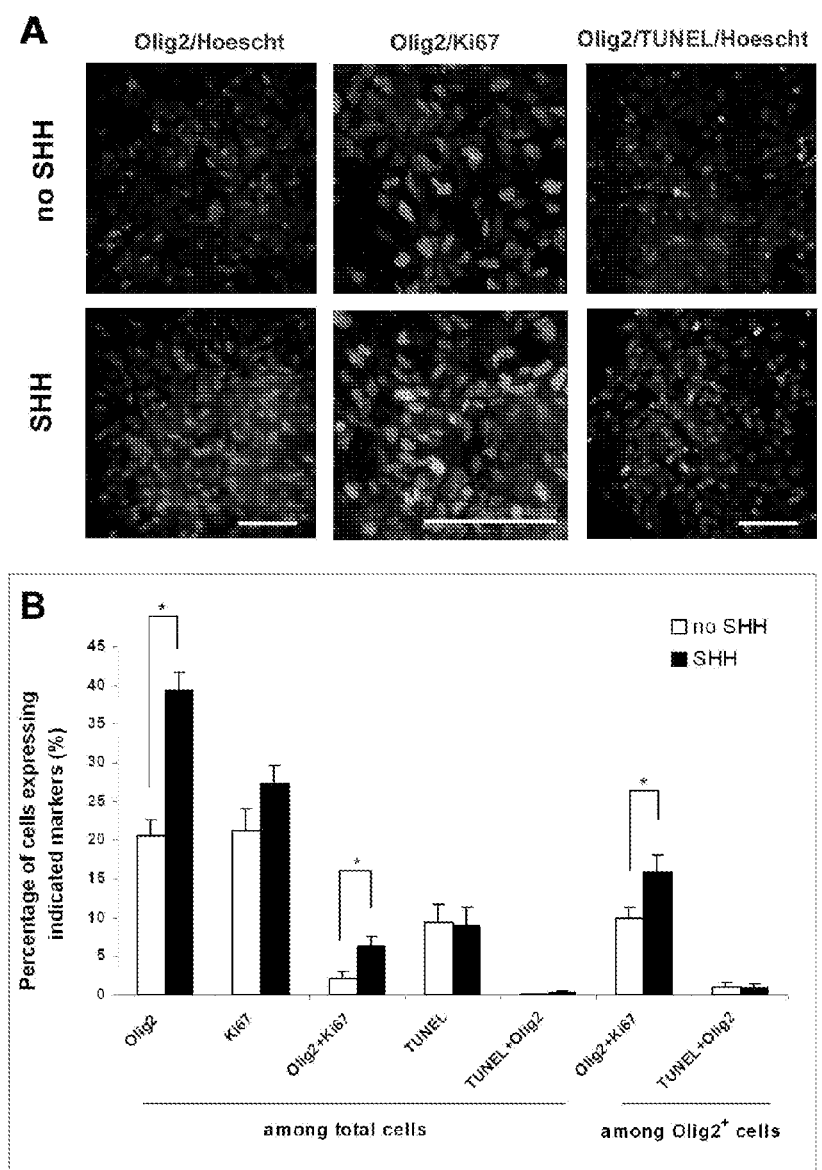

FIG. 16. SHH promotes proliferation of Olig2+ progenitors. (A) Olig2 enriched clusters were dissociated and plated on poly ornithine-laminin coated coverslips in the neural medium supplemented with B27 in the absence or presence of SHH (100 ng/ml) for 24 hours. More Olig2+ and Ki67+/Olig2+ cells were seen with SHH than without SHH. TUNEL staining showed no difference between the SHH and non-SHH groups. Blue indicates Hoechst stained nuclei. Bar=50 µm. (B) Quantitative analyses indicated that Olig2+, Ki67+/Olig2+ cells were more in the SHH-treated cultures than in the control cultures without SHH whereas Ki67+ and TUNEL+ cells in the total differentiated cells were similar between the SHH and non-SHH treated groups. Data were presented as Mean ±SEM. *, ANOVA test between SHH and non-SHH treated groups, P<0.05.

Figure 17:
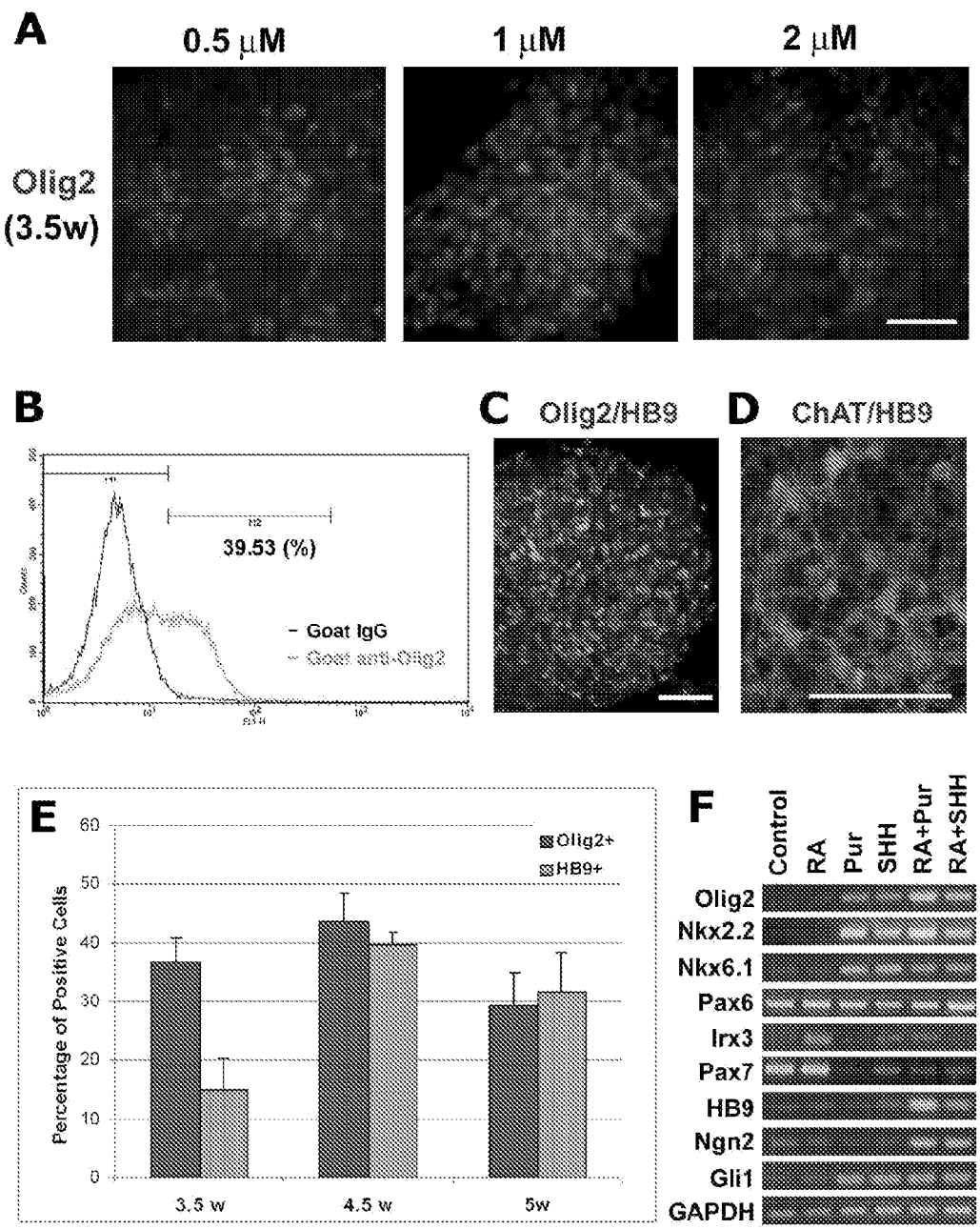

FIG. 17. Efficient generation of spinal progenitors and motor neurons by purmorphamine. (A) Caudalized NE (day 17) were treated with RA and different concentrations of purmorphamine. At 3.5 week after hESC differentiation, Olig2 was induced by purmorphamine in a dose-dependent manner. (B) Cell populations were quantified by FACS, as exemplified by Olig2-expressing cells in the purmorphamine (1 µM) group. (C) At 4.5 week, the expression of Olig2 and HB9 increased to over 40%. (D) After another week differentiation in adherent cultures, most HB9+ motoneurons also expressed ChAT. (E) Diagram showing time-dependent change of population of Olig2+ and HB9+ cells after differentiation. Mean ±SEM. (F) RT-PCR analyses indicated expression of transcriptional factors by caudalized NE that were cultured with RA (0.1 µM), purmorphamine, SHH or purmorphamine plus RA for 1 week (day 24). Blue indicates Hoechst stained nuclei. Bar=50 µm.

DETAILED DESCRIPTION OF PREFERRED EMBODIMENTS

Applicants herein disclose a method for generating dopamine (forebrain and midbrain) and motor neurons from hESCs. The preferred methods are generally described below and in Tables 1-3.

Specifically, Applicants disclose a method of differentiating early rosettes (Pax6+/Sox1−) from ESCs through an EB intermediate. By differential treatment, Applicants can differentiate these early rosettes into three different forms of neural tube-like rosettes that are then suitable for development into forebrain dopamine neurons, midbrain dopamine neurons or motor neurons.

TABLE 2

Generation of Dopamine and Motor Neurons from Human Embryonic Stem Cells

| Phase 1 | Propagation of embryonic stem cells and development of these cells into synchronized population of neural stem cells in the form of neural tube-like rosettes. |
| --- | --- |
| Phase 2 | Development of phase 1 cells through differential culture conditions into either forebrain dopamine neurons, midbrain dopamine neurons or motor neurons. |

As stated above, this invention includes two main embodiments. One embodiment is the procedure for generating a synchronized population of neural stem cells (or neuroepithelial cells) in the form of neural tube-like rosettes and expression of neuroepithelial markers Pax6, Sox1, nestin, Musashi-1. As used herein, "synchronize" means a population of cells that are at the same developmental stage, as opposed to those induced by RA which results in heterogeneous differentiation, i.e., the culture contains cells in developmental stages from progenitors to differentiated neurons. In the case here, we see either $Pax6^+/Sox1^-$ early neuroepithelial cells at an early stage or $Pax6^+/Sox1^+$ neuroepithelial cells at a later stage. In either stage, we do not see any differentiated neurons. This synchronized development will allow a directed differentiation toward a specialized neuronal fate, as described in this application.

The second embodiment is a method of further differentiation of the neuroepithelial cells to specialized neurons, such as midbrain dopamine neurons, forebrain dopamine neurons and spinal motor neurons.

Table 3 below, describes a preferred method of obtaining cells of the present invention. Table 3 includes both general culture broth components, that can be replaced by similar

TABLE 1

Generation of Dopamine and Motor Neurons from Human Embryonic Stem Cells

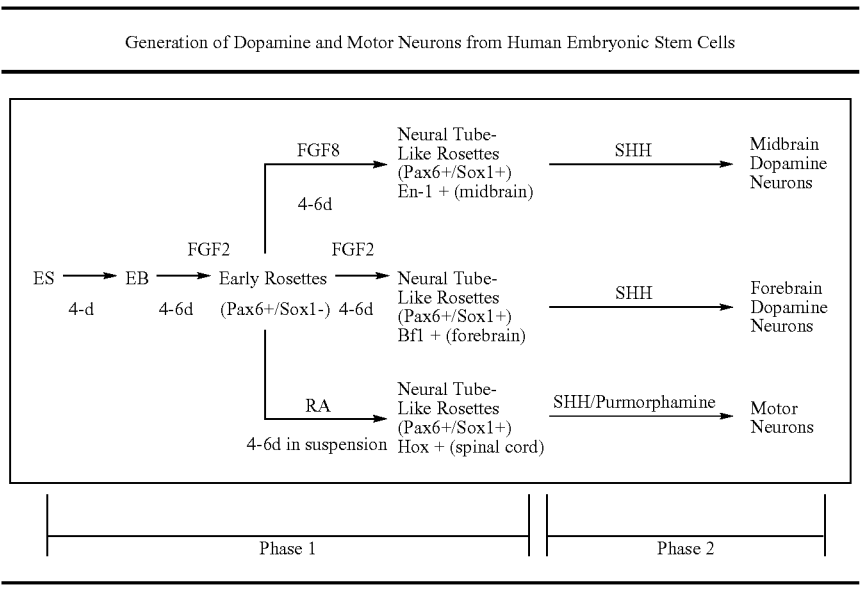

Applicants refer to Table 2 below, which describes Phases 1 and 2 for generating dopamine and motor neurons. Table 2 also describes various intermediate products that Applicants consider to be markers of suitable development.

culture broths, and critical growth factor and timing components. When Applicants refer to neural cell culture medium, many culture components are suitable. The sections below emphasize the culture components necessary for correct differentiation.

In general, a suitable medium is any medium used for growing neural cells. The following references (Bain et al., supra; Okabe et al., supra; Mujtaba et al., supra; Brustle et al., supra; Zhang S, et al., J. Neurosci. Res. 59:421-429 (2000); Zhang S, et al., Proc. Natl. Acad. Sci. USA-96:4089-4094 (1999); Svendsen C, et al., Exp. Neurol. 137:376-388 (1996); Carpenter M, et al., Exp. Neurol. 158:265-278 (1999); and Vescovi A, et al., Exp. Neurol. 156:71-83 (1999)) use the same or similar medias.

1. Differentiation of Neuroepithelial Cells (Neural Stem Cells) from hESCs

The generation of neuroepithelial cells involves formation of EBs in suspension culture for 4-6 days, followed by adherent culture in the presence of growth factors, preferably FGF2 or FGF8, for 4-5 days when cells in the center of each colony become columnar and organize into a rosette form (FIG. 1A, FIG. 4A, FIG. 9A, B). (See Zhang et al., Nature Biotechnol., 2001) FGF4 and FGF9 are also suitable growth factors.

The columnar cells in these rosettes express a neural transcription factor Pax6 but do not express another neural transcription factor Sox1 (FIG. 9C, D). We call these rosettes "early rosettes" because they appear early and form by monolayer of columnar cells without a lumen. Every single colony possesses early rosettes. The total population of early rosette cells is at least 70% of the total cells.

Further culture of these early rosettes for 4-6 days leads to formation of neural tube-like rosettes (FIG. 1B, FIG. 4B, FIG. 9E). The neural tube-like rosettes are formed by multiple layers of columnar cells with a clear lumen. The cells in the rosettes express Sox1 in addition to Pax6 (FIG. 4C, FIG. 9 F, G, H). The progression from early rosettes to neural tube-like rosettes takes about 4-6 days under our serum-free culture condition in the presence of FGF2, FGF4, FGF8, FGF9 at 10-20 ng/ml or RA at 0.001-1 µM.

The process of neuroepithelial differentiation, from ESCs to formation of neural tube-like rosettes, takes 14-16 days. hESCs are derived from a 5.5 day-old human embryo (Thomson et al., supra, 1998). Hence, the development of neuroepithelial cells from hESCs in our culture system compares well to the 19-21 days the development takes in a human embryo. In normal human development, neural tube forms at 20-21 days. Thus, neuroepithelial differentiation from hESCs mirrors normal human embryo development (Zhang S, J. Hematother. Stem Cell Res. 12:625-634 (2003)).

The two-stage neuroepithelial development, as evidenced by morphological transformation and clear-cut gene expression patterns has not been described before. Pax6 and Sox1 have been shown to be expressed by neuroepithelial cells when neural tube forms at the same time in frogs, zebrafish, chicks and mice (Pevny, et al., Development 125:1967-1978 (1998)). Hence, we believe the finding of sequential Pax6 and Sox1 expression along neuroepithelial differentiation in hESCs is novel and may be unique to humans. The Pax6+/Sox1− neuroepithelial cells represent the earliest neuroepithelial cells thus far identified. The functional significance of these cells is relevant to the present invention in that the Pax6+/Sox1− neuroepithelial cells in the early rosettes, but not the Pax6+/Sox1+ neuroepithelial cells in the neural tube-like rosettes, can be efficiently induced to become neurons carrying positional identities other than forebrain, such as midbrain dopamine neurons and spinal motor neurons (Table 1, see above).

Every differentiating ESC colony forms neural tube-like rosettes. The neuroepithelial cells represent at least 70-90% of the total differentiated cells.

The neuroepithelial cells in the form of neural tube-like rosettes can be purified through treatment with a low concentration of dispase and differential adhesion (described in U.S. Ser. No. 09/960,382).

2. Generation of Midbrain Dopamine Neurons

A functional neuron with potential therapeutic application must possess at least two additional characteristics in addition to being a neuron: (1) a specific positional identity and (2) a capacity to synthesize, release and uptake a neural transmitter.

The first step in generating midbrain dopamine neurons is the induction of a midbrain identity. Treatment of the Pax6+/Sox1− early rosette cells, but not the Pax6+/Sox1+ neural tube-like rosette cells, with FGF8 (50-200 ng/ml) for 6-7 days results in efficient differentiation of the cells to progenitors that express midbrain transcription factors Engrailed 1 (En-1) and Pax 2 (FIG. 4E, F) and down regulation of forebrain marker Bf-1 (FIG. 4D).

The second step is to culture the midbrain progenitors in the presence of sonic hedgehog (SHH, 50-250 ng/ml) for 6-7 days, then in the regular neuronal differentiation medium (such as that described in Table 3) for additional 2 weeks until dopamine neurons develop. Preferably, at least 35% of the total differentiated cells will become dopamine neurons.

A preferred differentiation medium is described in Table 3.

The dopamine neurons express TH, AADC, but not DbH and PNMT (FIG. 5) enabling the synthesis of dopamine but not the further metabolism to norepinephrine or nephrine.

The dopamine neurons express En-1, ptx3, Nurr1, and Lmx1b (FIG. 6A, B), transcription factors that are required for midbrain dopamine neuron development.

The dopamine neurons do not express GABA (FIG. 6C). Coexpression with GABA is the feature of dopamine neurons in the olfactory bulb.

The dopamine neurons do not express calbindin (FIG. 6D). Coexpression with calbindin is the feature of dopamine neurons in the tegamental area of the midbrain.

Together, the above features indicate that the dopamine neurons generated in our culture system are midbrain dopamine neurons, more closely resembling those in the substantial nigra, the dopamine neurons that are lost in Parkinson's disease.

The dopamine neurons possess c-ret, a receptor for GDNF (FIG. 7A, B, C), a growth factor required for survival and function of dopamine neurons.

The dopamine neurons also express VMAT2 (FIG. 7D, E, F), a transporter required for storage and release dopamine. They also express DAT (FIG. 7G, H, I), a transporter necessary for dopamine uptake after release. Thus, the dopamine neurons generated in our culture system possess necessary machinery for synthesis, storage, release, and uptake of the transmitter dopamine.

The dopamine neurons express synaptophysin (FIG. 7) for formation of synapses. They can fire action potentials and can secrete dopamine in response to stimulation (FIG. 8). Therefore, the dopamine neurons are functional. In fact, in vitro-generated human, dopamine neurons reverse locomotive functional deficit in a rodent model of Parkinson's disease following transplantation into a diseased brain.

3. Generation of Spinal Motor Neurons

The first step in generating spinal motor neurons is the induction of a spinal cord (caudal) identity. Treatment of the Pax6+/Sox1− early rosette cells, but not the Pax6+/Sox1+ neural tube-like rosette cells (FIG. 10A), with RA (0.001-1 uM) for 6-7 days results in efficient differentiation of the cells to progenitors that express spinal cord transcription factor Hox genes such as HoxB1, HoxB6, HoxC5, HoxC8, but not forebrain markers Otx2 and Bf-1 or midbrain marker En-1 (FIG. 11A, C, D, E).

The second step is to culture the spinal cord progenitors in the presence of sonic hedgehog (SHH, 50-250 ng/ml) for 6-7 days to induce a ventralized progenitor character, as evidenced by expression of Olig2, (FIG. 11F, G, H), a transcription factor expressed by only ventral neural progenitors, then in the regular neuronal differentiation medium for additional 7-10 days until spinal motor neurons develop. Alternatively, the spinal cord progenitors are cultured in the presence of a small molecule activator of the SHH pathway, such as purmorphamine.

A preferred differentiation medium is described in Table 3.

In a preferred embodiment, at least 50% of the total differentiated cells become spinal motor neurons. The motor neurons express HB9, islet½, and Lim3 (FIG. 10), transcription factors that are specifically expressed by spinal cord motor neurons. The motor neurons also express HoxB1, HoxB6, HoxC5, HoxC8, but not forebrain markers Otx2 and Bf-1 or midbrain marker En-1 (FIG. 11A, C, D, E), indicating that they are spinal motor neurons.

The motor neurons express ChAT (FIG. 12A, B, C, D), an enzyme necessary for synthesizing the motor neuron transmitter acetylcholine. The motor neurons also express VAChT (FIG. 12E), suggesting that the motor neuron can store and uptake the transmitter acetylcholine.

In addition, the motor neurons express synapsin (FIG. 12F) for formation of synapses. They can fire action potentials (FIG. 13). Therefore, the motor neurons are functional. We have data showing that the motor neurons make neuro-muscular junctions when co-cultured with skeletal muscle cells, as shown by staining with bungarotoxin for acetylcholine receptor and by electron microscopy.

4. Generation of Forebrain Neurons

In another embodiment, the present invention is a method of differentiating primate ESCs (preferably hESCs) into forebrain dopamine neurons, preferably transplantable neural precursors suitable for nervous system repair. One would preferably begin the method as described above for mid-brain dopamine neuron generation. To generate forebrain neurons, the Pax6$^+$/Sox1$^-$ cells are treated for an additional 4-6 days with FGF2 and are then treated with SHH. The steps in generating forebrain dopamine neurons and the analyses for determining the dopamine neuron characters are similar to those described for midbrain dopamine neurons. The main difference is the use of morphogens at a particular period and the features of dopamine neurons.

The first step in generating forebrain dopamine neurons is the induction of a forebrain identity. Treatment of the Pax6+/Sox1− early rosette cells with FGF2 (10-20 ng/ml) for 6-7 days results in efficient differentiation of the cells to progenitors that express forebrain transcription factors Bf-1 and Otx2.

The second step is to culture the forebrain progenitors in the presence of sonic hedgehog (SHH, 50-250 ng/ml) for 6-7 days, then in the regular neuronal differentiation medium for additional 2 weeks until dopamine neurons develop. 35% of the total differentiated cells become dopamine neurons. The description below, taken from U.S. patent application Ser. No. 09/970,382, describes a preferred method.

A primate ESC line, preferably a hESC line, is first obtained and propagated. One may obtain an ESC line as described in Thomson J, et al., Science 282:1145-1147 (1998) and U.S. Pat. Nos. 5,843,780 and 6,200,806 or by other methods suitable to obtain a ESC line with normal karyotypes and the ability to proliferate in an undifferentiated state after continuous culture for at least eleven months and preferably twelve months. The ESC line will also retain the ability, throughout the culture, to form trophoblasts and to differentiate into tissue derived from all three embryonic germ layers (endoderm, mesoderm and ectoderm).

The cells are then cultured. In a preferred embodiment of the present invention, the cells are propagated on a feeder layer of irradiated mammalian, preferably mouse, embryonic fibroblasts, preferably as disclosed below and in Thomson et al. 1998, supra, and U.S. Pat. Nos. 5,843,780 and 6,200,806. We also envision that the cells may be propagated without feeder cell layers.

The ESC colonies are typically removed intact from adherent cultures by treatment with dispase and grown in a suspension as free-floating ESC aggregates called EBs, preferably for four days as described below.

The EBs are then cultured in medium containing FGF2, preferably at 20 ng/ml, to generate early rosette cells. The other preferred components of the medium are as described in Table 3. However, many other medium components are suitable. In general, a suitable medium is any medium used for growing neural cells. The following references (Bain et al., supra; Okabe et al., supra; Mujtaba et al., supra; Brustle et al., supra; Zhang et al., J. Neurosci. Res., supra; Zhang et al., Proc. Natl. Acad. Sci. USA, supra; Svendsen et al., supra; Carpenter M, et al., Exp. Neurol. 158:265-278 (1999); Vescovi A, et al., Exp. Neurol. 156:71-83 (1999)) use the same or similar medium.

After approximately five days of culture in the medium, the plated EBs will generate an outgrowth of flattened cells and by seven days the center small elongated cells will generate rosette formations such as seen in FIG. 1B. These formations resemble the early neural tube (insert of FIG. 1B). One may confirm the presence of neural precursors by morphology or by immunofluorescence analysis using neural marker antigens such as nestin and Musashi I, as described below. Preferably, the neural precursors comprise at least 72%, and most preferably at least 84%, of the total cells.

One may wish to further isolate the neural tube-like rosettes, preferably by differential enzymatic treatment and adhesion, as described below in the Examples. In brief, treatment with dispase will lead to the preferential detachment of the central neuroepithelial islands. To separate the clusters of rosette cells from the surrounding flat cells, the differentiating EBs cultured for eight to ten days are preferably incubated with 0.1-0.2 mg/ml dispase (Gibco BRL, Lifetechnologies, Rockville, Md.) at 37° C. for 15-20 minutes. Alternatively, 0.2 mg/ml of dispase may be used. The rosette clumps retract whereas the surrounding flat cells remain adherent. At this point, the rosette clumps may be dislodged by swaying the flask, which leaves the flat cells adherent. The clumps are pelleted, gently triturated with a 5 ml pipette and plated into a culture flask for 30 minutes to allow the contaminating individual cells to adhere. The floating rosette clumps are then transferred to a new flask, preferably coated with poly-(2-hydroxyethyl-methacrylate) to prohibit attachment, and cultured in a medium used for human neural precursors with the presence of FGF2 (typically 20 ng/ml). As described below in the Examples, treatment with dispase followed by differential adhesion will yield a highly enriched population of neural precursor cells, typically at least 90% and most preferably at least 96%. Additionally, one may use other methods, such as immune separation using an antibody to PSA-NCAM, to separate the neural precursor cells.

The Examples below demonstrate the hESC-derived neural precursors can generate all three CNS cell-types in vitro.

The table below is a flow chart of various aspects of this embodiment of the present invention:

TABLE 4

Characterization of the Neural Precursor Cells in vitro and in vivo

| | |
|---|---|
| ES cells | Treatment with dispase and cultured in free-floating condition with ES medium without FGF2 for 4 days followed by chemically defined medium with FGF2 (10-20 ng/ml) for 2 days. |
| ⇩ | |
| Embryoid Bodies | Adherent culture in a chemically defined medium containing FGF2 for 7-9 days. |
| ⇩ | |
| Differentiation to Neural tube-like structures | These are unique structures representative of neural epithelial cells as defined by histology and immunohistochemistry. Neural precursor cells typically comprise at least 72-84% of the total cells. |
| ⇩ | |
| Isolation of Neural Precursor Cells with Dispase Treatment | Treatment with dispase followed by differential adhesion yields a highly enriched population of neural precursor cells (preferably at least 95%). |

In another embodiment, the present invention is a cell population comprising at least 72%, and preferably 84%, neural precursor cells. These neural precursor cells can be defined by being nestin and Musashi I positive. FIG. 1B illustrates the rosette formation characterizing these cells. By rosette formation, we mean that cells are columnar in shape and are arranged in a tubular (rosette) structure, resembling the neural tube (developing brain) in the body. The columnar cell morphology and tubular structures are shown in the insert of FIG. 1B.

In another embodiment, the present invention is a cell population of at least 90% and preferably at least 96% neural precursor cells. One would preferably obtain these cells after differential enzymatic treatment and adhesion, as described below in the Examples.

5. Use of Cell Populations of the Present Invention

Generation of specialized human neuronal cell types with specific transmitter phenotypes and unique positional identities provide a source of transplantable cells for treatment in neurological disorders, such as midbrain dopamine neurons for Parkinson's disease, forebrain dopamine neurons for psychological diseases, spinal motor neurons for spinal cord injury and motor neuron diseases including ALS.

Establishment of stepwise and chemically defined culture systems for directed differentiation of hESCs first to neuroepithelial cells and then to specialized neurons also offers an unprecedented system for screening toxic and therapeutic agents. At the present, toxicological and therapeutic drug screenings are performed using animals, animal cell cultures, or genetically abnormal human cell lines. hESCs and their differentiation to specialized neuronal cells represent a normal process of human neural development. Hence, the invention described herein will be amenable to screen agents that affect normal human neural development or those that potentially result in abnormal brain development, as well as those that may stimulate regeneration of the neuronal types in diseased conditions. In addition, the described system can be readily modified to mimic pathological processes that lead to death of dopamine neurons (such as in Parkinson's disease) or motor neurons (such as in ALS), which may be effectively used to screen therapeutic agents that are designed to treat these diseases.

In a preferred method of this embodiment of the present invention, one would expose one of the cell populations of the present invention to a test compound and compare the results of such exposure to a control cell population that has not been exposed. One could understand whether a particular test compound affected the cell population by examining characteristics of the culture and comparing them to known developmental characteristics contained within the present application.

TABLE 3A

Neuroepithelial (Neural Stem) Cells - Preferred Culture Conditions and Markers

| Phase | Cell Name | Cell-Specific Marker | Culture Media Constituents | Culture Media Conditions | Electrophysiological Markers |
|---|---|---|---|---|---|
| Phase 1 | ES | Oct4+, SSEA4+ Pax6−, Sox1− | Irradiated mouse fibroblast; DMDM/F12 (1:1); 20% serum replacer; 2 μg/ml heparin; 0.1 mM β-mercaptoethanol; 4 ng/ml FGF2 | media changed every day; 36.5° C., 5% $CO_2$ | N/A |
| Phase 1 | 1$^{st}$ Dispase Treatment | N/A | 1-2 mg/ml dispase | 30 minutes; 37° C.; ambient atmosphere | N/A |
| Phase 1 | EB | Oct4+, SSEA4+ Pax 6−, Sox 1− | Suspension culture, no mouse fibroblast; DMDM/F12 (1:1); 20% serum replacer; 2 μg/ml heparin; 0.1 mM β-mercaptoethanol; NO FGF2 | 4 days; media changed every day; 25-$cm^2$ tissue culture flask; 36.5° C., 5% $CO_2$ | N/A |
| Phase 1 | EB | Oct4+, SSEA4+ Pax 6− Sox 1− | Suspension culture, no mouse fibroblast; DMEM/F12 (1:1); 25 μg/ml insulin; 100 μg/ml transferrin; 20 nM progesterone; 60 μM putrescine; 30 nM sodium selenite; 10-20 ng/ml FGF2 | 2 days; media changed every day; 25-$cm^2$ tissue culture flask; 36.5° C., 5% $CO_2$ | N/A |
| Phase 1 | Early Rosettes | Oct4−, SSEA4− Pax 6+, Sox 1− nestin+ PSA-NCAM− | DMEM/F12 (1:1); 25 μg/ml insulin; 100 μg/ml transferrin; 20 nM progesterone; 60 μM putrescine; 30 nM sodium selenite; 10-20 ng/ml FGF2 | 5 days; media changed every 2 days; 25-$cm^2$ tissue culture flask; 36.5° C., 5% $CO_2$ | N/A |

TABLE 3A-continued

Neuroepithelial (Neural Stem) Cells - Preferred Culture Conditions and Markers

| Phase | Cell Name | Cell-Specific Marker | Culture Media Constituents | Culture Media Conditions | Electro-physiological Markers |
|---|---|---|---|---|---|
| Phase 1 | Neural-like Tube Rosettes | Pax 6+, Sox 1+ Nestin+, Bf-1+ | DMEM/F12 (1:1); 25 µg/ml insulin; 100 µg/ml transferrin; 20 nM progesterone; 60 nM putrescine; 30 nM sodium selenite; 10-20 ng/ml FGF2 | 3-5 days; media changed every 2 days; 25-cm$^2$ tissue culture flask; 36.5° C., 5% CO$_2$ | N/A |
| Phase 1 | 2$^{nd}$ Dispase Treatment | N/A | 0.1-0.2 mg/ml dispase | 15-20 minutes; 36.5° C.; ambient atmosphere | N/A |

TABLE 3B

Midbrain Dopamine Neurons - Preferred Culture Conditions and Markers

| Phase | Cell Name | Cell-Specific Marker | Culture Media Constituents | Culture Media Conditions | Electro-physiological Markers |
|---|---|---|---|---|---|
| Phase 1 | ES | Oct4+, SSEA4+ Pax6−, Sox1− | Irradiated mouse fibroblast; DMDM/F12 (1:1); 20% serum replacer; 2 µg/ml heparin; 0.1 mM β-mercaptoethanol; 4 ng/ml FGF2 | media changed every day; 36.5° C., 5% CO$_2$ | N/A |
| Phase 1 | ES (1$^{st}$ Dispase Treatment) | N/A | 1-2 mg/ml dispase | 30 minutes; 37° C.; ambient atmosphere | N/A |
| Phase 1 | EB | Oct4+, SSEA44 Pax 6− Sox 1− | Suspension culture, no mouse fibroblast; DMDM/F12 (1:1); 20% serum replacer; 2 µg/ml heparin; 0.1 mM β-mercaptoethanol; NO FGF2 | 4 days; media changed every day; 25-cm$^2$ tissue culture flask; 36.5° C., 5% CO$_2$ | N/A |
| Phase 1 | EB | Oct4+, SSEA4+ Pax 6−Sox 1− | Suspension culture, no mouse fibroblast; DMEM/F12 (1:1); N2 supplement; 2 ng/ml heparin; 10-20 ng/ml FGF2 | 2 days; media changed every day; 25-cm$^2$ tissue culture flask; 36.5° C., 5% CO$_2$ | N/A |
| Phase 1 | Early Rosettes | Oct4−, SSEA4− Pax 6+, Sox 1− nestin+ PSA-NCAM− | DMEM/F12 (1:1); N2 supplement; 2 ng/ml heparin, 10-20 ng/ml FGF2 | 5 days; media changed every 2 days; 25-cm$^2$ tissue culture flask; 36.5° C., 5% CO$_2$ | N/A |
| Phase 2 | Neural-like Tube Rosettes | Pax 6+, Sox 1+ Nestin+, En1+, Pax2+ | DMEM/F12 (1:1); N2 supplement; 2 ng/ml heparin; 10-200 ng/ml FGF8 | 5-6 days; media changed every 2 days; 25-cm$^2$ tissue culture flask; 36.5° C., 5% CO$_2$ | N/A |
| Phase 2 | Neural epithelial cells (2$^{nd}$ Dispase Treatment) | N/A | 0.1-0.2 mg/ml dispase | 15-20 minutes; 36.5° C.; ambient atmosphere | N/A |
| Phase 2 | Expansion of neuroepithelial cells | Pax 6+, Sox 1+ Nestin+, En1+, Pax2+ | DMEM/F12 (1:1); N2 supplement; 2 ng/ml heparin; 10-200 ng/ml FGF8 + 50-250 ng/ml SHH | 5-6 days; media changed every 2 days; 25-cm$^2$ tissue culture flask; 36.5° C., 5% CO$_2$ | N/A |
| Phase 2 | 1$^{st}$ dissociation | N/A | N/A | Accutase (Gibco) | N//A |
| Phase 2 | Midbrain DA neurons | TH+, AADC+, DbH−, PNMT−, En1+, Bf-1−, Nurr1+, ptx3+, Lmx1b+, VMAT+, DAT+, c-ret+, GABA−, Calbindin−, CCK−, | Neurobasal medium; N2; 0.1 mM non-essential amino acids; 0.5 mM glutamine; 1 µg/ml laminin; 1 µM cAMP; 200 µM ascorbic acid; 10 ng/ml BDGF; 10 ng/ml GDNF | 2-3 weeks; media changed every 2 days; culture Petri dishes; 36.5° C., 5% CO$_2$ | Secretion of DA, Action potentials. |

TABLE 3C

Spinal Motor Neurons - Preferred Culture Conditions and Markers

| Phase | Cell Name | Cell-Specific Marker | Culture Media Constituents | Culture Media Conditions | Electro-physiological Markers |
|---|---|---|---|---|---|
| Phase 1 | ES | Oct4+, SSEA4+ Pax6−, Sox1− | Irradiated mouse fibroblast; DMDM/F12 (1:1); 20% serum replacer; 2 µg/ml heparin; 0.1 mM β-mercaptoethanol; 4 ng/ml FGF2 | media changed every day; 36.5° C., 5% CO$_2$ | N/A |
| Phase 1 | ES (1$^{st}$ Dispase Treatment) | N/A | 1-2 mg/ml dispase | 30 minutes; 37° C.; ambient atmosphere | N/A |
| Phase 1 | EB | Oct4+, SSEA4+ Pax 6−, Sox 1− | Suspension culture, no mouse fibroblast; DMDM/F12 (1:1); 20% serum replacer; 2 µg/ml | 4 days; media changed every day; 25-cm$^2$ | N/A |

TABLE 3C-continued

Spinal Motor Neurons - Preferred Culture Conditions and Markers

| Phase | Cell Name | Cell-Specific Marker | Culture Media Constituents | Culture Media Conditions | Electro-physiological Markers |
|---|---|---|---|---|---|
| | | | heparin; 0.1 mM β-mercaptoethanol; NO FGF2 | tissue culture flask; 36.5° C., 5% $CO_2$ | |
| Phase 1 | EB | Oct4+, SSEA4+ Pax 6−, Sox 1− | Suspension culture, no mouse fibroblast; DMEM/F12 (1:1); N2 supplement; 2 µg/ml heparin; 10-20 ng/ml FGF2 | 2 days; media changed every day; 25-cm$^2$ tissue culture flask; 36.5° C., 5% $CO_2$ | N/A |
| Phase 1 | Early Rosettes | Oct4−, SSEA4− Pax 6+, Sox 1− nestin+ PSA-NCAM− | DMEM/F12 (1:1); N2 supplement; 2 µg/ml heparin, 0.01-1 M RA | 5 days; media changed every 2 days; 25-cm$^2$ tissue culture flask; 36.5° C., 5% $CO_2$ | N/A |
| Phase 2 | Neural Tube-Like Rosettes | Pax 6+, Sox 1+ Nestin+, HoxB+, Olig2+, Otx2−, Bf1−, En1− | Suspension culture, DMEM/F12 (1:1); N2 supplement; 2 ng/ml heparin; 0.01-1 M RA; 10-500 ng/ml SHH (alternatively, purmorphamine 0.5-2 µM) | 5-6 days; media changed every 2 days; 25-cm$^2$ tissue culture flask; 36.5° C., 5% $CO_2$ | N/A |
| Phase 2 | Neural epithelial cells (2$^{nd}$ Dispase Treatment) | N/A | 0.1-0.2 mg/ml dispase | 15-20 minutes; 37° C.; ambient atmosphere | N/A |
| Phase 2 | Expansion of neuroepithelial cells | Pax 6+, Sox 1+ Nestin+, HoxC+, HoxB+, Olig2+, Otx2−, Bf1−, En1− | Suspension culture, DMEM/F12 (1:1); N2 supplement, 2 ng/ml heparin; 0.01-1 M RA + 50-250 ng/ml SHH (alternatively purmorphamine 0.5-2 µM) | 5-6 days; media changed every 2 days; 25-cm$^2$ tissue culture flask; 36.5° C., 5% $CO_2$. | N/A |
| Phase 2 | 1$^{st}$ dissociation | N/A | N/A | Accutase (Gibco) | N//A |
| Phase 2 | Spinal Motor neurons | HB9+, Islet+, Lim3+, HoxC+, ChAT+, VAChAT+, | Neurobasal medium; N2; 0.1 mM non-essential amino acids; 0.5 mM glutamine; 1 µg/ml laminin; 50 ng/ml SHH; 10 ng/ml BDNF, 10 ng/ml GDNF, 10 ng/ml IGF1 | 2-3 weeks; media changed every 2 days; culture Petri dishes; 36.5° C., 5% $CO_2$ | Action potentials. |

TABLE 3D

Forebrain Dopamine Neurons - Preferred Culture Conditions and Markers

| Phase | Cell Name | Cell-Specific Marker | Culture Media Constituents | Culture Media Conditions | Electro-physiological Markers |
|---|---|---|---|---|---|
| Phase 1 | ES | Oct4+, SSEA4+ Pax6−, Sox1− | Irradiated mouse fibroblast; DMDM/F12 (1:1); 20% serum replacer; 2 µg/ml heparin; 0.1 mM β-mercaptoethanol; 4 ng/ml FGF2 | media changed every day; 36.5° C., 5% $CO_2$ | N/A |
| Phase 1 | ES (1$^{st}$ Dispase Treatment) | N/A | 1-2 mg/ml dispase | 30 minutes; 37° C.; ambient atmosphere | N/A |
| Phase 1 | EB | Oct4+, SSEA4+ Pax 6− Sox 1− | Suspension culture, no mouse fibroblast; DMDM/F12 (1:1); 20% serum replacer; 2 µg/ml heparin; 0.1 mM β-mercaptoethanol; NO FGF2 | 4 days; media changed every day; 25-cm$^2$ tissue culture flask; 36.5° C., 5% $CO_2$ | N/A |
| Phase 1 | EB | Oct4+, SSEA4+ Pax 6− Sox 1− | Suspension culture, no mouse fibroblast; DMEM/F12 (1:1); N2 supplement; 2 ng/ml heparin; 10-20 ng/ml FGF2 | 2 days; media changed every day; 25-cm$^2$ tissue culture flask; 36.5° C., 5% $CO_2$ | N/A |
| Phase 1 | Early Rosettes | Oct4−, SSEA4− Pax 6+, Sox 1− nestin+ PSA-NCAM− | DMEM/F12 (1:1); N2 supplement; 2 ng/ml heparin, 10-20 ng/ml FGF2 | 5 days; media changed every 2 days; 25-cm$^2$ tissue culture flask; 36.5° C., 5% $CO_2$ | N/A |
| Phase 2 | Neural-like Tube Rosettes | Bf-1+, Otx2+ Nestin+, En1+, Pax2+ | 10-20 ng/ml FGF2 | 5-6 days; media changed every 2 days; 25-cm$^2$ tissue culture flask; 36.5° C., 5% $CO_2$ | N/A |
| Phase 2 | Neural epithelial cells (2$^{nd}$ Dispase Treatment) | N/A | 0.1-0.2 mg/ml dispase | 15-20 minutes; 36.5° C.; ambient atmosphere | N/A |
| Phase 2 | Expansion of neuroepithelial cells | Bf-1+, Otx2+ | DMEM/F12 (1:1); N2 supplement; 2 ng/ml heparin; 10-200 ng/ml FGF8 + 50-250 ng/ml SHH | 5-6 days; media changed every 2 days; 25-cm$^2$ tissue culture flask; 36.5° C., 5% $CO_2$ | N/A |
| Phase 2 | 1$^{st}$ dissociation | N/A | N/A | Accutase (Gibco) | N//A |

TABLE 3D-continued

Forebrain Dopamine Neurons - Preferred Culture Conditions and Markers

| Phase | Cell Name | Cell-Specific Marker | Culture Media Constituents | Culture Media Conditions | Electro-physiological Markers |
|---|---|---|---|---|---|
| Phase 2 | Forebrain DA neurons | TH+, AADC+, DbH−, PNMT−, Bf-1+, Otx2+, c-ret+, GABA+ | Neurobasal medium; N2; 0.1 mM non-essential amino acids; 0.5 mM glutamine; 1 μg/ml laminin; 1 μM cAMP; 200 μM ascorbic acid; 10 ng/ml BDGF; 10 ng/ml GDNF | 2-3 weeks; media changed every 2 days; culture Petri dishes; 36.5° C., 5% $CO_2$ | Secretion of DA, Action potentials. |

EXAMPLES

Examples 1-3 are from U.S. Ser. No. 10/928,805, filed Aug. 27, 2004 and are presented here as context for new Example 4, which discloses an improved method of preparing motor neurons.

Example 1

Generation of Forebrain Dopaminergic Neurons

Results hESCs differentiate to form neural tube-like structures in the presence of FGF2. hESC lines, H1, H9 and a clonal line derived from H9, H9.2 (Amit et al., supra) were propagated on a feeder layer of irradiated mouse embryonic fibroblasts (Thomson et al., supra, 1998). To initiate differentiation, ESC colonies were detached and grown in suspension as EBs for four days. The EBs were then cultured in a tissue culture treated flask in a chemically defined medium (Zhang et al., J. Neurosci. Res., supra; Zhang et al., Proc. Natl. Acad. Sci. USA, supra) containing FGF2. FGF2 was obtained from Peprotech, Inc., Rocky Hill, N.J. After five days of culture in FGF2, the plated EBs had generated an outgrowth of flattened cells. At the same time, an increasing number of small elongated cells was noted in the center of the differentiating EBs (FIG. 1A). By seven days in the defined medium, the central, small, elongated cells had generated rosette formations (FIG. 1B) resembling the early neural tube as shown by toluidine blue-stained sections (inset in FIG. 1B). Immunofluorescence analyses revealed that the expression of neural marker antigens nestin and Musashi-1 (Lendahl U. et al., Cell 60:585-595 (1990); Kaneko Y, et al., Dev. Neurosci. 22:139-153 (2000)), was largely restricted to cells in the rosettes but not the flat cells in the periphery of the differentiating EBs (FIG. 1C-E). Undifferentiated ESCs were immunonegative for these markers. The formation of neural tube-like structures was noted in the majority of EBs in the presence of FGF2 (94% of the total 350 EBs from H9 and H9.2 lines, 3 separate experiments). In the absence of FGF2, no well organized rosettes were observed.

Neural tube-like rosettes can be isolated by differential enzymatic treatment and adhesion. With continued exposure to FGF2, the columnar rosette cells expanded and formed multiple layers. They frequently made up most of the EB and were sharply demarcated from the surrounding flat cells. Treatment with dispase led to the preferential detachment of the central neuroepithelial islands, leaving the surrounding cells largely adherent (FIG. 1F). Contaminating single cells were separated by short-term adhesion to cell culture dishes. Cell counts performed immediately after this isolation and enrichment procedure showed that cells associated with the isolated neuroepithelial clusters made up 72~84% of the cells in the differentiated EB cultures. Immunocytochemical analyses showed that 96±0.6% of the isolated rosette cells were positively stained for nestin based on 13,324 cells examined in four separate experiments. The vast majority of these cells were also positive for Musashi-1 and PSA-NCAM (FIG. 1G, H, 1).

hESC-derived neural precursors generate all three CNS cell types in vitro. The isolated neural precursors were expanded as free-floating cell aggregates in a suspension culture, similar to "neurosphere" cultures derived from human fetal brain tissues (Zhang et al., supra, 2000; Svendsen et al., supra; Carpenter et al., supra; Vescovi et al., supra). BrdU incorporation studies revealed that stimulation of precursor cell proliferation was dependent on FGF2 and could not be elicited by either EGF or LIF alone. Furthermore, no additive or synergistic effects were observed when FGF2 was combined with EGF and/or LIF (FIG. 2A).

In vitro differentiation of the ESC-derived neural precursors was induced by withdrawal of FGF2 and plating on ornithine and laminin substrate. Within a few days, individual cells and numerous growth cones grew out from the spheres, giving a star burst appearance. By seven to ten days after plating, processes emanating from the spheres had formed prominent fiber bundles. Frequently, small migrating cells were seen in close association with the fibers (FIG. 2B). Immunofluorescence analyses of the differentiated cultures revealed that the vast majority of cells in the outgrowth areas expressed neuronal markers MAP2ab and $β_{III}$-tubulin (FIG. 2C). Expression of low molecular weight neurofilament (NF) and high molecular weight NF was observed by seven to ten and ten to fourteen days after plating, respectively (FIG. 2D). Antibodies to various neurotransmitters were used to further characterize the ESC-derived neurons. While the majority of the neurons exhibited a glutamatergic phenotype (FIG. 2E), a smaller proportion was labeled with an antibody to GABA. Frequently, these neurons showed a polar morphology (FIG. 2F). A small number of neurons were found to express TH (FIG. 2G), the rate-limiting enzyme for dopamine synthesis. $GFAP^+$ astrocytes were rarely found within the first two weeks after growth factor withdrawal (FIG. 2C), but became more frequent after prolonged in vitro differentiation. By four weeks, they had formed an extensive layer underneath the differentiated neurons (FIG. 2D). While oligodendrocytes were not observed under standard culture conditions, a few O4-immunoreactive cells with typical oligodendrocyte morphology were observed when the cells were cultured in the presence of platelet-derived growth factor A (Zhang et al., supra, 2000) for longer than two weeks (FIG. 2H). Thus, ESC-derived neural precursors generate all three major cell types of the CNS.

hESC-derived neural precursors migrate, incorporate, and differentiate in vivo. To assess the differentiation of hESC-derived neural precursors in vivo, we grafted them into the lateral ventricles of newborn mice (Flax J, et al., Nat. Biotech. 16:1033-1039 (1998)). The transplanted cells formed clusters in various regions of the ventricular system and incorporated in large numbers into a variety of host brain regions. Of twenty-two brains analyzed between one and four weeks after transplantation, intraventricular clusters and incorporated cells were found in nineteen and eighteen recipient brains, respectively. Individual animals analyzed after longer time periods showed that grafted cells were detectable for at least eight-weeks post transplantation. Cells within the clusters showed strong immunoreactivity to antibodies against nestin, $\beta_{III}$-tubulin and MAP2ab. Only a few cells in the aggregates expressed GFAP. Alkaline phosphatase and cytokeratine, markers typically expressed in undifferentiated ES cells and non-neural epithelia, were not detected within the clusters. No teratoma formation was observed.

Figure 3:
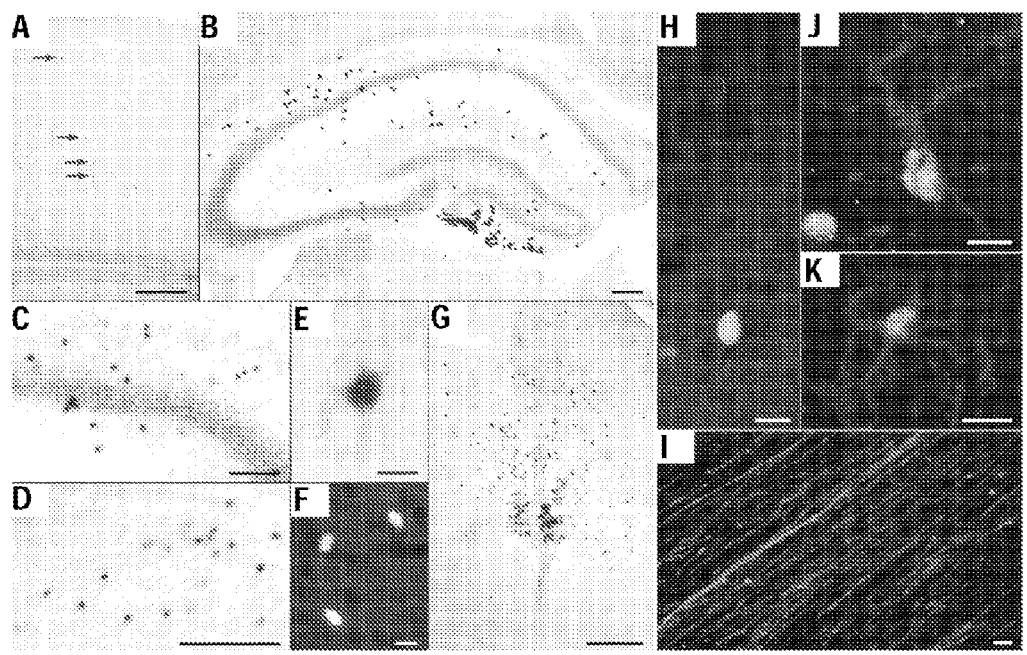

DNA in situ hybridization with a human-specific probe and immunohistochemical detection of a human nucleus-specific antigen revealed the presence of grafted cells in numerous brain regions. Gray matter areas exhibiting widespread donor cell incorporation included cortex (FIG. 3A), hippocampus (FIG. 3B,C), olfactory bulb, septum (FIG. 3D), thalamus, hypothalamus (FIG. 3E), striatum (FIG. 3F) and midbrain (FIG. 3G). Incorporation into white matter regions was most pronounced in the corpus callosum, internal capsule and hippocampal fiber tracts. Morphologically, the incorporated human cells were indistinguishable from the surrounding host cells and only detectable by the use of human-specific markers (FIG. 3). Double labeling with cell type-specific antibodies revealed that the incorporated cells had differentiated into both neurons and glia. Human ES cell-derived neurons could be clearly delineated with antibodies to $\beta_{III}$-tubulin and MAP2 (FIG. 3H, J). Frequently, they displayed polar morphologies with long processes (FIG. 3H). In addition, neurons with multipolar and immature unipolar morphologies were found (FIG. 3J). The donor-derived neurons generated numerous axons projecting long distances into the host brain, which were detected in both gray and white matter. They were particularly abundant within fiber tracts such as the corpus callosum, the anterior commissure and the fimbria hippocampi where they could frequently be traced for several hundred micrometers within a single section (FIG. 3I).

In addition to neurons, a small number of ESC-derived astrocytes was detected within the host brain tissue. They displayed stellate morphologies and exhibited strong expression of GFAP (FIG. 3K). In contrast, double labeling of incorporated human cells with antibodies to myelin proteins failed to detect mature oligodendrocytes. Some of the donor cells that had migrated into the host brain retained a nestin-positive phenotype even up to four weeks after transplantation. Many of these cells were found in perivascular locations.

Discussion

The present study indicates that engraftable neural precursors capable of generating mature neurons and glia can be generated with high yield from hESCs. Exploiting growth factor-mediated proliferation/differentiation and differential adhesion of neural precursor cells, the in vitro differentiation procedure described herein provides a new platform for the study of neural development and the generation of donor cells for nervous system repair.

A key finding of this study is the observation that the differentiation of neural precursors from hESCs appears to recapitulate early steps of nervous system development with the formation of neural tube-like structures in vitro. This phenomenon can now be exploited to study and experimentally manipulate the initial stages of human neural development under controlled conditions. The chemically defined culture system provides a unique opportunity to explore the effects of single factors on human neuroepithelial proliferation and specification in vitro. Similar to precursors derived from the developing human brain, hESC-derived precursors show a strong proliferative response to FGF2 (Flax et al., supra). However, no additive or synergistic effects on proliferation can be elicited by EGF or LIF. This finding differs from data obtained with primary cells (Zhang et al., supra, 2000; Svendsen et al., supra; Carpenter et al., supra; Vescovi0 et al., supra) and could suggest that proliferating ESC-derived neural precursors represent a more immature stage than precursor cells derived from the fetal human brain. Studies on rodent cells indeed indicate that neural stem cells isolated from early neurogenesis depend on FGF2 for proliferation and the responsiveness to EGF is acquired only at later stages of neural precursor cell differentiation (Kalyani A, et al., Dev. Biol. 186:202-223 (1997); Fricker R, et al., J. Neurosci. 19:5990-6005 (1999)).

The in vitro generation of neural tube-like structures and the possibility to isolate these structures based on their differential adhesion provides a simple yet efficient approach for generating hESC-derived neural precursors in high purity. Specifically, the strong cell-cell contacts within the neuroepithelial structures and their low adhesiveness to the tissue culture substrate permits the selective isolation of neural cells without significant contamination of undifferentiated ESCs or cells of other somatic lineages. The high efficiency of this procedure is reflected by the fact that more than 95% of the isolated cells exhibit a nestin-positive phenotype and no ESCs or non-neural epithelia are detectable in transplanted recipients. Since undifferentiated ESCs and precursors to other lineages may form tumors and foreign tissues, the generation of purified somatic cell populations is a key prerequisite for the development of ESC-based neural transplant strategies.

Following transplantation into the neonatal mouse brain, the ESC-derived neural precursors incorporated into a large variety of brain regions where they differentiated into neurons and glia. The failure to detect mature oligodendrocytes in vivo is likely due to the low oligodendroglial differentiation efficiency of human neural precursors as opposed to their rodent counterparts (Svendsen C, et al., Brain Pathol. 9:499-513 (1999)). Remarkably, donor-derived neurons were not restricted to sites exhibiting postnatal neurogenesis but were also found in many other regions of the brain. Similar data were obtained in studies involving transplantation of human CNS-derived precursors into the adult rodent brain (Tropepe V, et al., Dev. Biol. 208:166-188 (1999)). The incorporation of individual precursor cells into post-mitotic brain regions is particularly relevant with respect to cell replacement in the adult brain and spinal cord. Yet, more detailed studies will be required to determine whether and to what extent the incorporated cells acquire region-specific properties and become functionally active.

With the exception of intraventricular clusters composed of mature and immature neuroepithelial cells, no space-occupying lesions were detected within the host brains. Most notably, no teratoma formation was observed during a post-operative period up to eight weeks. While it is clear that more rigorous long-term safety studies particularly in non-human primates will be required before considering potential clinical applications, our data indicate that neural precursors isolated from differentiating hESC cultures represent a promising donor source for neural repair.

Experimental Protocols

Culture of ESCs. hESCs, H1 (passage 16 to 33), H9 (p34 to 55) and a clonal line derived from H9, H9.2 (p34 to 46) (Amit et al., supra, 2000) were cultured on a feeder layer of irradiated mouse embryonic fibroblasts with a daily change of a medium that consisted of Dulbecco's modified Eagle's medium (DMEM)/F12, 20% serum replacement (Gibco), 0.1 mM β-mercaptoethanol, 2 μg/ml heparin, and 4 ng/ml of FGF2 (PeproTech Inc., Rochy Hill, N.J.) as previously described (Thomson et al., supra, 1998). Karyotype analysis indicated that the lines at the given passages were diploid.

Differentiation cultures of ESCs. ESC cultures were incubated with dispase (Gibco BRL, 0.1 mg/ml) at 37° C. for 30 minutes, which removed ESC colonies intact. The ES cell colonies were pelleted, resuspended in ESC medium without FGF2, and cultured for four days in a 25-cm$^2$ tissue culture flask (Nunc) with a daily medium change. ESC colonies grew as floating EBs whereas any remaining feeder cells adhered to the flask. The feeder cells were removed by transferring the EBs into a new flask. EBs (~50/flask) were then plated in a 25-cm$^2$ tissue culture flask (Nunc) in DMEM/F12, supplemented with insulin (25 μg/ml), transferrin (100 μg/ml), progesterone (20 nM), putrescine (60 μM), sodium selenite (30 nM), and heparin (2 μg/ml) in the presence of FGF2 (20 ng/ml) (Zhang et al., supra, 2000; Zhang et al., supra, 1999).

Isolation and culture of neural precursor cells: To separate the clusters of rosette cells from the surrounding flat cells, the cultures were incubated with 0.1 mg/ml dispase at 37° C. for 15-20 minutes. The rosette clumps retracted whereas the surrounding flat cells remained adherent. At this point, the rosette clumps were dislodged by swaying the flask, which left the flat cells adherent. The clumps were pelleted, gently triturated with a 5-ml pipette and plated into a culture flask for 30 minutes to allow the contaminating individual cells to adhere. The floating rosette clumps were then transferred to a new flask coated with poly-(2-hydroxyethyl-methacrylate) to prohibit attachment and cultured in a medium used for human neural precursors (Zhang et al., supra, 2000) with the presence of FGF2 (20 ng/ml). To quantify the efficiency of neural differentiation and isolation, freshly separated cell clusters and the flat cells left behind were dissociated with trypsin (0.025% in 0.1% EDTA) and counted. The percentage of putative neural precursors (rosette cells) among the total cells differentiated from ESCs was obtained based on 3 independent experiments on H9 and H9.2 lines. For analyses of the differentiation potential of the ESC-derived neural precursors, cells were cultured on ornithine/laminin substrate in a medium consisting of DMEM/F12, N2 supplement (Gibco), cAMP (100 ng/ml), and BDNF (10 ng/ml, PeproTech) without the presence of FGF2. For oligodendrocyte differentiation, the ES cell-derived neural precursors were cultured in DMEM supplemented with N1 (Gibco) and platelet derived growth factor A (PDGFA) (2 ng/ml) as described (Zhang et al., supra, 2000). Morphological observation and immunostaining with markers for precursors and more matured neural cells were performed during the course of differentiation.

Histochemical and immunohistochemical staining. To better visualize the rosette formations, cultures with rosettes were rinsed with PBS and fixed in 4% paraformaldehyde and 0.25% glutaraldehyde for 1 hour. The fixed cells were then processed for embedding in plastic resin as described (Zhang et al., supra, 1999). The cultured cells were then sectioned in 1-μm thickness and stained with toluidine blue. For immunostaining, the coverslip cultures were immunostained with the following primary antibodies detected by appropriate fluorescent secondary antibodies detailed elsewhere (Zhang et al., supra, 2000; Zhang et al., supra, 1999): anti-nestin (polyclonal, gift of Dr. R. McKay of NINDS, 1:1,000); anti-polysialylated neuronal cell adhesion molecule (PSA-NCAM, mouse IgM, gift of Dr. G. Rougon of University of Marseille, France, 1:200); anti-Musashi-1 (rat IgG, gift of Dr. H. Okano, University of Tokyo, Japan, 1:500); anti-GFAP (polyclonal, Dako, 1:1,000); anti-human GFAP (Sternberg monoclonals, 1:10,000); O4 (mouse IgM, hybridoma supernatant, 1:50); anti-tyrosine hydroxylase (TH, Pel Freez, 1:500). The remaining antibodies were from Sigma: anti-β$_{III}$-tubulin (mouse IgG, 1:500); anti-neurofilament (NF) 68 (mouse IgG, 1:1,000); anti-NF 200 (polyclonal, 1:5,000); anti-MAP2ab (mouse IgG, 1:250); anti-γ-aminobutyric acid (GABA, polyclonal, 1:10,000); anti-glutamate (mouse IgG, 1:10,000). For bromodeoxyuridine (BrdU) incorporation, 4 coverslip cultures in each group were incubated with 2 μM of BrdU for sixteen hours before the cultures were fixed in 4% paraformaldehyde, denatured with 1N HCl and processed for immunolabeling and cell counting (Zhang et al., supra, 2000; Zhang et al., supra, 1999).

Intracerebroventricular transplantation and in vivo analysis. A suspension of 100,000 viable cells/μl was prepared in L15 medium (Gibco) after dissociating aggregates of neural precursors with trypsin (0.025% in 0.1% EDTA at 37° C. for 5-10 minutes). Using illumination from below the head, 2~3 μl of cell suspension was slowly injected into each of the lateral ventricles of cryoanesthetized newborn mice (C3HeB/FeJ). The grafted animals were immunosuppressed by daily injection of cyclosporin A (10 mg/kg, i.p.). One, two, four, and eight weeks following transplantation, mice were perfused transcardially with Ringer's followed by 4% paraformaldehyde. Brains were dissected and post-fixed in the same fixative at 4° C. until use. Donor cells were identified in 50-μm coronal vibratome-sections by in situ hybridization using a digoxigenin-labeled probe to the human alu repeat element (Brustle O, et al., Nat. Biotech. 16:1040-1044 (1998)) or an antibody to a human-specific nuclear antigen (MAB1281, Chemicon, 1:50). Immunopositive cells were double labeled with antibodies to GFAP (1:100), nestin, β$_{III}$-tubulin (TUJ1, BabCo, 1:500), MAP2ab (Sigma, clones AP-20 and HM-2, 1:300), and phosphorylated medium molecular weight human neurofilament (clone HO-14, 1:50, a gift of J. Trojanowski). Primary antibodies were detected by appropriate fluorophore-conjugated secondary antibodies. Sections were analyzed on Zeiss Axioskop 2 and Leica laser scan microscopes.

Example 2

Generation of Midbrain Dopaminergic Neurons

A first step toward potential application of stem cell therapy in neurological conditions is the directed differentiation of neural cells with correct positional and transmitter phenotypes. Here we show a robust generation of functional dopaminergic (DA) neurons from hESCs through a specific sequence of morphogen actions. Treatment of hESC-derived neuroectodermal cells at an early stage, before the expression of Sox1, with FGF8 is essential for specification of DA neurons with correct midbrain DA projection neuronal phenotypes. The in vitro generated DA neurons may be used for toxicological and pharmaceutical screening and for potential cell therapy in Parkinson's disease.

Parkinsons' disease (PD) results from progressive degeneration of DA neurons in the midbrain, especially the substantia nigra. Current therapy for PD relies primarily on symptom relief by systemic administration of DA precursors such as levadopa. Such therapy is effective for the first few years but almost invariably loses its efficacy and produces serious side effects. Administration of growth factors such as glial cell line-derived neurotrophic factor (GDNF) has been shown to be effective in a small clinical trial (Gill S, et al., Nat. Med. 9:589-595 (2003)). This therapy would depend on a sufficient number of surviving DA neurons, and its long-term therapeutic potential remains to be investigated. Because of the focal nature of neuronal degeneration, cell transplantation has been proposed as an alternative therapy (Bjorklund A & Lindvall O, Nat. Neurosci. 3:537-544 (2000)). In some successful cases, transplanted fetal midbrain cells survive for over a decade and contribute to the relief of symptoms (Kowdower J, et al., N. Engl. J. Med. 332:1118-1124 (1995); Piccini P, et al., Nat. Neurosci. 2:1137-1140 (1999)), although the recent controlled clinical trials cast doubt on the efficacy of fetal tissue transplant therapy for PD (Freed C, et al., N. Engl. J. Med. 344:710-719 (2001); Olanow C, et al., Ann. Neurol. 54:403-414 (2003)). These phenomena are indicative of the complexity of PD. A reliable, renewable source of functional human midbrain DA neurons is urgently needed for a systematic study of the genesis of the DA system, pathogenic process affecting the survival and function of DA neurons, and development of the sustainable therapeutics for PD.

It has been shown that DA neurons can be efficiently generated from mESCs, which are derived from the inner cell mass of pre-implantation embryos at the blastocyst stage (Evans M & Kaufman M, Nature 292:154-156 (1981); Martin G, Proc. Natl. Acad. Sci. USA 78:7634-7638 (1981)). mESCs are first induced to neuroectodermal cells by FGF2 (Lee S, et al., Nat. Biotechnol. 18:675-679 (2000)) or by stromal cell-derived inducing activity (Kawasaki H, et al., Neuron 28:31-40, 2000; Barberi T, et al., Nat. Biotechnol. 21:1200-1207 (2003)). The neuroectodermal cells are subsequently exposed to FGF8 followed by SHH for DA neuron induction. In this study, we have established a robust system to induce hESCs (Thomson et al., supra, 1998)) to differentiate into neuroectodermal cells (Zhang et al., supra, 2001) that, in response to FGF8 and SHH, generated a large proportion of DA neurons with midbrain projection characteristics. We have found that, in order to generate DA neurons with midbrain projection neuronal phenotypes, hESCs require exposure to FGF8 before precursor cells become $Sox1^+$ expressing neuroectodermal cells.

Results hESC-Derived Neuroectodermal Cells Display a Forebrain Character

ESC colonies, detached from a feeder layer, were cultured in suspension as aggregates for four days in ESC growth medium, and then grown in an adhesive culture dish in a chemically defined neural medium containing FGF2 (20 ng/ml) (Zhang et al., supra, 2001). Cells in the colony center developed a columnar morphology and lined up in a rosette formation around day nine (FIG. 4A). These columnar cells were positive of Pax6, but negative for the pan-neural transcription factor Sox1 (not shown), indicative of early neuroectodermal cells. Over another five to six days (day 14-15), the columnar cells expanded and organized into neural tube-like rosettes (FIG. 4B), and expressed Sox1 (FIG. 4C), a transcription factor expressed by definitive neuroectodermal cells during neural tube closure (Pevny L, et al., Development 125:1967-1978 (1998)). They were positive for brain factor (Bf1), a transcription factor expressed by forebrain cells (Tao W & Lai E, Neuron 8:957-966 (1992)), but negative for engrailed 1 (En-1) (FIG. 4D), a transcription factor expressed by midbrain cells (Davidson D, et al., Development 104:305-316 (1988); Wurst W, et al., Development 120:2065-2075 (1994)), suggesting a forebrain identity of the in vitro generated neuroectodermal cells.

Induction of Midbrain Phenotype Requires Early Action of FGF8

For differentiation to DA neurons, neuroectodermal cells in the neural tube-like rosettes were enriched through differential enzymatic and adhesion treatment (Zhang et al., supra, 2001), expanded for four days as aggregates in suspension with FGF2, and were then plated onto a laminin substrate and treated with SHH (50-200 ng/ml) and FGF8 (20-100 ng/ml) for six days. Immunocytochemical analyses revealed that the vast majority of the neuroectodermal cells remained positive for Bf1 but not for En-1 (not shown).

The failure of FGF8 to induce $Sox1^+$ neuroectodermal cells to express En-1 suggests that the Sox1-expressing neuroectodermal cells may be refractory to patterning signals. Since the Sox1-expressing cells are generated two weeks after differentiation of hESC (equivalent to a six-day-old embryo (Thomson et al., supra, 1998) and formed neural tube-like structures, they may correspond to the neuroectodermal cells at neural tube closure during which neuroectodermal cells express Sox1 and are regionally specified (Lumsden A & Krumlauf R, Science 274:1109-1115 (1996)). This led us to hypothesize that FGF8 may promote midbrain specification before neuroectodermal cells express Sox1. We thus applied FGF8 (100 ng/ml) at the time when the cells in the colony center became columnar at day nine. After six days, cells in the colony center developed neural tube-like formations, as seen in the presence of FGF2. These neuroectodermal cells were similarly enriched, expanded in FGF8 for four days, and then treated with SHH for six days on the laminin substrate. Under this culture condition, En-1 expression was observed in the nestin-expressing neuroectodermal cells (FIG. 4E), although there were still cells that expressed Bf1 (FIG. 4F). Thus, neuroectodermal cells were efficiently regionalized before they become $Sox1^+$.

Regionalized Neuroectodermal Cells Differentiate into DA Neurons

The neuroectodermal cells were dissociated and differentiated in a neural differentiation medium. They did not express stage specific embryonic antigen 4 (SSEA4), a glycoprotein highly expressed by undifferentiated hESCs. The disaggregated neuroectodermal cells, initially distributed evenly, re-formed rosettes-three to five days after plating. They then extended processes and exhibited polar morphology. At three weeks after differentiation, about one third of the total differentiated cell population (31.8±3.1% $TH^+$ cells of 17,965 cells counted from four experiments) were positive for tyrosine hydroxylase (TH) (FIG. 5A). A similar percentage of $TH^+$ cells was obtained from both H9 and H1 hESC lines. Most TH-expressing cells were 10-20 µm in diameter. They exhibited multipolar morphology, with differentiable axons and dendrites (FIG. 5A). All the $TH^+$ cells were stained positively with a neuronal marker $\beta_{III}$-tubulin$^+$ neurons, about 50% were $TH^+$ (FIG. 5B, 6,383 $TH^+$ cells of 12,859 $\beta_{III}$-tubulin$^+$ neurons from four experiments).

In the biosynthesis of monoamines, TH hydroxylates tyrosine to L-DOPA, which is subsequently decarboxylated to become DA by AADC. Another two enzymes, DβH and phenylethanolamine N-methyltransferase (PNMT), transform DA to norepinephrine and catalyze norepinephrine to epinephrine, respectively. Immunostaining showed that all $TH^+$ cells were AADC (FIG. 5C-E) although some $AADC^+$ cells were negative for TH (FIG. 5E). However, $TH^+$ cells were negative for DβH (FIG. 5F) and PNMT (not shown), although DβH strongly stained noradrenergic neurons in the adult rat and embryonic monkey brainstem (inset in FIG. 5F). These data suggest that the TH-expressing neurons possess both enzymes that are necessary for dopamine synthesis, and that these neurons are DA neurons rather than noradrenergic or adrenergic neurons.

ESC-Generated DA Neurons Display Midbrain Phenotypes

RT-PCR analyses indicated that Nurr1, Limx1b, En-1 and Ptx3, which are involved in midbrain DA neuron development (Zetterstrom R, et al., Science 276:248-250 (1997); Smidt M, et al., Proc. Natl. Acad. Sci. USA 94:13305-13310 (1997); Saucedo-Cardenas O, et al., Proc. Natl. Acad. Sci. USA 95:4013-4018 (1998); Wallen A, et al., Exp. Cell Res. 253:737-746 (1999); Smidt M, et al., Nat. Neurosci. 3:337-341 (2000); Simon H, et al., J. Neurosci. 21:3126-3134 (2001); Van den Munckhof P, et al., Development 130:2535-2542 (2003); Nunes I, et al., Proc. Natl. Acad. Sci. USA 100:4245-4250 (2003)), were not expressed at a high level until neuroectrodermal cells were differentiated into DA neurons (FIG. 6A). Immunostaining revealed that most TH$^+$ cells with multiple processes co-expressed the midbrain marker En-1 in the nuclei (FIG. 6B). Thus, DA neurons generated using the above approach possess a midbrain positional identity.

DA neurons in the olfactory bulb often co-express γ-aminobutyric acid (GABA) (Kosaka T, et al., Exp. Brain Res. 66:191-210 (1987); Gall C, et al., J. Comp. Neurol. 266:307-318 (1987)). Double immunostaining of TH and GABA indicated that most of the DA neurons were negative for GABA although GABA$^+$ neurons were found in the culture (FIG. 6C). Among all TH$^+$ cells, 8% (8.7±3.9%, 6,520 TH$^+$ cells counted from four experiments) of TH$^+$ cell co-expressed GABA. Most of these double positive cells were small bipolar cells (inset in FIG. 6C). Some midbrain DA neurons, especially those in the ventral tegmental area, co-express cholecystokinin octapeptide (CCK8) or calbindin along with TH (McRitchie D, et al., J. Comp. Neurol. 364:121-150 (1996); Hokfelt T, et al., Neurosci. 5:2093-2124 (1980)). Immunohistochemical analyses indicated that the TH$^+$ neurons were observed (FIG. 6D). These calbindin neurons were mostly small cells. No CCK8 positive cells were detected in the cultures.

ESC-generated DA Neurons are Biologically Functional

Immunostaining showed that all TH$^+$ neurons expressed c-Ret, a component of the receptor for GDNF (FIG. 7A-C). The majority of the TH$^+$ cells, especially those with branched neurites, expressed vesicular monoamine transporter 2 (VMAT2, FIG. 7D-F), which is responsible for packaging dopamine into subcellular compartments in monoamine neurons (Nirenberg M, et al., J. Neurosci. 16:4135-4145 (1996)). In addition, TH$^+$ neurons expressed synaptophysin, a membrane glycoprotein essential to synapse formation (Calakos N & Scheller R, J. Biol. Chem. 269:24534-24537 (1994)) (FIG. 7A-1).

Dopamine release is a functional hallmark of DA neurons. High performance liquid chromatography (HPLC) analyses revealed the presence of dopamine in the medium of DA differentiation cultures, with 230.8±44.0 pg/ml in the cultures treated with ascorbic acid (AA), FGF8 and SHH and 46.3±9.2 pg/ml in the control cultures without the treatment of M, FGF8 and SHH (FIG. 8A). When cultured cells were washed and incubated in HBSS for fourteen minutes, the dopamine level was similar between the two cultures (FIG. 8A). However, depolarization of the cultured neurons by 56 mM KCl in HBSS significantly increased the amount of DA (35.8±9.2 and 111.0±15.0 pg/ml in the cultures without and with AA, FGF8 and SHH treatment, respectively; FIG. 8A). These observations suggest that the in vitro generated DA neurons can secrete DA and the release of DA is activity-dependent.

Electrophysiological recordings were used to determine whether ES-generated DA neurons were functionally active. In cells maintained in culture for thirty to thirty-eight days (n=14), the resting membrane potential ($V_{rest}$) ranged from −32 to −72 mV (−54±2.9 mV), cell capacitance ($C_m$) ranged from 11 to 45 pF (21±2.7 pF), and input resistance ($R_{in}$) ranged from 480 to 3500 MΩ (1506±282 MΩ). Depolarizing current steps (0.2 nA×200-500 ms) usually elicited single action potentials, but in several cases decrementing trains of action potentials were observed (FIG. 8bi and ii). Action potential (AP) threshold ranged from −26 to −5.2 mV (−17.4±2.1 mV), and peaked at −9.6 to 30 mV. AP's up to 50.2 mV were observed (32±2.8 mV). AP duration ranged from 3 to 20.6 ms (7.2±1.3 ms). Spontaneous firing was observed in two cells (FIG. 8C).

In voltage clamp mode, both inward and outward currents were observed in all cells (not shown), but their relative magnitudes varied considerably. Inward currents were activated rapidly (<1 ms), and peaked within 1-3 ms. Activation threshold was −30±1 mV, maximal peak current amplitude was obtained at a mean voltage of −13±1.9 mV, and currents were completely blocked by tetrodotoxin (TTX, n=3). These properties are consistent with the presence of voltage-gated sodium channels that underlie action potential generation. In three cells we observed spontaneous transient currents that had the characteristics of synaptic currents, including a rapid rise and slower decay phase. One of these recordings was made with a K-gluconate based pipette solution, and holding this cell at −40 mV allowed us to observe both outward (inhibitory) and inward (excitatory) currents (FIG. 8di and dii). Although all fourteen cells were injected with biocytin, only five cells were recovered after the completion of the immunostaining procedures. However, all of the five biocytin-filled cells were labeled TH (FIG. 8E-G).

Discussion

We have demonstrated here that functional DA neurons with midbrain neuronal projection characteristics can be efficiently generated from hESCs through three simple non-genetic steps: induction of neuroectodermal cells with FGF2, specification of ventral midbrain identity by FGF8 and SHH during neuroectodermal formation, and differentiation of the regionally specified progenitors to DA neurons. Unlike the findings obtained from mESC studies in which DA neurons with midbrain characteristics can be generated from expanded neuroectodermal cells (Lee et al., supra, 2000), we have found that specification or regionalization with FGF8 before precursor cells become Sox1$^+$ neuroectodermal cells is essential for a robust generation of human DA neurons with correct midbrain and functional phenotypes.

From the standpoint of stem cell biology, it seems very logical to direct mESCs to neuroectodermal cells, expand them, regionalize or specify them with FGF8 and SHH, and subsequently differentiate them into DA neurons, a stepwise protocol developed by McKay and colleagues (Lee et al., supra, 2000). We hypothesized that the same principle should apply to human primates. Indeed, we are able to generate a large number of DA neurons by differentiating hESCs into neuroectodermal cells that express Sox1 and organize into neural tube-like rosettes in the presence of FGF2 (Zhang et al., supra, 2001), treating the neuroectodermal cells with FGF8 and SHH to induce a ventral midbrain fate and finally differentiating the cells into neurons. However, most of the DA neurons generated in this way lack some of the key characteristics of midbrain projection DA neurons, e.g., large size with complex morphology and expression of midbrain transcription factors at the protein level. The Sox1 positive neuroectrodermal cells, even after treatment with FGF8 and SHH, are still negative for En-1 but positive for Bf1, suggesting the Sox1-expressing neuroectodermal cells are refractory for specification to a midbrain fate. The process of neuroectodermal differentiation from hESCs in our culture system parallels what is seen during in vivo development (Zhang, supra, 2003). In vivo, the neural tube forms at the end of third week of human gestation and Sox1 is expressed by the neuroectoderm during neural tube closure based on mouse embryological study (Pevny L, et al., Development 125: 1967-1978 (1998)). In culture, the neuroectodermal cells form neural tube-like rosettes and express Sox1 after two weeks of differentiation from hESCs that are equivalent to a six-day-old human embryo (Thomson et al., supra, 1998). The projection neurons, including midbrain DA neurons, are differentiated from neuroectodermal cells in the neural tube at the early stage and these neuroectodermal cells are already regionally specified during the process of neural tube closure (Lumsden A & Krumlauf R, supra, 1996). This may explain why the hESC-generated Sox1-expressing neuroectodermal cells that possess forebrain phenotypes are not responsive to morphogens for generating DA neurons with midbrain phenotypes. Our hypothesis that FGF8 may instruct the early precursors to adopt a midbrain identify is confirmed by the generation of DA neurons that have characteristics of projection neurons such as large cell bodies with complex processes and expression of midbrain makers En1, after the Sox1 columnar cells in the early rosettes are treated with FGF8.

It is presently not clear why FGF2-induced mESC-, but not hESC-derived neuroectodermal cells, can be efficiently regionalized after expansion. There is recent evidence that the dorsal or ventral identity of neural progenitors isolated from mouse spinal cord may be deregulated upon culture, especially in the presence of FGF2 (Gabay L, et al., Neuron 40:485-499 (2003)), which may partly account for the capability of expanded mouse ES-derived neuroectodermal cells to be respecified. Our studies on the differentiation of other projection neurons such as spinal motor neurons are consistent with the present observation that generation of large projection neurons requires early action of morphogens.

DA neurons are present in several areas of the brain, including midbrain, hypothalamus, retina, and olfactory bulbs. The human ES cell-generated DA neurons in this study resemble midbrain projection DA neurons. Most of the DA neurons do not co-express GABA, whereas co-expression of GABA and TH is a major feature of olfactory DA interneurons (Kosaka et al., supra, 1987; Gall et al., supra, 1987). In the midbrain, there are at least two major groups of DA neurons, those in the substantia nigra (A9) and in the ventral tegmental area (A10), each having different targets (Bjorklund A & Lindvall O, Handbook of Chemical Neuroanatomy, Vol. 2: Classical Transmitters in the CNS (Bjorklund A & Hokfelt T, eds), Amsterdam, Elsevier Science Publishers, pp. 55-111 (1984)). Most DA neurons in the ventral tegmental area express calbindin or CCK, whereas few in the substantia nigra do (McRitchie D, et al., J. Comp. Neurol. 364:121-150 (1996); Hokfelt T, et al., Neurosci. 5:2093-2124 (1980); Haber S, et al., J. Comp. Neurol. 362:400-410 (1995)). Our observation that the hESC-generated DA neurons do not co-express TH with CCK8 or calbindin suggests that these DA neurons resemble more closely the substantia nigra DNA neurons.

The robust capability of hESCs to generate large projection neurons with an appropriate regional identity such as midbrain DA neurons opens up an unprecedented opportunity to dissect the early phase of neural development using the hESC system. Our data demonstrates a requirement for morphogens, such as FGF8, to act on early neuroectodermal cells, which are unspecified, for the generation of early born midbrain projection DA neurons. This may explain why stem cells or progenitors isolated and expanded from embryonic and adult mammalian brains that are already specified are refractory to generate projection neurons (Svendsen C, et al., Exp. Neurol. 148:135-146 (1997); Daadi M & Weiss S, J. Neurosci. 19:4484-4497 (1999); Storch A, et al., Exp. Neurol. 170:317-325 (2001)). The in vitro generated human DA neurons also offer a system for toxicological and pharmaceutical screening for chemicals and drugs that may affect human DA neurons. Studies are underway to determine whether these human DA neurons generated in an culture Petri dish are functional in PD animal models.

Methods

ESC cultures. hESC lines, H9 (p21-56) and H1 (p35-40), were propagated weekly on irradiated mouse embryonic fibroblasts (MEF) with a daily change of an ESC growth medium that consisted of Dulbecco's modified Eagle's medium (DMEM)/F12 (Gibco), 20% serum replacer (Gibco), 1 mM glutamine (Sigma), 0.1 mM non-essential amino acids (Gibco), 2 μg/ml of heparin (Sigma), 0.1 mM β-mercaptoethanol (sigma), and 4 ng/ml of FGF2 (R & D Systems), as described by Thomson (Thomson et al., supra, 1998). Differentiated colonies were physically removed using a curved Pasteur pipette and the undifferentiated state of ESCs was confirmed by typical morphology and immunostaining with Oct4 and SSEA4.

Differentiation and enrichment of neuroectodermal cells. hESC colonies were detached from MEF layer by the treatment of the culture with 0.2 mg/ml of dispase (Roche Diagnostics) and grown as floating cell aggregates (embryoid body) for four days with a daily change of ESC medium. They were then grown in an adherent substrate in a neural medium consisting of DMEM/F12 (2:1), supplemented with N2 (Gibco), 0.1 mM non-essential amino acids, 2 μg/ml heparin with a medium change every other day. The ESC aggregates attached and formed individual colonies at around day six. Neuroectodermal cells, exhibited by columnar cells organizing into neural tube-like rosettes, were developed at around day fourteen (Zhang et al., supra, 2001). The neural rosettes were isolated through differential enzymatic response (Zhang et al., supra, 2001). Growth factors were added during the course of differentiation to influence regionalization (see results).

DA neuron differentiation. The enriched neuroectodermal cells were dissociated by 0.025% trypsin and 0.27 mM EDTA in PBS at 37° C. for 10-15 minutes and plated onto 12-mm coverslips (pre-coated with 100 μg/ml polyornithine and 10 μg/ml laminin) at a density of 40,000-50,000 cells/coverslip. The neuronal differentiation medium consisted of neurobasal medium (Gibco) supplemented with N2, 0.1 mM non-essential amino acids, 0.5 mM glutamine, 1 μg/ml laminin, 1 μM cAMP, 200 μM AA (Sigma), 10 ng/ml BDNF (R & D Systems) and 10 ng/ml GDNF (R & D Systems). The cells were cultured for three to four weeks with medium change every other day.

Immunocytochemistry and cell quantification. Coverslip cultures were fixed in 4% paraformaldehyde in PBS for 10-20 minutes or methanol (−20° C.) for 5 minutes and processed for immunostaining (Zhang et al., supra, 2001). The following primary antibodies were used: mouse anti-SSEA4 (1:40), mouse anti-En-1 (1:50) and mouse anti-Pax6 (1:5000, all from Developmental studies hybridoma bank); rabbit anti-Sox 1 (1:500), rabbit anti-human nestin (1:200), rabbit anti-AADC (1:1000), sheep anti DβH, (1:400), mouse anti-synaptophysin (1:500) and rabbit anti-CCK8 (1:2000, all from Chemicon); mouse anti-TH (1:1000), mouse anti-$\beta_{III}$ tubulin (1:500), rabbit anti-GABA (1:5000) and mouse anti-calbindin (1:400, all from Sigma); rabbit anti-TH (1:500) and rabbit anti-VMAT2 (1:500, all from Pel-Freez); Goat anti-c-Ret (1:400) and mouse anti-Oct4 (1:1000, both from Santa Cruz); rabbit anti-Bf1 (1:5000; gift from Lorenz Studer). Antibody-antigen reaction was revealed by appropriate fluorescence-conjugated secondary antibody. Cell nuclei were stained with Hoechst 33342. Staining was visualized with a Nikon fluorescence microscope. Brain sections from adult rats and E38 embryonic monkeys were used as positive controls for many of the antibodies against neuronal types and neurotransmitters. Negative controls were also set by omitting the primary or secondary antibodies in the immunostaining procedures. Cell counting was achieved blindly by using a reticule on eyepiece and a 40× objective. The cells in ten visual fields were randomly selected and counted from each coverslip.

RT-PCR

Total RNA was extracted from cultured cells using RNA Stat-60 (Tel-Test, Friendswood, Tex.), followed by the treatment with DNase I (DNA-free, Ambion). Synthesis of cDNA was carried out with the Superscript First-Strand Synthesis System for RT-PCR (Invitrogen) according to the manufacturer's directions. PCR amplification was performed using a standard procedure with Taq Polymerase (Promega). The number of cycles varied from 25 to 35 cycles depending on the particular mRNA abundance with denaturation at 94° C. for 15 seconds, annealing temperatures at 55° C. or 60° C. for 30 seconds according to the primers, and elongation at 72° C. for 45 seconds. Negative control was achieved by omitting transcriptase during reverse transcription or cDNA sample during PCR. The primers and product lengths were as follows: GAPDH (5'-ACCACAGTCCATGCCATCAC-3' (SEQ ID NO:1), 5'-TCCACCACCCTGTTGCTGTA-3' (SEQ ID NO:2), 450 bp); Nurr1 (5'-CGATGCCTTGTGTTCAGGCG-CAG-3' (SEQ ID NO:3), 5'-AGCCTTTGCAGCCCTCA-CAGGTG-3' (SEQ ID NO:4), 858 bp); Ptx3 (5'-GTGGGTG-GAGAGGAGAACAA-3' (SEQ ID NO:5), 5'-TTCCTCCCTCAGGAAACAATG-3' (SEQ ID NO:6), 175 bp); Lmx1b (5'-GGGATCGGAAACTGTTACTGC-3' (SEQ ID NO:7), 5'-GTAGTCACCCTTGCACAGCA-3' (SEQ ID NO:8), 218 bp); En-1 (5'-CCCTGGTTTCTCTGG-GACTT-3' (SEQ ID NO:9), 5'-GCAGTCTGTGGGGTCG-TATT-3' (SEQ ID NO:10), 162 bp).

DA Measurement

After twenty-one days of DA neuronal differentiation, media conditioned for forty-eight hours were collected. Activity-dependent dopamine release from the cultured cells was measured by first conditioning cultured cells in Hank's balanced salt solution (HBSS) for 15 minutes and then replacing it with HBSS containing 56 mM KCl for 14 minutes at 37° C. Dopamine in the culture media or in HBSS was stabilized by adding 20 μl stabilization buffer (900 mg EGTA and 700 mg gluthatione in 10 ml of 0.1 M NaOH) and samples were stored in −80° C. A HPLC kit (Chromsystems) was used to extract monoamines. The levels of monoamines were determined by HPLC (Model 508 autosampler and model 118 pump, Beckman) coupled to electrochemical detector (Coulochem II, ESA Inc.) by using MD-TM mobile phase (ESA Inc.). The cultures in each group were triplicated and data were collected from three separate experiments.

Electrophysiological Recording

Electrophysiological properties of the DA neurons differentiated from hESCs were investigated using whole-cell patch-clamp recording techniques (Hammill, OP., et al., Pflugers Arch. 391:85-100, 1981). Pipettes were filled with intracellular solutions containing (mM) KCl 140 or K-gluconate 140, Na$^+$-HEPES 10, BAPTA 10, Mg$^{2+}$-ATP 4, (pH 7.2, 290 mOsm, 2.3-5.0 MΩ). Biocytin (0.5%, Sigma) was added to the recording solution and subsequent labeling with streptavidin-Alex Flur 488 (1:1000, Molecular Probes) and an antibody against TH was used to identify DA neurons. The bath solution contained (in mM) NaCl 127, KH$_2$PO$_4$ 1.2, KCl 1.9, NaHCO$_3$ 26, CaCl$_2$ 2.2, MgSO$_4$ 1.4, glucose 10, 95% O$_2$/5% CO$_2$ (pH 7.3, 300 mOsm). For some experiments, TTX (1 μm) was applied in the bath solution to block voltage-gated sodium currents.

Current-clamp and voltage-clamp recordings were performed using a MultiClamp 700A amplifier (Axon Instruments). Signals were filtered at 4 kHz, sampled at 10 kHz using a Digidata 1322A analog-digital converter (Axon Instruments), and acquired and stored on a computer hard disk using commercially available software (pClamp9, Axon Instruments). Access resistance was typically 8-18 MΩ and was compensated by 50-80% using amplifier circuitry. Voltages were corrected for liquid junction potential of +13 mV (Neher E, Methods Enzymol. 207:123-131 (1992)). V$_{rest}$ and action potentials were examined in current-clamp mode. Spontaneous excitatory (inward) and inhibitory (outward) synaptic currents were characterized in voltage-clamp mode using K-gluconate based pipette solution and V$_{hold}$=−40 mV. Synaptic events were detected using a template detection algorithm (Mini Analysis Program 4.6.28, Synaptosoft) and deactivation phase was fitted to a biexponential function using the Levenberg-Marquardt algorithm. Data are presented as mean ±SE.

Example 3

Generation of Motor Neurons

Generation of motor neurons in vertebrate animals involves at least three steps: neuralization of ectodermal cells, caudalization of the neuroectodermal cells, and ventralization of the caudalized neural progenitors (Jessell T, Nat. Rev. Genet. 1:20-29 (2000)). We first established a culture system for efficient neuroectodermal differentiation from hESCs (Thomson et al., supra, 1998) (H1 and H9 lines) using an adherent colony culture in the presence of FGF2 (Zhang et al., supra, 2001), based on the principle that vertebrate neuroectoderm develops in response to FGF and/or anti-BMP (bone morphogenetic protein) signals (Wilson S & Edlund T, Nat. Neurosci. 4:Suppl.:1161-1168 (2001)). The first sign of neural differentiation was the appearance of columnar cells forming rosettes in the center of colonies 8-10 days after ESCs were removed from feeder cells for differentiation. The columnar cells in the rosettes, but not the flat cells in the outgrowth area, expressed a neuroectoderm marker Pax6 but not the pan-neuroectodermal transcription factor Sox1 (FIG. 9A), which is expressed by neuroepithelial cells during neural tube formation (Pevny et al., supra, 1998). With further culturing in the same medium for another four to five days, the columnar cells organized into neural tube-like rosettes with lumens (FIG. 9B) and expressed both Pax6 and Sox1 (FIG. 9C, D). Thus, differentiation of neuroectodermal cells from hESCs involves at least two distinctive stages, the Pax6$^+$/Sox1$^-$ columnar cells in the early rosettes eight to ten days after neural induction, and the Pax6$^+$/Sox1$^+$ cells forming neural tube-like late rosettes fourteen days after induction.

Immunocytochemical analyses revealed that the rosette cells, which expressed Pax6 (FIG. 9E), Sox1, and nestin, were positive for Otx2 (FIG. 9F, H), a homeodomain protein expressed by fore- and mid-brain cells; but negative for HoxC8 (FIG. 9H), a homeodomain protein produced by cells in the spinal cord. They were also negative for En1, which is expressed by midbrain cells (FIG. 9G). These results suggest that the neuroectodermal cells possess a forebrain phenotype, similar to that initially acquired by neuroectodermal cells during early in vivo development (Stern D, Nat. Rev. Neurosci. 2:92-98 (2001)).

To differentiate motor neurons from neuroectodermal cells, Sox1+ neuroectodermal cells in the neural tube-like rosettes were isolated through enzymatic treatment (Zhang et al., supra, 2001) and differentiated on the laminin substrate in the presence of retinoic acid (RA, 0.001-1 μM), a caudalizing reagent (Blumberg B, et al., Development 124:373-379 (1997)), and SHH (50-500 ng/ml), a ventralizing morphogen (Jessell T, Nat. Rev. Genet. 1:20-29 (2000); Briscoe J & Ericson J, Curr. Opin. Neurobiol. 11:43-49 (2001)). By fourteen days after plating, a large number of cells in the outgrowth area formed a network through their processes (FIG. 10A). Immunostaining analyses indicated that the differentiated cells were positive for neuronal markers $\beta_{III}$-tubulin and MAP2. A large proportion (>50%) of them were also positive for Isl1 (FIG. 10A) and Lim3 (not shown), transcription factors that are associated with motor neuron development (Jessell, supra; Briscoe & Ericson, supra, 2001; Shirasaki R & Pfaff S, Annu. Rev. Neurosci. 25:251-281 (2002)). However, very few cells in cultures between one to three weeks expressed HB9 (FIG. 10A), a motor neuron-specific transcription factor (Arber S, et al., Neuron 23:659-674 (1999)). These suggest that the Sox1+ neuroectodermal cells may be refractory for motor neuron induction.

The Sox1-expressing cells may correspond to neuroectodermal cells in the neural tube given the formation of neural tube-like rosettes and expression of Sox1 at a time equivalent to a three-week-old human embryo. The neuroectodermal cells in the neural tube are regionally specified (Lumsden A & Krumlauf R. Science 274:1109-1115 (1996)). This consideration led us to hypothesize that RA may promote caudalization and/or motor neuron specification before neuroectodermal cells express Sox1. We thus treated the neuroectodermal cells with RA (0.001-1 μM) at an earlier stage, i.e., when columnar cells began to organize into rosettes and expressed Pax6. Cultures treated in this way for 6 days developed into neural tube-like rosettes and expressed Sox1, indistinguishable from FGF2 treated cultures. After the rosette clusters were isolated and adhered to the laminin substrate, numerous neurites extended from the cluster as early as twenty-four to forty-eight hours after plating. By fourteen days after plating, the neurite outgrowth area covered almost the entire (11-mm diameter) coverslip although there were limited numbers of neuronal cell bodies in the outgrowth area (FIG. 10A). The majority of cells were positive for Isl ½, among which about 50% were also HB9+ (FIG. 10B), suggesting that these double positive cells are motor neurons. The Isl ½+ and HB9− cells were likely interneurons.

HB9-expressing cells first appeared at day six and reached a high proportion around day ten to twelve after the neural rosettes were plated for differentiation. They were largely localized to the cluster, with about 21% of the total cells in the cluster and few cells in the outgrowth area (FIG. 10A, D). The highest proportion of HB9+ cells was induced in the presence of 0.1-1.0 μM of RA. RA at the dose over 1.0 μM resulted in degeneration of some cells in our chemically defined adherent cultures. In the absence of RA, or SHH, or both, there were very few HB9+ cells (FIG. 10D). All the HB9-expressing cells were stained with $\beta_{III}$-tubulin (FIG. 10C). Thus treatment with RA on early neuroectodermal cells is required for efficient induction of motor neurons.

To understand why RA induces early but not late neuroectodermal cells to differentiate into motor neurons, we first examined the effect of RA on caudalization of the neuroectodermal cells. Treatment of early rosette cells (Pax6+/Sox1−) with RA (0.001-1.0 μM) or FGF2 (20 ng/ml) for seven days resulted in the decreased expression of Otx2 and increased expression of Hox genes such as Hox B1, B6, C5, and C8 in a dose-dependent manner (FIG. 11A). Genes expressed by more caudal cells were induced by higher doses of RA. Treatment of late rosette cells (Pax6+/Sox1+) with RA for one week did not alter the Hox gene expression pattern induced by FGF2 (not shown). The RA-treated early rosette cells, isolated and cultured in the neuronal differentiation medium, expressed HoxC8 protein first at day six and mostly at day ten to twelve after differentiation, as revealed by immunocytochemistry (FIG. 11D). Cells at this stage lacked Otx2 expression (FIG. 11C). All the HoxC8+ cells were ($\beta_{III}$-tubulin+ neurons (FIG. 11E). In contrast, late rosette cells treated with RA for one week and then differentiated for two weeks, yielded few HoxC8+ cells, although Otx2-expressing cells were decreased (not shown). Thus treatment of early but not late neuroectodermal cells with RA results in efficient caudalization with expression of HoxC proteins, which are associated with spinal motor neurons (Liu J, et al., Neuron 32:997-1012 (2001)).

We then compared the effect of SHH on early and late neuroectodermal cells for ventralization. The hESC-derived neuroectodermal cells, whether they were Pax6+ or Sox1+, did not express Olig2 (FIG. 11F), a homeodomain protein expressed in ventral neural progenitor cells that are destined to become motor neurons and oligodendrocytes in the spinal cord (Lu Q, et al., Cell 109:75-86 (2002); Zhou Q. et al., Neuron 31:791-807 (2001)). When the Pax6+/Sox1− neuroectodermal cells were cultured in the presence of RA for one week, then isolated and further differentiated for another two weeks in the absence of SHH, very few cells expressed Olig2 (not shown). However, in the presence of SHH (50-500 ng/ml), many cells expressed Olig2 in the nuclei (FIG. 11G). In contrast, Pax6+/Sox1+ neuroectodermal cells, differentiated for two weeks under the same condition, generated few Olig2-expressing cells (FIG. 11H). Thus, neuroectodermal cells, treated with RA at an early but not the late stage, can be efficiently induced to a ventral neural progenitor fate in response to SHH.

To further discern why early RA treatment is required for motor neuron specification even though FGF2 also induces a caudal fate (FIG. 11A), we examined the expression of Class I (Irx3, Pax6) and Class II (Olig2, Nkx2.2, Nkx6.1) molecules that are important in refining progenitor domains in the spinal cord (Jessell, supra, 2000; Briscoe & Ericson, supra, 2001). RA induced a much more robust expression of SHH and Class II genes particularly Olig2 and Nkx6.1 in early than in late neuroectodermal cells (FIG. 11B). Thus, early neuroectodermal cells are more responsive to RA in upregulating the expression of SHH and Class II factors, which are essential for motor neuron specification.

Cells that expressed choline acetyltransferase (ChAT) appeared three weeks after the caudalized neuroectodermal cells were plated for motor neuron differentiation and these cells increased steadily for up to seven weeks, the longest culture period analyzed in this study (FIG. 12A). The ChAT-expressing cells were largely localized to the cluster (FIG. 12A), corresponding to the localization of the HB9+ cells. These cells were mainly multipolar cells and had large somas of 15-20 μm in diameter, with some being as big as 30 μm (FIG. 12A, B). Co-expression of HB9 in the nuclei and ChAT in the soma and processes was observed after three weeks of culture (FIG. 12C). Most of the neurons were also positively stained for vesicular acetylcholine transporter (VAChT, FIG. 12D), which is essential for storage and release of acetylcholine. Many ChAT+ cells, especially after five weeks in culture, were positively labeled for synapsin on cell bodies and processes (FIG. 12E).

We assessed functional maturation using electrophysiological techniques (n=28 cells). The mean resting potential was −36.9±2.6 mV and input resistance was 920±57 MΩ. Single action potentials (AP's, FIG. 13Ai) or decrementing trains (FIG. 13Aii) were elicited by depolarizing current steps (0.15-0.2 nA×1s) in eleven of thirteen neurons tested. Spontaneous AP's triggered by spontaneous depolarizing synaptic inputs were also observed (FIG. 13B). Although not all cells survived recording and subsequent immunohistochemical analysis, double immunostaining with biocytin and ChAT demonstrated that many of the cells from which we recorded were motor neurons (FIG. 13E-G).

Voltage clamp analysis revealed time- and voltage-dependent inward and outward currents consistent with sodium and delayed rectifier potassium currents. Inward currents and action potentials were blocked by 1.0 μM tetrodotoxin (TTX, n=3), confirming the presence of voltage-activated sodium channels. Outward currents were not further characterized. We also observed spontaneous synaptic currents (FIG. 13C, n=21 of 23 cells tested). These were reduced in frequency but not eliminated by 1.0 μM TTX, demonstrating the existence of functionally intact synaptic neurotransmission. With a CsGluconate-based pipette solution, outward (inhibitory) currents decayed slowly (13.6 ms, n=10 events) and were blocked by a combination of strychnine and bicuculline, whereas the remaining inward (excitatory) currents decayed rapidly (2.1 ms, n=17 events) and were blocked by a combination of D-AP5 and CNQX (FIG.J 13C,E-G), demonstrating that inhibitory (GABA/glycine) and excitatory (glutamate) neurotransmission occur as in the intact spinal cord (Gao B.X., et al., J. Neurophysiol. 79:2277-2287 (1998)).

Our present study demonstrates that functional motor neurons can be efficiently generated from hESCs through neuroectodermal differentiation by FGF2, specification and/or caudalization by RA during the late phase of neuralization, and subsequent differentiation to post-mitotic motor neurons in the presence of the ventralizing morphogen SHH. Thus, fundamental principles of neural development learned from animals may be applied to human primates and recapitulated in vitro. In contrast to a recent demonstration of motor neuron differentiation from mESCs (Wichterle H. et al., Cell 110: 385-397 (2002)), we have dissected out the process of neuroectodermal differentiation and discovered that specification of early-born projection neurons such as spinal motor neurons requires treatment with morphogens before precursors become Sox1-expressing neuroectoderm cells.

meSCs have been first directed to neuroectodermal cells which are then treated with morphogens such as FGF8 and SHH for differentiation into dopaminergic neurons (Barberi T, et al., Nat. Biotechnol. 21:1200-1207 (2003); Lee S, et al., Nat. Biotechnol. 18:675-679 (2000)) or RA and SHH for motor neuron differentiation (Wichterle et al., supra, 2002). These observations seem to fit the notion that neurons are specified from epithelium in the neural tube. Our present observations indicate that the hESC-derived, Sox1-expressing neuroectodermal cells which also possess a forebrain phenotype are refractory to generate spinal motor neurons. The Sox1-expressing cells generated from hESCs in our culture system resemble those in the neural tube, as they form neural tube-like structures and express Sox1 after two weeks of differentiation from hESCs which are equivalent to a six-day-old human embryo (Zhang, supra, 2003). In vivo, the neural tube forms at the end of third week of human gestation (Wood H & Episkopou V, Mech. Dev. 86:197-201 (1999)) and Sox1 is expressed by the neuroectoderm during the formation of the neural tube in animals (Pevny et al., supra, 1998; Wood & Episkopou, supra, 1999). Our finding suggests that the specification of a class of neurons, at least large projection neurons such as motor neurons, begins before stem cells become Sox1-expressing neuroectodermal cells and may thus explain why brain-derived neuroepithelial cells fail to generate projection neurons of a different regional identity.

The functional motor neurons from the renewable source of hESCs offer generic human motor neurons for screening pharmaceuticals designed for treating motor neuron-related disorders such as ALS. These cells also provide a useful source for experimental cell replacement for motor neurons, which may someday lead to applications in patients with motor neuron diseases or spinal cord injury.

Methods

Culture of ESCs and Neural Differentiation hESCs (lines H1 and H9, passages 19 to 42) were cultured and passaged weekly on a feeder layer of irradiated embryonic mouse fibroblasts as described (Thomson et al., supra, 1998). The undifferentiated state of ESCs were confirmed by typical morphology and expression of Oct4 and SSEA4. For neuroectodermal differentiation, hESCs were aggregated for four days and then cultured on an adhesive plastic surface for ten days in F12/DMEM supplemented with N2, heparin (2 ng/ml), and FGF2 (20 ng/ml) or RA (Zhang et al., supra, 2001).

For motor neuron induction, the morphogen-treated neuroectodermal cells were plated onto ornithine/laminin-coated coverslips in a neuronal differentiation medium, which consisted of Neurobasal medium (Gibco), N2 supplement, and cAMP (Sigma, IgM) in the presence of RA (0.1 μM) and SHH (10-500 ng/ml, R&D) for one week. After that, BDNF, GDNF, and insulin-like growth factor-1 (IGF1) (10 ng/ml, PeproTech Inc.) were added to the medium and the concentration of SHH was reduced to 50 ng/ml.

Immunocytochemistry and Microscopy (Zhanq et al., supra, 2001)

Primary antibodies used in this study included polyclonal antibodies against neuronal class III $\beta_{III}$-tubulin (Covance Research Products, Richmond, Calif., 1:2000), nestin (Chemicon, Temecula, Calif., 1:750), Sox1 (Chemicon, 1:1000), synapsin I (Calbiochem, Darmstadt, German, 1:500), ChAT (Chemicon, 1:50), and VAChT (Chemicon, 1:1000), Isl½ (S. Pfaff), Otx2 (F. Vaccarino), and Oig2 (M. Nakafuku). Antibodies against MNR2 or HB9 (81.5C10), Isletl (40.2D6), Lim3 (67.4E12), Pax6, and Nkx2.2, were purchased from Developmental Studies Hybridoma Bank (DSHB, Iowa City, Iowa), and anti-HoxC8 from Covance Research Products (1:200). For identification of electrophysiologically recorded cells, biocytin (Molecular Probes) filled cells were labeled with streptavidin-FITC (sigma, 1:200) and stained for ChAT. Images were collected using a Spot digital camera mounted onto a Nikon fluorescent microscope 600 (FRYER INC, Huntley, Ill.) or a confocal microscope (Nikon, Tokyo, Japan). The specificity of antibodies against motor neuron transcription factors and homeodomain proteins, which were originally developed against non-primate tissues, were verified in embryonic (E34 or E36) rhesus monkey spinal cord and brain tissues (provided by the Wisconsin Primate Research Center).

Quantification

The population of HB9-expressing cells among total differentiated cells (Hoechst labeled) was counted by a person who was blind to experimental groups either manually using the Metamorph software (Universal Imaging Corporation, Downingtown, Pa.) or by stereological measurement. An area to be measured was outlined by a tracer, with the number of counting frames preset so that the scope sampled the measuring sites randomly using an automated stage movement operated by Stereo Investigator software (MicroBrightField Inc, Williston, Vt.). For counting areas with overlapping cells, the microscope was preset to move up and down to focus on the positive cells in different layers and the total cell number in the cluster was estimated by the software. Three to four coverslips in each group were counted and data were expressed as Mean ±SD.

RT-PCR Assays

RT-PCR amplifications were performed from hESC-derived neuroectodermal cells at different stages and motor neuron differentiation cultures. The following primers were used: HoxC8,5'-TTTATGGGGCTCAGCAAGAGG-3' (SEQ ID NO:11), 5'-TCCACTTCATCCTTCGGTTCTG-3' (SEQ ID NO:12), 318 bp; HoxC5,5'-TCGGGGTGCTTCCTTG-TAGC-3' (SEQ ID NO:13), 5'-TTCGTGGCAGGGAC-TATGGG-3' (SEQ ID NO:14), 290 bp; HoxB6,5'-AACTC-CACCTTCCCCGTCAC-3' (SEQ ID NO:15), 5'-CTTCTGTCTCGCCGAACACG-3' (SEQ ID NO:16), 340 bp; Otx2,5'-CAACAGCAGAATGGAGGTCA-3' (SEQ ID NO:17), 5'-CTGGGTGGAAAGAGAAGCTG-3' (SEQ ID NO:18), 429 bp; HoxBl, 5'-TCAGAAGGAGACGGAG-GCTA-3' (SEQ ID NO:19), 5'-GTGGGGGTGTTAGGT-TCTGA-3' (SEQ ID NO:20), 218 bp; GAPDH, 5'-ACCA-CAGTCCATGCCATCAC-3' (SEQ ID NO:1), 5'-TCCACCACCCTGTTGCTGTA-3' (SEQ ID NO:2), 450 bpi Olig-2, 5'-AAGGAGGCAGTGGCTTCAAGTC-3' (SEQ ID NO:21), 5'-CGCTCACCAGTCGCTTCATC-3' (SEQ ID NO:22), 315 bp; Nkx2.2, 5'-TGCCTCTCCTTCTGAACCT-TGG-3' (SEQ ID NO:23), 5'-GCGAAATCTGCCAC-CAGTTG-3' (SEQ ID NO:24), 337 bp; Irx-3, 5'-AA-GAACGCCACCAGGGAGAG-3' (SEQ ID NO:25), 5'-TTGGAGTCCGAAATGGGTCC-3' (SEQ ID NO:26), 473 bp; Pax6,5'-GGCAACCTACGCAAGATGGC-3' (SEQ ID NO:27), 5'-TGAGGGCTGTGTCTGTTCGG-3' (SEQ ID NO:28), 459 bp; SHH, 5'-CCAATTACAACCCCGACATC-3' (SEQ ID NO:29), 5'-CCGAGTTCTCTGCTTTCACC-3' (SEQ ID NO:30), 339 bp; Nkx6.1, 5'-ACACGAGAC-CCACTTTTTCCG-3' (SEQ ID NO:31), 5'-TGCTGGACT-TGTGCTTCTTCAAC-3' (SEQ ID NO:32), 335 bp.

Electrophysiology Recording

Electrophysiological properties of hESC-derived motor neurons were investigated in cultures differentiated for five to six weeks using whole-cell patch-clamp recording techniques (Gao B, et al., J. Neurophysiol. 79:2277-2287 (1998)). Tetrodotoxin (TTX, 1 μM, Sigma), bicuculline (20 μM, Sigma), strychnine (5 μM, Sigma), D-2-amino-5-phosphonovaleric acid (AP-5, 40 μM, Sigma) or 6-cyano-7-nitroquinoxaline-2, 3-dione (CNQX, 20 μM, RBI, Natick, Mass.) were applied in the bath solution to confirm the identity of voltage-activated or synaptic currents. For some experiments, 1% biocytin was added to the recording solution. Current- and voltage-clamp recordings were performed using a MultiClamp 700A amplifier (Axon Instruments, Union City, Calif.). Signals were filtered at 4 kHz, sampled at 10 kHz using a Digidata 1322A analog-digital converter (Axon Instruments), and acquired and stored on a computer hard disk using commercially available software (pClamp9, Axon Instruments). Access resistance was typically 8-15 MΩ and was compensated by 50-80% using amplifier circuitry. Spontaneous synaptic currents were detected using a template detection algorithm (Mini Analysis Program 5.6.28, Synaptosoft, Decatur, Ga.) and fitted to a monoexponential function using the Levenberg-Marquardt algorithm. Results are presented as mean ±SEM.

Example 4

Directed Differentiation of Ventral Spinal Progenitors and Motor Neurons from Human Embryonic Stem Cells by Small Molecules In General Potential use of hESCs in biotechnology and regenerative medicine depends upon a development of strategies for directed differentiation into functional cell/tissue types. In the past decade since the establishment of hESCs (Thomson et al. (1998), supra; and Reubinoff B, et al., Nat. Biotechnol. 18:399-404 (2000)), protocols have been devised to differentiate hESCs to enriched populations of specialized cells such as hematopoietic cells (Kaufman D, et al., Proc. Natl. Acad. Sci. USA 98:10716-10721 (2001)), cardiac cells (Mummery C, et al., J. Anat. 200:233-242 (2002)), skeletal muscle cells (Barberi T, et al., Nat. Med. 13:642-648 (2007)), pancreatic cells (D'Amour K, et al., Nat. Biotechnol. 24:1392-1401 (2006)), and neural cells (Carpenter M, et al., Exp. Neurol. 172:383-397 (2001); Reubinoff B, et al., Nat. Biotechnol. 19:1134-1140 (2001); Zhang S, et al, Nat. Biotechnol. 19:1129-1133 (2001)). With the exception of neuroepithelial cells that can be differentiated from hESCs with over 95% efficiency (Zhang S, et al., Nat. Biotechnol. 19:1129-1133 (2001); and Pankratz M, et al., Stem Cells, 25:1511-1520 (2007)), most differentiation protocols yield a mixed cell population. Differentiation to more specialized subtypes of neurons, such as midbrain dopamine neurons (Perrier A, et al., Proc. Natl. Acad. Sci. USA, 101:12543-12548 (2004); Yan Y, et al., Stem Cells 23:781-790 (2005)) and spinal motor neurons (Li X, Nat. Biotechnol. 23:215-221 (2005); Singh R, et al. Exp. Neurol. 196:224-234 (2005); Lee H, et al., Stem Cells, 0: 2007-0097v1 (2007)), becomes less efficient. Consequently, it is not known what non-target cells are in the mixture. These non-target cells are often the source of aberrant tissue formation in transplants (Roy N, et al., Nat. Med. 12:1259-1268 (2006); Brederlau A, et al., Stem Cells 24:1433-1440 (2006); Sonntag K, et al., Stem Cells 25:411-418 (2007)). Therefore, there exists a critical need to develop strategies for directed differentiation of hESCs to specialized functional cell types such as subtypes of neural progenitors and functional motor neurons.

Developmental principles are bases for devising strategies for directed neural differentiation of hESCs. In the ventral neural tube, there are five different progenitor domains (i.e., p0, p1, p2, p3 and pMN), which give rise to motor neurons and interneuron subtypes of the ventral spinal cord (Briscoe J, et al., Cell 101:435-445 (2000); and Jessell T, Nat. Rev. Genet. 1:20-29 (2000)). These progenitor domains are established mainly by interaction of Class I and Class II homeodomain (HD) proteins, which are inhibited or induced by graded secreted inductive factors, such as SHH (Briscoe J, et al., Cell 101:435-445 (2000); and Jessell, supra). The motor neuron domain (pMN) is flanked dorsally by the p2 domain (expressing Irx3) and ventrally by the p3 domain (marked by Nkx2.2) in the ventral neural tube. Expression of Olig2, a basic helix-loop-helix (bHLH) transcriptional factor, is a determinant factor in establishing the pMN domain (Lu Q, et al., Cell 109:75-86 (2002)). Subsequently, Olig2, together with a pan neuronal factor (Ngn2), induces downstream HD factors of motor neuron identity, such as HB9 (Mizuguchi R, et al., Neuron 31:757-771 (2001); Lee S, et al., Genes Dev. 19:282-294 (20.05)). Based on these developmental principles, we previously showed that hESCs can differentiate to spinal motor neurons with approximately 20% efficiency in an adherent culture by applying RA and SHH (Li X, Nat.

Biotechnol. 23:215-221 (2005)), similar to that from mESCs (Wichterle H, et al., Cell 110:385-397 (2002)). However, this efficiency is not ideal for a variety of analyses, and the identity of nearly 80% of the differentiated cells in the culture remains unknown. In the present study, we developed a simple, chemically defined suspension culture for a near-complete restriction of hESCs to a ventral spinal progenitor fate, with highly efficient generation of motor neurons. We further discovered that this process can be achieved by using a small molecule, purmorphamine, instead of SHH, making industrial production of motor neurons a simple process.

Results

RA and SHH Efficiently Restricted hESCs to Ventral Spinal Progenitors in a Suspension Culture.

hESCs, following separation from feeder cells through aggregation, differentiated to neuroepithelia (NE) in an adherent colony culture (Zhang et al., supra, 2001). Columnar epithelial cells appeared at day 8-10 of hESC differentiation and expressed anterior transcription factors such as Otx2 and Pax6, but not caudal markers like Hoxb4, which we refer to as primitive anterior NE (Pankratz M, et al., Stem Cells 25:1511-1520 (2007)).

For generating spinal progenitors, RA (0.1 µM) was added to the culture of primitive NE cells (day 10) (FIG. 14A). After 1 week of treatment (day 17), NE cells started to express Hoxb4 and organized into neural tube-like rosettes. These posteriorized neuroepithelial cell colonies were detached mechanically with a pipette. Unlike our previous adherent cultures, the neuroepithelial clusters were expanded in suspension in the same neural medium for an additional ten days. Almost all the cells were positive for Hoxb4 and negative for Otx2 (FIG. 14B). These results are in contrast to a control culture in which no morphogens (i.e., FGF2 or RA) were added (FIG. 14B). Hoxb4 is expressed by cells in both the hindbrain and spinal cord. Immunostaining for Phox2b, a marker positively staining for embryonic mouse hindbrain cells (Pattyn A, et al., Development 124:4065-4075 (1997)), indicated that very few cells expressed Phox2b (FIG. 14B). Thus, RA treatment under the suspension culture condition essentially restricted hESCs to spinal progenitors.

To ventralize the spinal progenitors, a more potent recombinant SHH (human SHH, R&D, 1845-SH, 100 ng/ml, with a mutation at Cys24) was added to the suspension culture at day 17, together with RA (0.1 µM) (FIG. 14A, C). Cells began to express ventral transcription factors (Olig2 or Nkx2.2) after one week of treatment, and the resulting ventral progenitor population reached a peak at 4 weeks of hESC differentiation. ~40% of the cells expressed Olig2, whereas 34±5% expressed Nkx2.2. Olig2 and Nkx2.2, however, were not co-expressed in the same cells at this stage (FIG. 14C). Irx3 is expressed by the dorsal spinal cord and dorsal domains (p0-2) of the ventral spinal cord (Briscoe J, et al., Cell 101:435-445 (2000)). About 12±4% of the cells expressed Irx3, but were negative for Pax7 (FIG. 14C), a transcription factor expressed by the dorsal spinal cord (Briscoe et al., supra; and Jessell T, Nat. Rev. Genet. 1:20-29 (2000)). Thus, about 86% of the cells were ventral spinal progenitors, (i.e., Nkx2.2+(p3), Irx3+/Pax7-(p0-2) and Olig2+(pMN)) in the presence of SHH. Some cells became post-mitotic neurons, including motor neurons, at this stage (see below), and almost all the differentiated progeny were restricted to a ventral spinal fate. In the absence of SHH (but with RA), only a few cells were positive for Olig2 and Nkx2.2 (FIG. 14C). Some cells were Irx3+, but Pax7-(po-p2), and most cells were positive for both Irx3 and/or Pax7 (FIG. 14C), Thus, the differentiated progeny without SHH were a mixture of ventral and dorsal spinal progenitors.

Ventral Spinal Progenitors Efficiently Differentiated to Motor Neurons in the Continual Presence of SHH.

We previously reported that motor neurons represent about 20% of differentiated progeny in cultures with reduced amounts of SHH (corresponding to about 10 ng/ml for the current SHH, R&D, 1845-SH) following the appearance of Olig2-expressing progenitors (Li X, Nat. Biotechnol. 23:215-221 (2005)). Our recent finding using genetically modified mESCs indicates that the transition from Olig2-expressing progenitors to post-mitotic motor neurons requires continual activation of SHH signaling (Du Z, et al., Mol. Cell. Neurosci. 33:371-380 (2006)). We therefore cultured Olig2-expressing progenitors in the suspension culture in the presence of 100 ng/ml of SHH in the present study.

As we described above, Olig2+ cells began to appear around 3.5 weeks, at which point there were almost no HB9+ cells. At 4 weeks of hESC differentiation, a small population of cells (~110%) was positive for HB9. At week 5, the population of HB9+ motor neurons increased to around 50% whereas the Olig2+ cells decreased to 28% (FIG. 15A, C). The expression of Olig2 and HB9 did not overlap, as shown by confocal microscopy analysis (FIG. 15B). Thus, motor neurons (HB9+) and their progenitors (Olig2+) accounted for nearly 80% of the total cell population.

Subsequently, and as described in our previous paper (Li, supra), choline acetyltransferase (ChAT), an enzyme for synthesizing the transmitter acetylcholine, was expressed by HB9+ motor neurons, indicating the maturation of motor neurons. SHH, at a higher concentration (200 ng/ml), or added earlier (at primitive NE stage), generated a similar population of Olig2+ and HB9+ cells in the culture (data not shown). Thus, ventral spinal progenitors efficiently differentiated to postmitotic motor neurons in the continual presence of SHH and RA.

Continued Presence of SHH Promotes the Division of Olig2 Progenitors.

We have reported that about 20% HB9-expressing motor neurons were differentiated in an adherent culture from hESCs, in which SHH was reduced during the motor neuron progenitor differentiation period (after 4 weeks). In the present study, we routinely generated about 50% motor neurons, with nearly all the differentiated cells being of a ventral spinal fate in a suspension culture in which SHH was applied continuously until the production of HB9 cells. This comparison suggests that SHH may also affect survival and/or proliferation of Olig2 progenitors in addition to their specification. Olig2-enriched clusters at 4 weeks were dissociated and adhered to coverslips in a neural medium (neural basal medium plus 2% B27) with or without SHH for 24 hours. In the absence of SHH, Olig2-expressing cells decreased to 20% of the total cells; whereas in the presence of SHH, the proportion of Olig2 cells (40%) was similar to that in suspension cultures (FIG. 16A,B). TUNEL analysis indicated that there was a similar population of positively labeled cells cultured with or without SHH, and the Olig2+ cells were not labeled by TUNEL (FIG. 16A,B). Hence, survival of the Olig2+ progenitors were not affected within the first day.

Immunostaining for Ki67, a protein expressed by proliferating cells, indicated that the proportion of Ki67-expressing Olig2 cells was significantly lower in the absence of SHH than in the presence of SHH (FIG. 16A,B). The total Ki67-expressing cell population did not exhibit a significant difference between the two groups (FIG. 16B). These findings suggested that SHH promotes proliferation of specified Olig2+ progenitors, resulting in an increase in motor neuron progenitors and subsequently post-mitotic motor neurons.

Purmorphamine Replaced SHH for Motor Neuron Generation.

The activity of commercially available SHH has been improved through a mutation at the N terminus; however, the activity remains variable. Purmorphamine is a small molecule that activates SHH signaling (Wu X, et al., Chem. Biol. 11:1229-1238 (2004)), possibly via Smoothened (Sinha S, et al., Nat. Chem. Biol. 2:29-30 (2006)). We therefore investigated whether purmorphamine can replace SHH in the generation of motor neurons.

Caudalized neural progenitors were treated with different concentrations of purmorphamine instead of SHH from day 17. Purmorphamine alone was not sufficient to induce the expression of Olig2+ or HB9+ cells. In the presence of RA (0.1 µM), Olig2 expression was robustly induced in the progenitors by all concentrations (0.5, 1 and 2 uM) of purmorphamine. Purmorphamine (with RA) at 1 µM generated the highest percentage of Olig2+ cells (around 40%) at 3.5 weeks (FIG. 17A), as confirmed by FACS analysis (FIG. 17B). Olig2+ cells were first observed within 5 days of treatment after isolating NE cells (day 22 of hESC differentiation), which was a few days earlier than in SHH/RA treated group. Remaining progenitor cells expressed other ventral markers such as Nkx2.2, but not Pax7 (not shown), similar to cultures in the presence of SHH.

Immunocytochemical analyses showed a similar pattern of HB9+ motor neuron differentiation as in the cultures with SHH (FIG. 17C, E). By 4.5 weeks of hESC differentiation, Olig2+ motor neuron progenitors and HB9+ motor neurons accounted for at least 80% of the differentiated population (FIG. 17E). After attachment on coverslips and differentiation for another week, most HB9+ motor neurons were also positive for ChAT (FIG. 17D), further confirming that they were motor neurons. Thus, purmorphamine treatment resulted in differentiation of ventral spinal progenitors and motor neurons at a similar efficiency as obtained with SHH.

Following 1 week of purmorphamine treatment, RT-PCR analysis showed that purmorphamine induced an almost identical expression pattern of class II factors like Nkx6.1 and Nkx2.2 as SHH (FIG. 17F). A combination of RA and purmorphamine resulted in high level expression of class II genes (Nkx6.1) and low level of expression of class I genes (Irx3, Pax7) in addition to Olig2 and Ngn2 (FIG. 17F), which has been shown to be necessary for motor neuron specification (Mizuguchi R. et al., Neuron 31:757-771 (2001); Lu Q, et al., Cell 109:75-86 (2002); and Lee H, et al., Stem Cells, 0:2007-0097v1 (2007)). In addition, purmorphamine increased levels of mRNA for Gli1, which is one of the targets in the SHH pathway. This result suggested that purmorphamine acts through a similar molecular pathway as SHH in inducing motor neuron specification.

Discussion

Based on our prior success in directed neural differentiation of hESCs and identification of signaling requirements for in vitro motor neuron differentiation, we have now developed a chemically defined suspension culture for a near-complete generation of ventral spinal progenitors for subsequent highly efficient motor neuron generation. In this culture, ventral spinal progenitors and post-mitotic motor neurons accounted for over 96% of the total hESC-differentiated progeny. To our knowledge, this is the most efficient directed differentiation approach for producing defined classes of neurons in chemically defined systems without immunochemical selection procedures. Furthermore, we discovered that purmorphamine replaced SHH throughout the entire process of ventral spinal progenitor specification and motor neuron differentiation with a similar efficiency. Thus, the complex process of motor neuron generation in the spinal cord can be mimicked by the two simple chemicals—RA and purmorphamine. This discovery paves a way for large scale production of spinal neurons and motor neurons in industry.

Differentiation of mESCs and hESCs using RA and SHH (or SHH agonists) previously yielded cell populations with about 20% of the differentiated progeny being motor neurons (Wichterle H, et al., Cell 110:385-397 (2005); Li, supra). However, the identity of the other nearly 80% of the cells in the culture remained unknown. Our present study clearly demonstrated that nearly all the differentiated cells produced using our modified protocol are spinal cord neural cells and carry the ventral spinal cord characteristics but not those of the fore-, mid- and hindbrain, or dorsal spinal cord. It is thus remarkable that pluripotent hESCs can be limited to cells with such a restricted regional identity at such a high efficiency.

In our previous protocol, we reduced the amount of SHH in the culture once the Olig2-expressing motor neuron progenitors were generated (Li, supra). We recently discovered that the differentiation of Olig2 progenitors to post-mitotic motor neurons, as well as specification of Olig2 progenitors from the neuroectodermal cells, requires SHH (Du et al. supra). Continued application of SHH indeed increased the production of HB9-expressing motor neurons in the present study. We further discovered that SHH also promoted the proliferation of the Olig2-expressing motor neuron progenitors. This may explain why both motor neuron progenitors and post-mitotic motor neurons increased significantly in the cultures with the continual presence of SHH.

The activity of recombinant SHH is variable, and the cost for high doses of SHH in long-term cultures of human cells is high. Cell permeable small molecules are a potential solution (Ding S & Schultz P, Nat. Biotechnol. 22:833-840 (2004)). One of these small molecules is purmorphamine, which activates Gli1, a downstream target of the SHH pathway (Wu X, et al., Chem. Biol. 11:1229-1238 (2004)). We show here that purmorphamine activates an almost identical set of transcription factors that are involved in the specification of ventral spinal progenitors and motor neurons, as well as activated Gli1. We have also found that Olig2-expressing motor neuron progenitors appeared several days earlier following purmorphamine treatment than after treatment with SHH. This may be due to improved penetration and direct downstream effect by purmorphamine (Wu et al., supra; Riobo N, et al., Proc. Natl. Acad. Sci. USA 103:12607-12612 (2006); Sinha S, et al., Nat. Chem. Biol. 2:29-30 (2006)). This may be especially helpful in our current approach using suspension culture following neuroepithelial differentiation. Continued adherent culture often resulted in a ring of flat, potentially non-neural cells in each colony (Zhang et al., supra, 2001; Li, supra), which may reduce the proportion of cell of a motor neuron lineage. Suspension cultures limited the differentiation of these flat cells, and together with the permeable nature of purmorphamine, may account for the high efficiency of motor neuron production. The use of purmorphamine not only achieved a high efficiency of differentiation and decreased cost, but also makes large scale production feasible due to its stable chemical nature and easy preparation procedure.

The drastically simplified, but much more efficient, protocol for differentiation of ventral spinal progenitors and motor neurons enables virtually every laboratory to produce large amounts of target cells for genetic and/or epigenetic analyses without the need for cell sorting (Singh et al., supra), which is often traumatic to large projection neurons like motor neurons. The strategy described herein is likely applicable to many other cell lineages.

Experimental Procedures
Culture of Neuroepithelial Cells and Motor Neurons.

hESCs (lines H1 and H9, passages 19 to 42) were cultured and passaged weekly on a feeder layer of irradiated embryonic mouse fibroblasts as described previously (Thomson et al., supra, 1998). The procedure for generating neuroepithelial cells from hESCs was essentially the same as described previously (Zhang et al., supra, 2001).

For motor neuron induction, hESC-derived neuroepithelial cells at day 10 were first treated with RA (0.1 µM) for caudalization in a neural medium, which consisted of DMEM/F12 (Gibco), N2 supplement, heparin (Sigma, 2 µg/ml) and cAMP (Sigma, 1 µM). One week later (day 17), the posteriorized neuroectodermal cells were isolated, and suspended in the same neural medium in the presence of RA (0.1 µM) and SHH (100-200 ng/ml; R&D, 1845-SH) for one week. After that (day 24), brain-derived neurotrophic factor (BDNF), glial-derived neurotrophic factor (GDNF) and insulin-like growth factor-1 (IGF1) (10 ng/ml, PeproTech Inc.) were added to the culture. Purmorphamine (Calbiochem) at different concentrations (0.5, 1, 2 and 5 µM) was used instead of SHH in some experiments (see Results).

Immunocytochemistry and Quantification.

Immunohistochemical staining was performed according to Zhang et al., (Zhang et al. (2001), supra). Primary antibodies used in this study included polyclonal antibodies against Olig2 (1:500, Santa Cruz), Ki67 (1:200, Zymed), Otx2 (1:2000, Chemicon) and ChAT (1:200, Chemicon). Antibodies against MNR2 or HB9 (81.5C10) (1:50), Pax7 (1:2000), Nkx2.2 (1:50) and Hoxb4 (1:50) were purchased from Developmental Studies Hybridoma Bank (DSHB, Iowa City, Iowa). Polyclonal Phox2b and Irx3 antibodies were kindly provided by Dr. Jean-François Brunet (CNRS; École Normale Supérieure, Paris) and Dr. Thomas Jessell (Columbia University; New York, N.Y.), respectively. Images were collected using a Spot digital camera mounted onto a Nikon fluorescent microscope 600 (Fryer Inc.; Huntley, Ill.) or a confocal microscope (Nikon; Tokyo, Japan).

The population of Olig2 or HB9-expressing cells among total differentiated cells (Hoechst labeled) was counted in two ways, as previously described (Li et al. (2005), supra). Six to twelve clusters in each group were counted and data were expressed as Mean ± SEM. Differences between groups were compared by ANOVA test, and the statistical significance was defined as two-sided (p=0.05).

Fluorescence-Activated Cell Sorting (FACS)

Cells were harvested using Accutase® (Innovative Cell), gently dissociated to single cells and washed with a FACS buffer (PBS, 0.1% NaN3, 2% donkey serum). After being fixed and permeabilized with ice cold 0.1% paraformaldehyde for 10 minutes and with 90% methanol for 30 minutes, cells Were then incubated in primary antibody (Olig2, goat IgG, 1:500) or a goat IgG control at 1 mg protein/1 million cells. Cells were then washed and incubated with a corresponding secondary antibody, such as Alexa 488 conjugated, donkey, anti-goat IgG, for 2 hours followed by washing steps. Cells were analyzed by a Becton Dickinson FACSCaliber and analyzed with CellQuest Pro (BD Biosciences).

RT-PCR assays

Total RNA was extracted from motor neuron differentiation cultures using RNA STAT-60 (Tel-Test, Inc.; Friendswood, Tex.). cDNA was synthesized using SuperScript III first-strand synthesis system (Invitrogen; Carlsbad, Calif.) according to the manufacturer's protocol and was used as templates for the PCR reaction. PCR reaction was performed in a 15 µl mixture containing cDNA, primers and 1×PCR Master mix (Promega; Madison, Wis.). The following primers were used: Olig-2,5'-AAGGAGGCAGTGGCT-TCAAGTC-3' (SEQ ID NO:21), 5'-CGCTCAC-CAGTCGCTTCATC-3' (SEQ ID NO:22), 315 bp; Nkx2.2, 5'-TGCCTCTCCTTCTGAACCTTGG-3' (SEQ ID NO:23), 5'-GCGAAATCTGCCACCAGTTG-3' (SEQ ID NO:24), 337 bp; Irx-3,5'-AGAACGCCACCAGGGAGAG-3' (SEQ ID NO:25), 5'-TTGGAGTCCGAAATGGGTCC-3' (SEQ ID NO:26), 473 bp; Pax6,5'-GGCAACCTACGCAAGATGGC-3' (SEQ ID NO:27), 5'-TGAGGGCTGTGTCTGTTCGG-3' (SEQ ID NO:28), 459 bp; Nkx6.1, 5'-ACACGAGAC-CCACTTTTTCCG-3' (SEQ ID NO:31), 5'-TGCTGGACT-TGTGCTTCTTCAAC-3' (SEQ ID NO:32), 335 bp; GAPDH, 5'-ACCACAGTCCATGCCATCAC-3' (SEQ ID NO:1), 5'-TCCACCACCCTGT TGCTGTA-3' (SEQ ID NO:2), 450 bp; HB9,5'-GATGCCCGACTTCAACTCCC-3' (SEQ ID NO:33), 5'-CCTTCTGTTTCTCCGCTTCCTG-3' (SEQ ID NO:34), 269 bp; Ngn-2,5'-TGATTCCTCGGT-TGTTTCTTGC-3' (SEQ ID NO:35), 5'-AAAGCAGATGC-CAGCCATTG-3' (SEQ ID NO:36), 399 bp; Pax7,5'-CACT-GTGACCGAAGCACTGGT-3' (SEQ ID NO:37), 5'-CCTCTGTCAGCTTGGTCCTC-3' (SEQ ID NO:38), 352 bp; and Gli1, 5'-TTCCTACCAGAGTCCCAAGT-3' (SEQ ID NO:39), 5'-CCCTATGTGAAGCCCTATTT-3' (SEQ ID NO:40), 185 bp.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. A method of creating a population of human ventral spinal progenitor cells, the method comprising the steps of:
   (a) obtaining a synchronous population of cells that are cultured from human embryonic stem cells, that are characterized by an early rosette morphology and that are Pax6+/Sox1−;
   (b) culturing the cells of step (a) with a sufficient amount of retinoic acid in adherent culture, wherein the resulting cells are positive for Hoxb4 and are negative for at least one of Otx2 or Bf1;
   (c) expanding the resulting cells of step (b) in a suspension culture with a sufficient amount of retinoic acid; and
   (d) culturing the cells of step (c) in a suspension culture with a sufficient amount of retinoic acid and an agent selected from the group consisting of sonic hedgehog and purmorphamine, wherein at least 80% of the resulting cells are Olig2+, Nkx2.2+, Irx3+ and Pax7−.

2. The method of claim 1, wherein the time period that the synchronous population of cells recited in step (a) are cultured from embryonic stem cells is between 8 days to 10 days.

3. The method of claim 1, wherein step (b) is between 6 days to 8 days.

4. The method of claim 1, wherein step (d) is between 9 days to 14 days.

5. The method of claim 1, wherein the population of Pax6+/Sox1− cells is at least 70% of the synchronous cell population of step (a).

6. The method of claim 1, wherein the cells of step (c) are expanded for 6-8 days prior to step (d).

7. A population of human ventral spinal progenitor cells created by the method of claim 1, wherein at least 80% within the population are human ventral spinal progenitor cells and are Hox4+, HoxC8+, Olig2+, Nkx2.2+, Irx3+, Otx2−, Pax7− and Phox2b−.

8. The method of claim 1, wherein purmorphamine is present at a concentration of at least 0.5 μM.

9. The method of claim 1, wherein purmorphamine is present at a concentration of at least 1 μM.

10. The method of claim 1, wherein the cells are cultured in a suspension culture with a sufficient amount of retinoic acid and purmorphamine in step (d).

* * * * *

UNITED STATES PATENT AND TRADEMARK OFFICE
CERTIFICATE OF CORRECTION

| | | |
|---|---|---|
| PATENT NO. | : 8,153,424 B2 | Page 1 of 1 |
| APPLICATION NO. | : 11/932582 | |
| DATED | : April 10, 2012 | |
| INVENTOR(S) | : Zhang et al. | |

It is certified that error appears in the above-identified patent and that said Letters Patent is hereby corrected as shown below:

Column 4, line 40 "(M)" should read -- (AA) --

Column 37, line 27 "bpi" should read -- $bp_i$ --

Column 38, line 64 "(20.05))" should read -- (2005)) --

Signed and Sealed this
Tenth Day of July, 2012

David J. Kappos
*Director of the United States Patent and Trademark Office*